US008580714B2

(12) United States Patent
Almagro et al.

(10) Patent No.: US 8,580,714 B2
(45) Date of Patent: Nov. 12, 2013

(54) METHODS OF AFFINITY MATURING ANTIBODIES

(75) Inventors: Juan Carlos Almagro, Radnor, PA (US); Johan Fransson, San Diego, CA (US); Gopalan Raghunathan, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 342 days.

(21) Appl. No.: 12/904,549

(22) Filed: Oct. 14, 2010

(65) Prior Publication Data

US 2011/0092372 A1 Apr. 21, 2011

Related U.S. Application Data

(60) Provisional application No. 61/251,445, filed on Oct. 14, 2009.

(51) Int. Cl.
*C40B 10/00* (2006.01)

(52) U.S. Cl.
USPC .......................................................... 506/26

(58) Field of Classification Search
None
See application file for complete search history.

(56) References Cited

U.S. PATENT DOCUMENTS

| | | | |
|---|---|---|---|
| 5,643,768 A | 7/1997 | Kawasaki | |
| 6,521,427 B1 | 2/2003 | Evans | |
| 6,670,127 B2 | 12/2003 | Evans | |
| 6,849,425 B1 | 2/2005 | Huse et al. | |
| 7,117,096 B2 | 10/2006 | Luo et al. | |
| 2005/0266000 A1 | 12/2005 | Bond et al. | |

FOREIGN PATENT DOCUMENTS

| | | |
|---|---|---|
| WO | WO 2006/014498 A2 | 2/2006 |
| WO | WO 2009/085462 A1 | 7/2009 |

OTHER PUBLICATIONS

Almagro et al. (Jul. 31, 2006) Journal of Molecular Recognition vol. 19 pp. 413 to 422 (hereinafter referred to as "Almagro 2006").*
Persson et al. (Mar. 24, 2006) Journal of Molecular Biology vol. 357 pp. 607 to 620 (hereinafter referred to as "Persson").*
Al-Lazikani, et al., "Standard Conformations for the Canonical Structures of Immunoglobulins," Journal of Molecular Biology, 273: 927-948 (1997).
Juan C. Almagro, et al., "Identification of differences in the specificity-determining residues of antibodies that recognize antigens of different size: implications for the rational design of antibody repertoires," Journal of Molecular Recognition, 17: 132-143 (2004).
Barbas, et al., "In vitro evolution of a neutralizing human antibody to human immunodeficiency virus type 1 to enhance affinity and broaden strain cross-reactivity," Proceedings of the National Academy of Science USA, 91: 3809-3813 (1994).
Chothia, et al., "Structural Repertoire of the Human $V_H$ Segments," Journal of Molecular Biology, 227: 799-817 (1992).
Cobaugh, et al., "Synthetic Antibody Libraries Focused Towards Peptide Ligands," Journal of Molecular Biology, 378: 622-633 (2008).
Fellouse, et al., "Molecular Recognition by a Binary Code," Journal of Molecular Biology, 348: 1153-1162 (2005).

(Continued)

*Primary Examiner* — Ardin Marschel
*Assistant Examiner* — Christian Boesen
(74) *Attorney, Agent, or Firm* — Kirk Baumeister

(57) ABSTRACT

The invention relates to methods of affinity maturing antibodies.

6 Claims, 25 Drawing Sheets

(56) References Cited

OTHER PUBLICATIONS

Fellouse, et al., "Synthetic antibodies from a four-amino-acid code: A dominant role for tyrosine in antigen recognition," Proceedings of the National Academy of Science, 101(34): 12467-12472 (2004).
Groves, et al., "Affinity maturation of phage display antibody populations using ribosome display," Journal of Immunological Methods, 313: 129-139 (2006).
Hanes, et al., "In vitro selection and evolution of functional proteins by using ribosome display," Proceedings of the National Academy of Science, 94: 4937-4942 (1997).
Hoet, et al., "Generation of high-affinity human antibodies by combining donor-derived and synthetic complementarity-determining-region diversity," Nature Biotechnology, 23(3): 344-348 (2005).
Hennie R. Hoogenboom, "Selecting and screening recombinant antibody libraries," Nature Biotechnology, 23(9): 1105-1116 (2006).
Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).
Kohler, et al., "Continuous cultures of fused cells secreting antibody of predefined specificity," Nature, 256: 495-497 (1975).
Lonberg, et al., "Antigen-specific human antibodies from mice comprising four distinct genetic modifications," Nature, 368: 856-859 (1994).
Luane, et al., "Systematic Exploration of the Antigen Binding Activity of Synthetic Peptides Isolated from the Variable Regions of Immunoglobulins," the Journal of Biological Chemistry, 272(49): 30937-30944 (1997).
Padlan, et al., "Identification of specificity-determining residues in antibodies," FASEB Journal, 9: 133-139 (1995).
Roberts, et al., "RNA-peptide fusions for the in vitro selection of peptides and proteins," Proceedings of the National Academy of Science USA, 94: 12297-12302 (1997).
Noah E. Robinson, "Protein deamidation," Proceedings of the National Academy of Science, 99(8): 5283-5288 (2002).
Schier, et al., "Isolation of Picomolar Affinity Anti-c-erbB-2 Single-chain Fv by Molecular Evolution of the Complementarity Determining Regions in the Center of the Antibody Binding Site," Journal of Molecular Biology, 263: 551-567 (1996).
Shi, et al., "De Novo Selection of High-Affinity Antibodies from Synthetic Fab Libraries Displayed on Phage as pIX Fusion Proteins," Journal of Molecular Biology, 397: 385-396 (2010).
Sidhu, et al., "Synthetic therapeutic antibodies," Nature Chemical Biology, 2(12): 682-688 (2006).
Steidl, et al., "In vitro affinity maturation of human GM-CSF antibodies by targeted CDR-diversification," Molecular Immunology, 46: 135-144 (2008).
PCT International Search Report dated Apr. 22, 2011.

* cited by examiner

Figure 1.

| Numbering | | Antigen binding site | | Protein | | | Peptide | | | Hapten | | |
|---|---|---|---|---|---|---|---|---|---|---|---|---|
| | | | | rSDRU at indicated cutoff | | | | | | | | |
| Kabat | Chothia | CDR | HVL | 40 | 15 | 5 | 40 | 15 | 5 | 40 | 15 | 5 |
| 23 | 23 | | | | | | | | | | | |
| 24 | 24 | | | | | | | | | | | |
| 25 | 25 | | | | | | | | | | | |
| 26 | 26 | | | | | | | | | | | |
| 27 | 27 | | | | | | | | | | | |
| a | 28 | | | | | | | | | | | |
| b | 29 | | | | | | | | | | | |
| c | 30 | | | | | | | | | | | |
| d | a | | | | | | | | | | | |
| e | b | | | | | | | | | | | |
| 28 | c | | | | | | | | | | | |
| 29 | d | | | | | | | | | | | |
| 30 | e | | | | | | | | | | | |
| 31 | 31 | | | | | | | | | | | |
| 32 | 32 | | | | | | | | | | | |
| 33 | 33 | | | | | | | | | | | |
| 34 | 34 | | | | | | | | | | | |
| 35 | 35 | | | | | | | | | | | |
| 36 | 36 | | | | | | | | | | | |
| 37 | 37 | | | | | | | | | | | |
| 48 | 48 | | | | | | | | | | | |
| 49 | 49 | | | | | | | | | | | |
| 50 | 50 | | | | | | | | | | | |
| 51 | 51 | | | | | | | | | | | |
| 52 | 52 | | | | | | | | | | | |
| 53 | 53 | | | | | | | | | | | |
| 54 | 54 | | | | | | | | | | | |
| 55 | 55 | | | | | | | | | | | |
| 56 | 56 | | | | | | | | | | | |
| 57 | 57 | | | | | | | | | | | |
| 88 | 88 | | | | | | | | | | | |
| 89 | 89 | | | | | | | | | | | |
| 90 | 90 | | | | | | | | | | | |
| 91 | 91 | | | | | | | | | | | |
| 92 | 92 | | | | | | | | | | | |
| 93 | 93 | | | | | | | | | | | |
| 94 | 94 | | | | | | | | | | | |
| 95 | 95 | | | | | | | | | | | |
| a | a | | | | | | | | | | | |
| b | b | | | | | | | | | | | |
| 96 | 96 | | | | | | | | | | | |
| 97 | 97 | | | | | | | | | | | |
| 98 | 98 | | | | | | | | | | | |

Figure 2.

| Numbering | | Antigen binding site | | Protein | | | Peptide | | | Hapten | | |
|---|---|---|---|---|---|---|---|---|---|---|---|---|
| | | | | rSDRU at indicated cutoff | | | | | | | | |
| Kabat | Chothia | CDR | HVL | 40 | 15 | 5 | 40 | 15 | 5 | 40 | 15 | 5 |
| 25 | 25 | | | | | | | | | | | |
| 26 | 26 | | | | | | | | | | | |
| 27 | 27 | | | | | | | | | | | |
| 28 | 28 | | | | | | | | | | | |
| 29 | 29 | | | | | | | | | | | |
| 30 | 30 | | | | | | | | | | | |
| 31 | 31 | | | | | | | | | | | |
| 32 | a | | | | | | | | | | | |
| 33 | b | | | | | | | | | | | |
| 34 | 32 | | | | | | | | | | | |
| 35 | 33 | | | | | | | | | | | |
| a | 34 | | | | | | | | | | | |
| b | 35 | | | | | | | | | | | |
| 46 | 46 | | | | | | | | | | | |
| 47 | 47 | | | | | | | | | | | |
| 48 | 48 | | | | | | | | | | | |
| 49 | 49 | | | | | | | | | | | |
| 50 | 50 | | | | | | | | | | | |
| 51 | 51 | | | | | | | | | | | |
| 52 | 52 | | | | | | | | | | | |
| a | a | | | | | | | | | | | |
| b | b | | | | | | | | | | | |
| c | c | | | | | | | | | | | |
| 53 | 53 | | | | | | | | | | | |
| 54 | 54 | | | | | | | | | | | |
| 55 | 55 | | | | | | | | | | | |
| 56 | 56 | | | | | | | | | | | |
| 57 | 57 | | | | | | | | | | | |
| 58 | 58 | | | | | | | | | | | |
| 59 | 59 | | | | | | | | | | | |
| 60 | 60 | | | | | | | | | | | |
| 61 | 61 | | | | | | | | | | | |
| 62 | 62 | | | | | | | | | | | |
| 63 | 63 | | | | | | | | | | | |
| 64 | 64 | | | | | | | | | | | |
| 65 | 65 | | | | | | | | | | | |
| 66 | 66 | | | | | | | | | | | |
| 94 | 94 | | | | | | | | | | | |
| 95 | 95 | | | | | | | | | | | |
| 96 | 96 | | | | | | | | | | | |
| 97 | 97 | | | | | | | | | | | |
| 98 | 98 | | | | | | | | | | | |
| 99 | 99 | | | | | | | | | | | |
| 100 | 100 | | | | | | | | | | | |
| a | a | | | | | | | | | | | |
| b | b | | | | | | | | | | | |
| c | c | | | | | | | | | | | |
| 101 | 101 | | | | | | | | | | | |
| 102 | 102 | | | | | | | | | | | |
| 103 | 103 | | | | | | | | | | | |

Figure 3a.

| PDB Code | IMGT Name | Release | Ligand |
|---|---|---|---|
| 1A14 | NC10 | 199805 | Calcium Ion,Neuraminidase |
| 1A2Y | D1.3 | 199804 | Lysozyme C [hen egg white] (HEL) EC:3.2.1.17 D18A |
| 1AR1 | 1AR1 | 199802 | Cytochrome c oxidase [Paracoccus denitrificans]... |
| 1C08 | Hyhel-10 | 200007 | Lysozyme C [hen egg white] (HEL) EC:3.2.1.17 |
| 1DZB | 1F9 | 200011 | Lysozyme C [turkey egg white] EC:3.2.1.17,Lysoz... |
| 1EGJ | Bion-1 | 200102 | GM-CSF/IL-3/IL-5 receptor common beta chain (be... |
| 1EO8 | Bh151 | 200011 | Hemagglutinin HA1 and HA2 bromelain released fr... |
| 1FE8 | Ru5 | 200104 | von Willebrand factor (vWF) A3 domain,von Wille... |
| 1FJ1 | La2 | 200010 | Borrelia burgdorferi (spirochete, Lyme disease ... |
| 1FNS | Nmc-4 | 200010 | von Willebrand factor (vWF) A1 domain; residues... |
| 1FSK | Mst2 / Bv16 | 200010 | Major birch pollen allergen Bet v1,Major birch ... |
| 1H6 | Cb41 | 200102 | HIV-1 p24 Pep-5, epitope-related peptide |
| 1IGC | MOPC21 | 199506 | Streptococcus protein G domain III |
| 1IKF | CSA SPECIFIC IG | 199505 | Cyclosporin A(CsA) |
| 1IQD | BO2C11 | 200108 | Factor VIII C2 domain [Human] |
| 1J1O | IG VH,Anti-Lysozyme | 200301 | Lysozyme C |
| 1JHL | D11.15 | 199401 | Lysozyme [pheasant egg white] EC:3.2.1.17 |
| 1JPS | D3H44 | 200202 | Tissue Factor |
| 1JRH | A6 | 199803 | Interferon-gamma-receptor alpha chain C105S |
| 1KCR | PC283 | 200205 | PS1 Peptide |
| 1MHH | FAB | 200301 | Protein L Domain C,Protein L Domain C |
| 1MLC | D44.1 | 199506 | Lysozyme C [hen egg white] (HEL) EC:3.2.1.17,Ly... |
| 1NBY | Hyhel-63 | 200304 | Lysozyme C [hen egg white] (HEL) EC:3.2.1.17 |
| 1NCA | NC41 | 199401 | Neuraminidase [influenza virus, A/Tern strain, ... |
| 1NDG | Hyhel-8 | 200306 | Lysozyme C [hen egg white] (HEL) EC:3.2.1.17 |
| 1OB1 | Antibody | 200305 | Merozoite Surface Protein 1,Merozoite Surface P... |
| 1ORS | 33H1 | 200305 | Potassium Channel |
| 1OSP | 184.1 | 199704 | Outer surface protein A (Osp A) S84C |
| 1OTS | FAB Fragment (Lig. | 200304 | Voltage-Gated Clc-Type Chloride Channel Eric,Vo... |
| 1P2C | F10.6.6 | 200402 | Lysozyme C [hen egg white] (HEL) EC:3.2.1.17,Ly... |
| 1QFU | HA NEUTRALIZING IG | 199912 | Hemagglutinin HA1 and HA2 [influenza virus] bro... |
| 1QKZ | MN14C11.6 | 200002 | Porin (PorA) [Neisseria meningitidis serosubtyp... |
| 1R0A | Fab28 | 200408 | 5'-,5'-,Reverse Transcriptase (POL),Reverse Tra... |

Figure 3a. (continued)

| | | | |
|---|---|---|---|
| 1RJL | FAB H6831 H-CHAIN | 200411 | OUTER SURFACE PROTEIN B,OUTER SURFACE P |
| 1TJG | 2F5 | 200410 | GP41 |
| 1TQB | VRQ14 | 200409 | PRION PROTEIN |
| 1TY6 | 10E5 | 200410 | EPTIFIBATIDE |
| 1TZH | YADS1 | 200408 | VASCULAR ENDOTHELIAL GROWTH FACTOR A,V |
| 1TZI | FAB YADS2 LIGHT C. | 200408 | VASCULAR ENDOTHELIAL GROWTH FACTOR A |
| 1UJ3 | HATR-5 | 200407 | TISSUE FACTOR |
| 1UWX | P1.2 | 200506 | Protein G',Protein G',Class 1 outer membrane pr... |
| 1UZ8 | Anti-Lewis X | 200407 | Lewis X antigen,Lewis X antigen |
| 1V7M | TN1 | 200403 | THROMBOPOIETIN,THROMBOPOIETIN |
| 1WEJ | E8 | 199812 | Cytochrome c [horse] |
| 1YQV | HyheI-5 | 200504 | Lysozyme C [hen egg white] (HEL) EC:3.2.1.17 |
| 1ZTX | E16 | 200510 | Enveloppe protein DIII |
| 2ADF | 82D6A3 | 200512 | VON WILLEBRAND FACTOR |
| 2AEP | Mem5 | 200512 | NEURAMINIDASE |
| 2BDN | 11K2 | 200606 | SMALL INDUCIBLE CYTOKINE A2 |
| 2BRR | MN20B9.34 | 200509 | Class 1 outer membrane protein peptide 18-26 (Q... |
| 2CMR | D5 | 200610 | Glycerol,TRANSMEMBRANE GLYCOPROTEIN |
| 2DQC | ANTI-LYSOZYME | 200701 | LYSOZYME C |
| 2FD6 | ATN-615 | 200602 | UROKINASE-TYPE PLASMINOGEN ACTIVATOR,UR |
| 2FJG | G6 | 200602 | VASCULAR ENDOTHELIAL GROWTH FACTOR A,V |
| 2G5B | 6A7 | 200607 | BAX PEPTIDE,BAX PEPTIDE,BAX PEPTIDE,BAX P |
| 2GHW | 80R | 200609 | Spike,Spike |
| 2HJF | ANTIBODY | 200612 | VOLTAGE-GATED POTASSIUM CHANNEL |
| 2HKF | IMMUNOGLOBULIN HE. | 200711 | CARBONIC ANHYDRASE 9 |
| 2HMI | 28 | 199810 | HIV-1 reverse transcriptase (HIV-1 RT) EC:2.7... |
| 2HRP | F11.2.32 | 199712 | HIV-1 protease peptide; residues: 36-46,HIV-1 p... |
| 2HVK | ANTIBODY FAB | 200702 | Nonan-1-ol,Tetrabutylammonium Ion,,VOLTAGE-GATE |
| 2IBZ | FV HEAVY KAPPA | 200703 | Protoporphyrin IX Containing Fe,UBIQUINOL-CYTOC. |
| 2IH3 | FAB HEAVY CHAIN | 200611 | VOLTAGE-GATED POTASSIUM CHANNEL |
| 2J4W | F8.12.19 | 200702 | APICAL MEMBRANE ANTIGEN 1 |
| 2JEL | JEL42 | 199805 | Histidine-containing protein of the phosphoenol... |
| 2NY1 | 17B | 200702 | ENVELOPE GLYCOPROTEIN GP120 |
| 2OZ4 | FAB FRAGMENT, HEA. | 200710 | INTERCELLULAR ADHESION MOLECULE 1,TRIS,TI |
| 2UZI | Anti-RAS FV-HEAVY. | 200706 | GTP-bound HRAS (GTPase Hras, p21 ras, H-Ras-1,.. |

Figure 3b.

| PDB Code | MGT Name | Rlas | Ligand |
|---|---|---|---|
| 1A3R | 8F5 | 199804 | Human rhinovirus (serotype 2) VP2 (viral capsid... |
| 1AI1 | 59.1 | 199705 | V3 loop constrained peptide analogue (Aib142) |
| 1E4X | Tab2 | 200107 | Cyclic peptide,Cyclic peptide |
| 1F58 | 58.2 | 199912 | HIV-1 gp120 V3 loop, 24 residue peptide; residu... |
| 1F90 | Lnkb-2 | 200107 | Antigenic nonapeptide |
| 1FRG | 26/9 | 199405 | Hemagglutinin HA1 [influenza virus, strain X47]... |
| 1GGI | 50.1 | 199310 | HIV-1 gp120 V3 loop; residues: 311-328 (Mn isol... |
| 1I8K | Epidermal Growth .. | 200203 | Epidermal Growth Factor Receptor, Egfrviii |
| 1IFH | 17/9 | 199310 | Hemagglutinin HA1 [influenza virus, strain X47]... |
| 1KC5 | PC287 | 200207 | PS1 Peptide |
| 1KCS | PC282 | 200250 | PS1 Peptide |
| 1KTR | Anti-His Tag Anti. | 200250 | Peptide Linker,Oligohistidine Peptide Antigen |
| 1MPA | Mn12H2 | 199790 | Porin (PorA) [Neisseria meningitidis, sero-subt... |
| 1MVU | IG VDJ-REGION (HE. | 200310 | P-GLYCOPROTEIN |
| 1N0X | HIV NEUTRALIZING . | 200404 | B2.1 PEPTIDE,B2.1 PEPTIDE |
| 1NAK | 83.1 | 200311 | MP1,MP1 |
| 1PZ5 | Sya/J6 | 200311 | Octapeptide (MDWNMHAA) carbohydrate mimicry |
| 1SVZ | 1696 | 200503 | EPITOPE PEPTIDE CORRESPONDING TO N-TERMINUS |
| 1TET | Te33 | 199401 | Cholera toxin peptide 3 (CTP3); residues: 1-15 |
| 1XGY | K42-41L | 200509 | Rhodopsin epitope mimetic peptide,Rhodopsin epi... |
| 2A6I | 36-65 | 200606 | DODECAPEPTIDE |
| 2CK0 | Fab131 | 200308 | Angiotensin II 11-mer |
| 2FX7 | 4E10 | 200612 | FRAGMENT OF HIV GLYCOPROTEIN (GP41) |
| 2GSI | IG | 200605 | THERMONUCLEASE,THERMONUCLEASE,THERMONUC |
| 2HFG | CB3S | 200611 | TUMOR NECROSIS FACTOR RECEPTOR SUPERFAMIL\ |
| 2IGF | B1312 | 199204 | Myohemerythrin; residues: 69-87 |
| 2IPU | IGG2A FAB FRAGMEN. | 200710 | ABETA 1-8 PEPTIDE,Acetamide,Acetamide,Acetamide... |
| 2R0Z | IGG2A FAB FRAGMEN. | 200710 | GRIP PEPTIDE FRAGMENT |

Figure 3c.

| PDB Code | IMGT Name | Rias | Ligand |
|---|---|---|---|
| 1A0Q | 29G11 | 199905 | Phenyl[1-(N-Succinylamino)Pentyl]Phosphonate |
| 1A3L | 13G5 | 199902 | 1-Carboxy-1'-[(Dimethylamino)-Carbonyl]Ferrocene |
| 1A4K | 39-A11 | 199805 | [4-(4-Acetylamino-Phenyl)-3,5-Dioxo-4-Aza-Tricy... |
| 1BAF | An02 | 199401 | N-(2-Amino-Ethyl)-4,6-Dinitro-N'-(2,2,6,6-Tetra... |
| 1C12 | M02/05/01 | 200001 | Trazeolide |
| 1C1E | 1E9 | 200010 | 1,7,8,9,10,10-Hexachloro-4-Methyl-4-Aza-Tricycl... |
| 1CBV | Bv04-01 | 199401 | Trinucleotide TTT |
| 1CF8 | 19A4 | 199909 | 4-{4-[2-(1A,7A-Dimethyl-4-Oxy-Octahydro-1-Oxa-4... |
| 1CT8 | 7C8 | 199911 | [4-(2,2,2-Trifluoro-Acetylamino)-Benzyl]-Phosph... |
| 1DBB | Db3 | 199310 | Progesterone |
| 1EAP | 17E8 | 199412 | Phenyl[1-(N-Succinylamino)Pentyl]Phosphonate |
| 1EHL | 64M-2 | 200102 | DNA DT(6-4) photoproduct |
| 1F3D | 4B2 | 200009 | 2-(4-Aminobenzylamino)-3,4,5,6-Tetrahydropyridi... |
| 1FLR | 4-4-20 | 199509 | 2-(6-Hydroxy-3-Oxo-3H-Xanthen-9-yl)-Benzoic Acid |
| 1I3G | AL2 | 200112 | 2-Methyl-2,4-Pentanediol |
| 1IBG | 40-50 | 199505 | Ouabain |
| 1IGJ | 26-10 | 199410 | Digoxin,Digoxin |
| 1JGL | 57-2 | 200110 | Estradiol |
| 1JGU | 1D4 | 200112 | (2-Amino-3-Phenyl-Bicyclo[2.2.1]Hept-2-yl)-Phen... |
| 1KFA | 4-B8(8)/E9 | 200209 | Gibberellin A4,Gibberellin A4 |
| 1L7S | 77 | 200210 | Testosterone |
| 1LO0 | 9D9 | 200206 | 3-{[(9-Cyano-9,10-Dihydro-10-Methylacridin-9-yl... |
| 1MEX | 29G12 | 200309 | 4-(2-DIMETHYLCARBAMOYL-PHENYLCARBAMOYLC |
| 1MH5 | MS6-164 | 200309 | N-{[2-({[1-(4-CARBOXYBUTANOYL)AMINO]-2-PHENYL |
| 1MJ7 | MS5-393 | 200309 | N-{[2-({[1-(4-CARBOXYBUTANOYL)AMINO]-2-PHENYL |
| 1MJJ | MS6-12 | 200309 | N-{[2-({[1-(4-CARBOXYBUTANOYL)AMINO]-2-PHENYL |
| 1MRD | Jel 103 | 199502 | |
| 1N7M | 7G12 | 200303 | N-Methylmesoporphyrin |
| 1NCW | 4C6 | 200305 | Benzoic Acid |
| 1Q72 | M82G2 | 200308 | Cocaine |
| 1RUP | IMMUNOGLOBULIN IG. | 200403 | Benzoic Acid |
| 1SEQ | MONOCLONAL ANTIBO. | 200503 | Isopropyl Alcohol |
| 1T66 | 9-40 | 200405 | 2-(6-Hydroxy-3-Oxo-3H-Xanthen-9-yl)-Benzoic Aci... |
| 1UB5 | 19G2 | 200404 | 4-(4-Styryl-Phenylcarbamoyl)-Butyric Acid,4-(4-... |
| 1XF2 | DNA-1 | 200504 | 5'-D(*TP*TP*T)-3' |
| 1YEE | D2.5 | 199710 | 4-Nitro-Benzylphosphonobutanoyl-Glycine |
| 1YEJ | D2.3 | 199912 | 6-{4-[Hydroxy-(4-Nitro-Phenoxy)-Phosphoryl]-But... |
| 1YNL | NC6.8 | 200508 | 2-(2-Hydroxy-1,1-Dihydroxymethyl-Ethylamino)-Et... |
| 25C8 | 5C8 | 199907 | N-Methyl-N-(Para-Glutaramidophenyl-Ethyl)-Piper... |
| 2AJV | 7A1 | 200602 | Cocaine |
| 2C1P | ENA11HIS | 200601 | Fluorophenyl-hydroxy-triazol-yl-propyl-benzonit... |
| 2DDQ | R310 | 200607 | PENTYLTETRAHYDROFURAN-HISTIDIN |
| 2DQU | 6D9 | 200606 | [1-(3-Dimethylamino-Propyl)-3-Ethyl-Ureido]-[4-... |
| 2G2R | 11G10 | 200612 | NITRO-STILBENYL-METHYL-AMINO-PENTANOIC ACI |
| 2OK0 | Fab ED10 DNA compl | 200706 | 5'-D(*TP*C)-3' |
| 2PCP | 6B5 | 199901 | 1-(Phenyl-1-Cyclohexyl)Piperidine,1-(Phenyl-1-C... |
| 43CA | 43C9 | 199908 | P-Nitrophenol,P-Nitrophenol,P-Nit... |

```
              12345678901234567890123456789ABCDEF12345678901234567891    23456789 0123456    789012345678901234567890123    45678901234567
        1A3R  EIVMTQSPSSLVTPTGEKVTMTCKSSQSLLSTGKNFLAWLQKPGQSPKLLIYRA       SIRESGVP DRFSGS    SGTDFTLSISGVQAEDLAVYYCQN       FLTFGAGTKLELK
        1A...  DIVMTQSPASLVVSLGQRATISCRASETVGSCK   ELMWAYQQKPGQ-KVTYIA     SNLFSGVP AR-CSSG    SRTLFT TIRPVSA-DAAIYYCQQ      TRTFGAC K SM
        1F4X  DIQMTQTPSSLSASLGDRVTISCRASQDIS      HRINFDQKPDTVKLLIY        STHLDGVP GS NGSG   SGTLYS TISHSEPFDAFYPG CA       TSIFGSGTK AIK
        1F58  DIVLTQSPASLAVSLGQRATISCKASQGVDF    SFMNWYQQKPGQPPKLLIFAA      STLESGIP AGSFRG    SGTDFTLNIHPVSEPDAAIYYCQQ      LLFGAGTKLELK
        1F90  DVQMTQTPLTLSVTIGQPASISCESSQSILSE    TRNWLLQRPGQSPKRLLIYLV     SKLDSGVP DRFTGSG    SGTDFTLRISRVEAPDLGVYYCVQ      TIRTFGGGTKLEIK
        1FRG  DIVMTQSPSSLVTAGEKVTMSCKSSQSLFSCKRKNFLTWHQKPGQPPKLLIYAA       STRFSGVP DRFSGSG   SGTDFT TTSVQAPDLAIYYCQN         FTLFGAGTK  K
        1GGI  DIVLTQSPGSLAVSLGQRATISCRASPSVDDDGN  SFLDWYQQKPGQPPKLLIYNS     SNLISGIP DRFSGSG    SRTDFT TINPVSAJDVAIYYCQQ NR   PLTFGAGTK HIK
        118K        LTCSPASLSVATGEKVTIRCMISTDID   DVMNWYQQKPGEPPKFLISNG    NTLRDGVP DRFSGSR    TGTDFVSTIENTLSEDVGDYYCIK     EPLTFGCGTKLEI
        1ITFH  DIVMTQSPSSLIVTAGEKVTMSCTSSQSLFNSGKQKNYLTWYQQKPGQPPKVLIYAA    STRFSGVP DRFTGSG    SGTDFT TISSVQAPDLAVYYCQN      FLTFGGGTK RLK
        1KC5  DIVLTQSPKSMSMSVGERVTLSCKASENVD      EGVAWYQQRPEQPPALLIYCA     SNRYTGVP DRLTGSG    SATDFTLTISHVQAEDLADYHCGQ     SPLIFGGGTKLELK
        1KCS  DIVMTQSPKSMGMSVGEAVTLNICKASENVG     IYVSWYQQKPGQSPVLLLYCA     SNRYTGVP DRFTGSG    SATDFTLTISSVQADDDADYYCGQ      PLIFGGGTKLELK
        1KTR  DILMTQTPSSLPVSLGDQASISCRSSQSIV     NTLSWLQKPGQSPDKLLIYKV      SNRFSGVP DRFSGSG    SGTDFTLKISRVEAPDLGVYYCFQ      PFTFGGGTK LEIK
        1MPA  DIVMTQTPLSIPVSIGDKASISCRSSQAIVSN    TRIEWYLQKPGQSPKLLIYKV     SNRFSGVP DRFSGSG    SGTDFTLKISRVEAEDLGIYYCFQ      FTIFGGGTKLEIK
        1MVU  DIVMTQSPSSLIVTAGEKVTMSCKSSQSLLNSGNQKNFLTWYQKNQSPKLLIYAA       STRESGVP DRFSGSG    SGTDFTLTISSVQAEDLAVYYCQND     DLTFGAGTKLEP
        1NOX  SIVLTCSPGTLSLSPGERATFSCRSS         VANYQHKIGQAPRLVIHCV       SNRASHIS DSFSGSG    SGTDFTLTITRVEPEDFALYYCOVY      YLFGGGTKLERK
        1NAK  DVVMTCSPVG PVSIGDQASISCRSSQSIGHSSGN TAFIQKPGQSPKLLITYV       SNRFSGVP DRFSGSG    SGTLFFZISRVEAPD GVYYFQ        DSLFGGGTKRIK
        1PZ5  PVVLTQTFLSLPVRIGDQASISCRSSQSIL    INTLAWIQKPGQSPKLLIYRV      SNRFSGVP DR-SGSG   SGTDFTI KISRVEAPDLGVYYFQSG      FFGGGTKRIK
        1SVZ  LILMTQTPLYLPVSLGDQASISCRSSQTIVDNGN   TYLEWYLQKPGKPGQSPQDLIYKV  SNRFASVP DRFSGSG    SGTDFTLKISRVEAEDLGIYYCFQ      PPTFGGGTKLEI
        1T7T  DIVMTQTPLSLPVSIGDQASISCKQSQSIVHISN   IESAYLQKPCQSPKLLIYKV     SNRFSGVP LR-CGSG    SGTDFTLKISRVEAPDLGVYYC Q      IPSFFGGGTK RIK
        1XGY  DIVMTQAAFSNPVTIGTSASICRSSKSILHSNGI  TNKYLQRFGQGFCLLIYM        SNLADGVP DRFCGSG    SGTDFAFRISRVEAPDVGVYYCGQ       IFFGTGFTK RIK
        2A61  DIQMTQTISSLSASLGDRVTISCRASPQIR       NYLNWYQQKPDNTVKLLIYYT    SRLHSGVP DRFSGSG    SGTDYGTTHNLEPEDIATYFHCQCNT    LPHTFGGGTKLELK
        2CK0  DIQLTQSPSLAVSAGEKVTMNCKSSQNLLRSICRKNYLAWYRQKPGQSPKLLIYAA       STRGSGVP DRFTGSG    SGTDFTLTISSVQAPDLAVYYCKQ       YTFGGGTKLEIK
        2HX7  EIVITCQSPGTQSLSPGERATLSCRASOSVCL    NIDAWYQRPCQAPRLLIYCA      SSRPSGVA DAFSGSG    SGTDFTLTIERLASTD.AVYYCQG     FFGGCTKVVK
        2QST  DIVITQSPASLAVSLGQPATISLGASKUVRIEY   SLMDAWQQKPCQPPRRLYYV      SNRFSGVP AR-SCSG    SGTDFT NTHPVSPDAAIYYCSL      PLSGGGTKLELK
        2HPG  DIDMTQSPSSLSASVGDRVTIDRASQDVS       TAVAWYQQKPDKAPKLLISSA    SFLYSGVP SAFSGSG    SGTDFTLTISSCLPEDIATYYCQQTI    DLIFGGGTKVELK
        2IGF  DVLMTQSPLSLPVSLGDQASISCRSSNQTILLSRG  TRLEWYLQKPGQSPKLLIYKV    SNRFSGVP DRFSGSG    SGTDFTLKISRVEAPDLGVYYCFQG    VPFFGGGTKMRI
        2IPU  DVLMTQTPLSLPVSLGDQASISCRSSOSIV    NTLAEYLQKPGQSPKLLIYKV     SNRFSGVP DRFSGSG    SGTDFT KISRVEAFDLGVYYCFQG    FFGACTKHIK
        2ROW  DVLMTQTPLSLPVSLGDQASISCRSSQSI  GN   TNLEWYLQKPGQSPKLLIYKV    SNRFSGVP DRFSGSG    SGTDFT KISRVEAFDLGVYYCFQG   PLTFGGGTKMIK
        2ROZ  DVLMTQTPLSLPVSLGDQASISCRSSQSI IGN   TNLEWYLQKPGQSPKLLIYKV    SNRFSGVP DRFSGSG    SGTDFTLKISRVEAEDLGVYYCFQG   PLTFGAGTKLELK
```

```
2E0Q  DVLMTQTPLSLPVSLGDQASISCRSSQSIVHSNGN TYLEWYLQKPGQSPKLLIYKV   SNRFSGVP DRFSGSG   SGTDFTLKISRVEAEDLGVYYCFQG   VPLTFGAGTKLELK
2E0U  DVLMTQTPLSLPVSLGDQASISCRSSQTIVHSGD  TYLDWFLQKPGQSPKLLIYKV   SNRFSGVP DRFSGSG   SGTDFTLKISRVEAEDLGVYYCFQG   VPLTFSGGTKLEI
2G2R  DVVMTQSPLSLPVTLGQPASISCRSSQSLVYSDGN THYLNWLQRPGQSPRLLIY V    SRLDSGVP DRFSGSG   SGTDFTLKISRVEAEDVGVYFCMQA   LQLPGAGTKLELK
2OK0  DILMTQTPLSLPVSLGDQASISCRSSQSIVHSNGN TYLEWYLQKPGQSPTLLIYKV   SNRFSGVP DRFSGSG   SGTEFTLKISRVEAEDLGVYYCFQG   IPLTFGAGTKLEVK
2PCP  DVLMTQTPLSLPVSLGDQASISCRSSQTIVHSNGN TYLEWYLQKPGQSPKLLIYKV   TNRFSGVP DRFSGSG   SGTDFTLKISRVEAEDLGVYYCFQG   ASLTFGDGTKLEIK
4JCA  DVVMTQTPSSLAMSVGQKVTMSCKSSQSLLNSNQKNYLAWYQKHPGQSPKLLVYLA    STRESGVP DRFTGSG   SGTDFTLTISSVQAEDLQAIYYCQQHYR  APYTFGGGTKLEIK
```

```
       123456789 012345678901234567890lAB  234567890123456789012ABC345678901234  567890123456789012ABC345678901234  1234567890123
1VHM   EVKLEESGG GLVQPGGSMKLSCAASGFTFS     MDYVRQSPKRGLEWVAAIRNKVNNHATHYAESVK    RFTVSRDDSKSSVYLQMNSLRAEDTGIYYCSG   LYWRQGTLVTVSA
1KTJ   EVQLQSSGA ELVKPGASVKISCTASGFNIK     MDWVKQRPEKGLEWIGEIFP  ASGTTKYDPKFQ   DKATLTADTSSNTAYLQLSSLTSEDTAVYYCAC   DYWGQGTTITVSS
1YQV   EVQLQESGA ELMKPGASVKISCKASGYTFS     MTWVRQRGHGLEWIGLTLP  GSGGTYNERFK    GKATITADTSSSTAYMQLNCLTSEDSGVYYCAR   DGAGQGTTITVSS
1ZTX   QVQLQQSGS ELMKPGASVQISCKATGYTIS     LEAVKQRPGHGLEWIGDILC  GTGGTYNEKLK   AMAIFTADTSSNIAFMQLSSLTSEDSAVYYCAR   DYWSHGTTITVSC
2ADF   QIQLVQSGP ELKKPGETVKISCKASGYTFI     MNWVRQAPGKGLKWMGWKF   IGETIYGEEFR   GRFAFSLETSVSTAYLQINNLKNFDTATYFCAR   DYWGQGTTVTVSS
2AEP   EVKIVESGG GLVQPGGSLSLSCATSGFTFID    YSMSWFRQPGKA PWIGLIP  SYGMYGASLK    GRFTISRDNSCSIVYLHMNTLTAPDSATYYCAR   LYWGQGTTITVSS
2HJN   EVQLQQSGA ELVKAGASVKLSCPASGLNP      MHWVKQRPEQGLEWIGRIDP  SNGNTKFDPKFQ  GKATITADTSSNTAYLQLSSLTSPDTAVYYCAR   HWAGQGTTITVSS
2BRR   VQLEQSGP  ELKKPGETVKISCKASGYTF      AIVKQAPGKGLKWMG       TGEPIYADDFK   RFSAPSLETSASAAYLGINNLKNEDTAIYFCAR   DYWGQGTTVTVSS
2CMR   QLVQSGA   EVRKPGASVKVSCKASGDTFS     AISWVRQAPGQGLEWMG     YAQAFQ        GRVTITAHESTGTAYMELSSLRSFDTAIYYCAR   DYWGAGTLVTVSS
2DQC   DVQLQESGP SLVKPSQTLSLTCSVTGDSIT     WSWIRKFPGNRLRYMGAVI    TYNPSLK      SRISICRDTSKNQYYLDLNSVTPDTATYYCAR   GYWGQGTLVTVSA
2FD6   VKLQQSGP  EVVKPGASVKISCKASGYSFTM    THNWVRQPGQGLEWIGMIFH  GSGGKYNEKFK   DKATLTADTSSSTAYMQLSSLTSPDSAVYFCAR   TVAGQGTTVTVSS
2FJG   EVQLVESGG GLVQPGGSLRLSCAASGFTIS     WTHWVRQAPGKGLEWVAGI   KVGGYTTHYGPSVK GRFTISADTSKNTAYLQMNSLRAEDTAVYYCAR   DYWGQGTLVTVSS
2G5B   EVNLVESGG GLVQPGGSLRLSCATSGFTFID    MMGWVRQPPGKALEWLGFI   KVGGYTTHYGPSVK GRFTISRDDSQSILYLQMNTLRTEDSATYYCVR   DVWGAGTTVTVSS
2GHW   EVQLVQSGG GVVQPGKSLRLSCAASGFAFS     MHWVRQAPGKGLEWVAV      DGSHSYADSVK  GRFTISRDNSKNTLYLQMNSLRAEDTAVYYCAR   MYWGQGTLVTVSS
2HJF   QVQLQQPSA ELVKPGASVKLSCKASGYTFS     MHWVKQRPGHGLEWIG IIP  SSGGAYNYKIQ   KKATLTADKSSSTAFMQLSSLTSEDSAVYYCAR   AVAGAGTTVTVSS
2HKF   EVQVVESGG GLVQPKGSLKLSCVVS MLNY     MNAVRQAPDGKGLEWVA     KGNYATYYADSVK DRFTISRDDSQSMIYLQMNNLKTEDTAMYYCVT   AMWGQGTLVTVSA
2HHI   QIQLKESGP GILVQPSQPFR IGTPSGPSI     QVTW HQPSCKGLFNLATIW   WDDDSKYNPS K  SRITVSKDTCSNQAPS M VTADTATYYCAC    HWAGQGTSVTVSS
2HRP   DVQLVESGG GLVQPGGSRKLSCAASGFTIMR    PGMRAVRQABEKGLEWVAHI S GSSGTLYADTVK GRFIISRDNPKNTLPLQMISLRSEDTALYYCAR   LYWGQGTSVTVSS
2IVK   QVQLQQPSA ELVKPGASVKLSCKASCYTF      DITHWVKQRPGHGLEWIG IIP SGNAGYNHKIQ  KKATLTADKGSSTAFMQLSSLTSEDSAVYYCAR   AVAGAGITVTVSS
2IBZ   EVKIQFSGA GLVQPSQSLSITCTVSVGL G     YWNWIRLFPGNKLFWVGYIR  NVSDNNYNPSLK DRLFITRDTSKNQFFLXLNSVTFDTATYYCAR   WAGQGTTVTVSS
2IH3   QVQLQQPGA ELVKPCASVKLSCKASCYTF      DIT HVKQRPGHG FWIG IIP KKATITAGGYNHKIQ KAATITAHKSSSTAFMQLSCLTSFDSAVYYCAR AVAGAGITVTVSS
2KKW   EVQLVESGG GLVRPGGSLKLSTAASGFIFS     HGMAVRQTPDEKRLEWVAHI S LTYVESVK     GRFTISRDNAKNNLYLQMSFLRSEDSAIYYCAR  GYWGQGTLVTVF
2IFL   QVQLAQSGP ELVRPCVVRISCKGSCYT        MHWVKQSHAKGFEWIGL      LITYNQKFK    GRATMTVEKSSSTAYME ARFTSPDSAIYYCAR   DYWGAGTTVTVSS
2NYI   EVQIVECSA EVKPGGSVRVCTKSGDFTR       YSFTAVRQAFGQGLFWWSRTT  ILDVANYAPHLQ GRVTITAIKSCTVYLERNTRDDTAVYPCAG      KHWSGQGTLVTVS
2QZ4   EVQLQQSGP ELVQPGANVKISVKTSCYTF      MAVKQSRCKSLEWIGMI     MWNYKIS I     DKATLTVDKSSSIAYMENCLTSEDSAVYY AI    AYKLPGILVTVSA
2UZ1   EVQLFCCG  GLVQPCCGTRISLDAASCFIST    FSMNAVRQAFCKGIFWVSYIUR TGKTIYYADGVK GRFTISRINGKNTLYLQVNSFHAKDTAVYYCAR   YWGOGTLVTVS
```

```
        123456789 012345678901234567890lAB  234567890123456789012ABC345678901234  567890123456789012ABC345678901234  1234567890123
2OK0    EVQLEESGP ELVKPGASVKISCKASGYTFTD    YMHWLRQKPGQGLEWIGWV                   YPGSIKYNEKFK DKATLTADTSSSIVYMEL SCITSDDNAVYFCTR   DYWGRGTLVTVSS
2PCP    PVQLQQSGP ELVKPGASVKMSCKASGYTFTD    YYIHWMKQSHGKSLEWIGYIYP                NNGGNGYNEKFK GKATLTVDKSSSTAYMDVRT TSEDSAVYYCGH      DYWGQGTTLTVSS
43CA    QVQLVESGP GLVAPSQSLSITCTVSGISLSR    YNVHWVRQSPGKGLEWLGMIW                 GGGSIEYNPALK SRLSISKDNSKSQIFLKMNSLQTDDSAMYYCVS    SYWGQGTLVTVS
```

Figure 7A.

| SDR | Chothia residue | rSDRU | % Amino acid frequency at each rSDRU position | | | | | | | | | | | | | | | | | | | Amino acid representation | | |
|---|---|---|---|---|---|---|---|---|---|---|---|---|---|---|---|---|---|---|---|---|---|---|---|---|
| | | | A | R | N | D | C | Q | E | G | H | I | L | K | M | F | P | S | T | W | Y | V | No cutoff | 5% cutoff | 10% cutoff |
| L1 | 27 | L | | | | | | 71 | 28 | | | | | | | | | | | | | | QE | QE | QE |
| | 28 | L | 16 | | 16 | 50 | | | | | | | | | | | | 16 | | | | | ANDS | ANDS | ANDS |
| | 30 | M | | | 8 | | | | | 16 | 8 | | | 8 | | | | 36 | | | 24 | | NGHKSY | NGHKSY | GSY |
| | 30A | L | | | | 16 | | | 33 | | | | | | | | | 33 | | | 16 | | DHSY | DHSY | DHSY |
| | 30B | L | | | | | | | 33 | | | | | | | | | 33 | | | 33 | | GSY | GSY | GSY |
| | 30C | L | | | 50 | 25 | | | 25 | | | | | | | | | | | | | | NDG | NDG | NDG |
| | 30D | L | | | | 33 | | | 66 | | | | | | | | | | | | | | DG | DG | DG |
| | 30E | L | | | 50 | | | | | | | | | 50 | | | | | | | | | NK | NK | NK |
| | 30F | | | | | | | | | | | | | | | | | | | | | | | | |
| | 31 | M | | | | 50 | | | | | 5 | | | | | | | 30 | 15 | | | | NHST | NHST | NST |
| | 32 | H | 2 | 6 | 18 | 4 | | | | | | | | | | 4 | | 4 | | 4 | 54 | | ARNDFSWY | RNY | NY |
| | 34 | L | | | | 16 | | | | | 16 | | | 16 | | | | | | | 50 | | NHFY | NHFY | NHFY |
| L2 | 49 | M | | | | | | | 4 | | 9 | | | 22 | | | | 4 | | | 59 | | EHKSY | HKY | KY |
| | 50 | H | 2 | | | 5 | 2 | | 2 | 5 | | | 5 | 5 | | 2 | | 5 | | 5 | 52 | | ANDQGLKFSWY | NGLKSWY | Y |
| | 53 | M | | 15 | 5 | | | 25 | | | | | | 10 | | | | 5 | 30 | | 10 | | RNQFSTY | RNQFSTY | RQFTY |
| | 55 | L | | | | 14 | | 14 | 28 | | 28 | | | | | | | 14 | | | | | DQEHF | DQEHF | DQEHF |
| | 56 | L | 10 | | | | | | 10 | | | 10 | | | | | 20 | 40 | 10 | | | | AEIPST | AEIPST | AEIPST |
| L3 | 91 | H | | | 2 | 4 | 2 | | | 8 | 8 | | | | | 13 | | 33 | | 6 | 20 | | RNDGHFSWY | GHFSWY | FSY |
| | 92 | H | 2 | | 27 | 4 | | 4 | 2 | 12 | 2 | | 2 | | | 2 | | 12 | 2 | 10 | 12 | 2 | ANDQEGHLFSTWYV | NGSWY | NGSWY |
| | 93 | H | | 9 | 3 | | | | 15 | | 6 | 3 | | 3 | 3 | | | 39 | 15 | | | 3 | RNEHIKMSTV | REHST | EST |
| | 94 | H | | | 2 | 2 | 2 | | | | 5 | 2 | 7 | | | 7 | 5 | 15 | 2 | 25 | 15 | 5 | RNDHILFPSTWYV | HLFPSWYV | SWY |
| | 95 | L | 14 | | | | | | | | | | 14 | | | 14 | 42 | | 14 | | | | ALFPT | ALFPT | ALFPT |
| | 96 | H | | | 14 | | | | 2 | | | 2 | | | 2 | 11 | 8 | | | 29 | 26 | | RQIMFPWY | RFPWY | RFWY |

Figure 7B.

| SDRR | Chothia residue | rSDRU | % Amino acid frequency at each rSDRU position ||||||||||||||||||| Amino acid representation |||
|------|------|------|---|---|---|---|---|---|---|---|---|---|---|---|---|---|---|---|---|---|---|-----------|-----------|------------|
|      |      |      | A | R | N | D | C | Q | E | G | H | I | L | K | M | F | P | S | T | W | Y | V | No cutoff | 5% cutoff | 10% cutoff |
| L1 | 30 | M |  | 20 |  | 20 |  |  |  |  |  |  |  |  |  |  |  |  |  |  |  | 60 | RDV | RDV | RDV |
|    | 30A | H |  |  | 25 |  |  |  |  |  | 50 |  |  | 4 |  | 8 |  | 4 |  |  | 8 |  | NHFSTY | NHSY | NH |
|    | 30B | M |  |  |  | 12 |  |  |  |  |  |  |  |  |  |  |  | 62 |  |  | 25 |  | DSY | DSY | DSY |
|    | 30C | M |  | 6 | 62 | 12 |  |  |  | 6 |  |  | 6 |  |  |  |  | 6 |  |  |  |  | RNDGKS | RNDGKS | ND |
|    | 30D | L | 16 |  | 16 |  |  |  |  | 16 |  |  | 16 |  |  |  |  |  | 33 |  |  |  | ANGKT | ANGKT | ANGKT |
|    | 30E | M |  |  | 60 | 20 |  |  |  |  |  |  |  | 20 |  |  |  |  |  |  |  |  | NDK | NDK | NDK |
|    | 30F |   |  |  |  |  |  |  |  |  |  |  |  |  |  |  |  |  |  |  |  |  |  |  |  |
|    | 32 | H |  | 2 |  | 2 |  |  |  |  |  |  | 5 |  |  | 14 |  |  |  | 2 | 71 |  | RDKFWY | FY | FY |
|    | 34 | M |  |  | 12 |  |  |  | 12 | 25 |  |  |  |  |  |  |  | 12 | 25 |  | 12 |  | NEHSTY | NEHSTY | NEHSTY |
|    | 36 | L |  |  |  |  |  |  |  |  |  |  |  |  |  |  |  |  |  |  | 100 |  | Y | Y | Y |
| L2 | 49 | L |  |  |  |  |  |  |  |  |  |  |  |  |  |  |  |  |  |  | 100 |  | Y | Y | Y |
|    | 50 | M |  | 23 |  |  |  |  | 7 | 7 |  |  |  | 30 |  |  |  |  |  | 15 | 15 |  | REGKWY | REGKWY | RKWY |
| L3 | 89 | L |  |  |  |  |  | 75 |  |  |  |  |  |  |  | 25 |  |  |  |  |  |  | QF | QF | QF |
|    | 91 | H |  |  | 5 | 8 |  |  |  | 30 |  | 2 | 5 |  | 2 |  |  | 27 | 8 |  | 8 |  | NDGILMSTY | NDGLSTY | GS |
|    | 92 | H |  | 2 | 2 |  |  |  |  | 11 | 5 |  | 2 | 2 |  | 2 |  | 26 | 14 |  | 26 |  | RNGHLKFSTY | GHSTY | GSTY |
|    | 93 | H | 7 | 3 | 7 |  |  |  | 7 | 18 | 29 |  |  |  |  | 3 |  | 22 |  |  |  |  | ARNQEHFS | ANQEHS | EHS |
|    | 94 | H |  |  | 8 | 8 |  |  |  |  | 8 | 5 | 2 |  |  | 11 |  | 14 |  |  | 14 | 23 | NDHILFSYV | NDHIFSYV | FSYV |
|    | 95 | L |  |  |  |  |  |  |  |  |  |  | 57 |  |  |  |  | 14 |  |  | 14 | 14 | LSYV | LSYV | LSYV |
|    | 96 | L |  | 11 |  |  |  |  |  |  |  | 2 |  | 37 |  | 11 | 17 | 5 |  | 2 | 11 |  | RHLFPSWY | RLFPSY | RLFPY |

Figure 7c.

| SDRR | Cothia residues | rSDRU | Amino acid frequency ||||||||||||||||||||| Amino acid representation |||
|------|-----------------|-------|---|---|---|---|---|---|---|---|---|---|---|---|---|---|---|---|---|---|---|---|-----------|-----------|------------|
| | | | A | R | N | D | C | Q | E | G | H | I | L | K | M | F | P | S | T | W | Y | V | No cutoff | 5% cutoff | 10% cutoff |
| L1 | 30A | M | | | | | | | | | 76 | | | | | | | 5 | | | 17 | | HTY | HTY | HY |
| | 30B | L | | 25 | | | | | | | | | | | | | | 75 | | | | | RS | RS | RS |
| | 30C | L | | | 100 | | | | | | | | | | | | | | | | | | N | N | N |
| | 30E | L | | | 100 | | | | | | | | | | | | | | | | | | N | N | N |
| | 32 | M | | | | | | | | | 4 | | | 4 | | 8 | | | | | 82 | | HKFY | FY | Y |
| | 34 | M | 15 | 3 | 11 | | | | 15 | 7 | 19 | | | | | 3 | | | | | 23 | | ARNDGHSY | ANDGHY | ANDHY |
| | 36 | L | | | | | | | | | 5 | | 16 | | | 16 | | | | | 61 | | HLFY | HLFY | LFY |
| L2 | 49 | L | | | | | | | | | 20 | | | | | | | | | | 80 | | HY | HY | HY |
| | 50 | L | | | 14 | 14 | | | | | | | 14 | | | 28 | | 28 | | | | | NDKFS | NDKFS | NDKFS |
| L3 | 89 | L | 3 | | | | | 17 | | | 7 | | 21 | | | 25 | | 7 | | | 7 | 10 | AQHLFSWV | QHLFSWV | QLFV |
| | 90 | L | | | | | | 100 | | | | | | | | | | | | | | | Q | Q | Q |
| | 91 | H | | | 4 | | | | | 31 | 11 | | | | | 4 | | 18 | 4 | 6 | 15 | 2 | NGHFSTWYV | GHSWY | GHSY |
| | 92 | M | | 5 | | | | | | | 5 | | 21 | | | | | 36 | 21 | | 5 | 5 | RHLSTYV | RHLSTYV | LST |
| | 93 | L | | | | | | | 35 | 14 | 42 | | | | | | | | 7 | | | | EGHT | EGHT | EGH |
| | 94 | L | | 4 | | | | | | | | 4 | 9 | | | 18 | 4 | | | | 27 | 31 | RILFPYV | LFYV | FYV |
| | 96 | M | | 5 | | | | | | | | 2 | 20 | | | 12 | 25 | | | 7 | 27 | | RILFPWY | RLFPWY | LFPY |

Figure 8a.

| SDRR | Cothia residue | rSDRU | Amino acid frequency ||||||||||||||||||||  Amino acid representation |||
|---|---|---|---|---|---|---|---|---|---|---|---|---|---|---|---|---|---|---|---|---|---|---|---|---|
| | | | A | R | N | D | C | Q | E | G | H | I | L | K | M | F | P | S | T | W | Y | V | No cutoff | 5% cutoff | 10% cutoff |
| H1 | 27 | L | | | | | | | | | | | | | | | | | | | 100 | | Y | Y | Y |
| | 28 | L | | | | | | | | | | | | | | | | | 20 | 80 | | | | ST | ST | ST |
| | 30 | H | | | | | | | | | | 8 | 11 | | | | | | 26 | 52 | | | | IKST | IKST | KST |
| | 31 | H | | 2 | 8 | 27 | | | 6 | 2 | | | | | | | | | 31 | 21 | | | | RNDEGST | NDEST | DEST |
| | 31A | H | | | 25 | | | | | | | | | | | | | | 50 | | | 25 | | NSY | NSY | NSY |
| | 31B | | | | | | | | | 100 | | | | | | | | | | | | | | G | G | G |
| | 32 | H | 5 | | | 12 | | | | | | | 2 | | | 5 | | 5 | 7 | | | 61 | | ADLFSTY | ADFSTY | DY |
| | 33 | H | 9 | | | 2 | | | | 9 | | | | | 2 | 2 | 7 | 2 | 28 | 35 | | | | ADGFPSTWY | AGSWY | WY |
| | 35 | M | | | 14 | | | 21 | | 42 | | 7 | | 7 | | | | | | | | 7 | | NEHKFY | NEHKFY | NEH |
| H2 | 50 | H | | 2 | 2 | | | 22 | 5 | | | 8 | | 2 | | | | 2 | 5 | 20 | 22 | 2 | | RNEGLMSTWYV | EGLTWY | EWY |
| | 51 | L | | | | | | | | | | 87 | | 12 | | | | | | | | | | IF | IF | IF |
| | 52 | H | 2 | 4 | 16 | 14 | | | | | 2 | 8 | 12 | | 4 | | | | 16 | 2 | 12 | 4 | | ARNDHILFSTWY | NDILSW | NDLSW |
| | 52A | M | | 5 | 5 | 11 | | | | | | | | | | | 29 | 5 | 35 | | | 5 | | RNDPSTY | RNDPSTY | DPT |
| | 52B | | | | | | | | | | | 100 | | | | | | | | | | | | K | K | K |
| | 52C | | | | | | | | 50 | | | | | | | | | | | | | 50 | | GV | GV | GV |
| | 53 | H | 10 | | 12 | | | 7 | 12 | 2 | 7 | | | 5 | | | | 10 | 2 | 7 | 22 | | | ANEGIFSTWY | ANEGIFSWY | ANGSY |
| | 54 | H | 2 | | 13 | 24 | | 2 | 2 | | | 2 | | 2 | | | | 32 | 5 | | 8 | 2 | | ANDQGLFSTYV | NDSY | NDS |
| | 55 | M | | | | 14 | | | | 78 | | 7 | | | | | | | | | | | | DGK | DGK | DG |
| | 56 | H | | 10 | 18 | 7 | | | 5 | 5 | 2 | | | 2 | | | | 21 | 7 | | 15 | 2 | | RNDEGHFSTYV | RNDEGSTY | RNSY |
| | 57 | M | 7 | | | | | | | | | | | | | | | 21 | 71 | | | | | AST | AST | ST |
| | 58 | H | | 8 | 17 | 2 | | 2 | 5 | | 5 | 5 | 2 | | 2 | 2 | | 5 | 2 | | | 32 | | RNDQEHILMFSTY | RNEHISY | NY |

Figure 8b.

| SDRR | Cothia residue | rSDRU | Amino acid frequency ||||||||||||||||||| Amino acid representation |||
|---|---|---|---|---|---|---|---|---|---|---|---|---|---|---|---|---|---|---|---|---|---|---|---|
| | | | A | R | N | D | C | Q | E | G | H | I | L | K | M | F | P | S | T | W | Y | V | No cutoff | 5% cutoff | 10% cutoff |
| H1 | 30 | L | | | | | | | | | | | | 40 | | | | | 60 | | | | KT | KT | KT |
| | 31 | M | | 5 | 27 | 27 | | | | | | | | 5 | | | | 16 | 16 | | | | RNDKST | RNDKST | NDST |
| | 31A | | | | 16 | 50 | | | | 16 | | | | | | 16 | | | | | | | NDGF | NDGF | NDGF |
| | 31B | | | | | 50 | | | | 50 | | | | | | | | | | | | | NG | NG | NG |
| | 32 | M | | | | | | | | 5 | | | | 5 | | | | | | 88 | | | GFY | GFY | Y |
| | 33 | M | 32 | | | | 4 | | 4 | 20 | | | | 4 | | | | | 12 | 24 | | | CEGFWY | GWY | GWY |
| | 34 | | | | | | | | | | | 28 | 28 | | 28 | | | | | 14 | | 9 | ILMW | ILMW | ILMW |
| | 35 | H | | | 45 | | | | 4 | | 22 | | | | | | 18 | | | | | 9 | NEHSY | NHSY | NHS |
| H2 | 47 | L | | | | | | | | | | | | | | | | | | | 91 | 8 | | WY | WY | W |
| | 50 | H | | 16 | | 3 | | | 6 | 13 | 6 | | | | 3 | | | | 6 | 20 | 23 | | | RDEGHFTWY | REGHTWY | RGWY |
| | 51 | L | | 8 | | | | | | | | | 75 | | | | | | | | | | 16 | RIV | RIV | IV |
| | 52 | H | | 14 | 17 | 10 | 3 | | | | | 3 | 7 | | 3 | | 17 | 3 | 10 | 7 | | | | RNDCHIFSTWY | RNDISWY | RNDSW |
| | 52A | M | | | 25 | | | | | | | | 8 | | | 16 | 16 | 33 | | | | | | NLPST | NLPST | NPST |
| | 52B | | | | | | | | | | | | | | | | | | | | | | 100 | V | V | V |
| | 52C | | | | | | | | | 100 | | | | | | | | | | | | | | G | G | GWY |
| | 53 | H | | | 10 | | | | 5 | 20 | | | 5 | | 5 | | | | | 20 | 35 | | | NEGLFWY | NGLFWY | NGWY |
| | 54 | H | | | 17 | 29 | | | 5 | 23 | | | 11 | | | | 5 | 5 | | | 25 | | | NDEGLST | NDEGLST | NDGL |
| | 55 | M | | | | | | | | 50 | | | | | | | | | 25 | | | 25 | | GSY | GSY | GSY |
| | 56 | H | 5 | | 10 | 35 | | | | 10 | | 10 | | | | | | | 5 | 5 | | 20 | | SNDGISTY | SNDGISTY | NDGIY |
| | 57 | L | | | | | | | | | | | | 16 | | | | | | 83 | | | | KT | KT | KT |
| | 58 | H | 4 | 12 | 20 | | | | 12 | | 4 | | | 4 | | 4 | | 12 | 4 | | 20 | | | ARNEHKFSTY | RNESY | RNESY |

Figure 8c.

| SDRR | Chothia residue | rSDRU | \multicolumn{20}{c|}{Amino acid frequency} | \multicolumn{3}{c|}{Amino acid representation} |
|---|---|---|---|---|---|---|---|---|---|---|---|---|---|---|---|---|---|---|---|---|---|---|---|---|---|
| | | | A | R | N | D | C | Q | E | G | H | I | L | K | M | F | P | S | T | W | Y | V | No cutoff | 5% cutoff | 10% cutoff |
| H1 | 30 | L | | | | | | | | | | | | | | | | | | | | | | | |
| | 31 | L | | | 14 | 42 | | | | | | | | | | | | 28 | 14 | | | | NDST | NDST | NDST |
| | 32 | L | 12 | | 12 | | | | | | | | | | | | | | | | 75 | | ANY | ANY | ANY |
| | 33 | M | 35 | | | | | | | 12 | | 3 | | | | | | | | 25 | 16 | 6 | AGIWYV | AGWYV | AGWYV |
| | 35 | H | | | 41 | | | 2 | 2 | 2 | 35 | | | | | | | 14 | | | | | NQEGHS | NHS | NHS |
| H2 | 47 | M | | | | | | | | | | | 4 | | | | | | | 90 | 4 | | LWY | L | L |
| | 50 | M | | 10 | 3 | 3 | | | 6 | | | 3 | | 3 | | | | 16 | 3 | 16 | 30 | 3 | RNDELMST | RESWY | RSWY |
| | 52 | M | | 27 | 9 | | | | | | | | | | | | | 18 | 9 | 9 | 9 | 18 | RNSTWYV | RNSTWYV | RSV |
| | 53 | L | | | 28 | | | | | | | | | | | | | | 14 | | 57 | | NTY | NTY | NTY |
| | 58 | L | | 12 | | | | | | | 12 | | | | | | | 12 | | | 50 | 12 | RHSYV | RHSYV | RHSYV |

SEQUENCE LISTING

<160> NUMBER OF SEQ ID NOS: 286

<210> SEQ ID NO 1
<211> LENGTH: 102
<212> TYPE: PRT
<213> ORGANISM: Mus musculus

<400> SEQUENCE: 1

Asp Ile Glu Leu Thr Gln Thr Thr Ser Ser Leu Ser Ala Ser Leu Gly

```
                1               5                  10                 15
Asp Arg Val Thr Ile Ser Cys Arg Ala Ser Gln Asp Ile Ser Asn Tyr
                20                 25                 30

Leu Asn Trp Tyr Gln Gln Asn Pro Asp Gly Thr Val Lys Leu Leu Ile
            35                 40                 45

Tyr Tyr Thr Ser Asn Leu His Ser Glu Val Pro Ser Arg Phe Ser Gly
    50                 55                 60

Ser Gly Ser Gly Thr Asp Tyr Ser Leu Thr Ile Ser Asn Leu Glu Gln
65                 70                 75                 80

Glu Asp Ile Ala Thr Tyr Phe Cys Gln Gln Asp Phe Thr Leu Pro Phe
                85                 90                 95

Thr Phe Gly Gly Gly Thr
            100
```

<210> SEQ ID NO 2
<211> LENGTH: 107
<212> TYPE: PRT
<213> ORGANISM: Mus musculus

<400> SEQUENCE: 2

```
Asp Ile Val Leu Thr Gln Ser Pro Ala Ser Leu Ser Ala Ser Val Gly
1               5                  10                 15

Glu Thr Val Thr Ile Thr Cys Arg Ala Ser Gly Asn Ile His Asn Tyr
                20                 25                 30

Leu Ala Trp Tyr Gln Gln Lys Gln Gly Lys Ser Pro Gln Leu Leu Val
            35                 40                 45

Tyr Tyr Thr Thr Thr Leu Ala Asp Gly Val Pro Ser Arg Phe Ser Gly
    50                 55                 60

Ser Gly Ser Gly Thr Gln Tyr Ser Leu Lys Ile Asn Ser Leu Gln Pro
65                 70                 75                 80

Glu Asp Phe Gly Ser Tyr Tyr Cys Gln His Phe Trp Ser Thr Pro Arg
                85                 90                 95

Thr Phe Gly Gly Gly Thr Lys Leu Glu Ile Lys
            100                105
```

<210> SEQ ID NO 3
<211> LENGTH: 108
<212> TYPE: PRT
<213> ORGANISM: Mus musculus

<400> SEQUENCE: 3

```
Asp Ile Glu Leu Thr Gln Thr Pro Val Ser Leu Ser Ala Ser Val Gly
1               5                  10                 15

Glu Thr Val Thr Ile Thr Cys Arg Ala Ser Glu Asn Ile Tyr Ser Tyr
                20                 25                 30

Leu Ala Trp Tyr Gln Gln Lys Gln Gly Lys Ser Pro Gln Phe Leu Val
            35                 40                 45

Tyr Asn Ala Lys Thr Leu Gly Glu Gly Val Pro Ser Arg Phe Ser Gly
    50                 55                 60

Ser Gly Ser Gly Thr Gln Phe Ser Leu Lys Ile Asn Ser Leu Leu Pro
65                 70                 75                 80

Glu Asp Phe Gly Ser Tyr Tyr Cys Gln His His Tyr Gly Thr Pro Pro
                85                 90                 95

Leu Thr Phe Gly Gly Gly Thr Lys Leu Glu Ile Lys
            100                105
```

<210> SEQ ID NO 4

```
<211> LENGTH: 107
<212> TYPE: PRT
<213> ORGANISM: Mus musculus

<400> SEQUENCE: 4

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 5
<211> LENGTH: 107
<212> TYPE: PRT
<213> ORGANISM: Mus musculus

<400> SEQUENCE: 5

Asp Ile Glu Leu Thr Gln Ser Pro Ser Ser Met Tyr Thr Ser Leu Gly
1               5                   10                  15

Glu Arg Val Thr Ile Thr Cys Lys Ala Ser Gln Asp Ile Asn Ser Tyr
            20                  25                  30

Leu Arg Trp Phe Gln Gln Lys Pro Gly Lys Ser Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Thr Thr Tyr Tyr Cys Leu Gln His Gly Glu Ser Pro Tyr
                85                  90                  95

Thr Phe Gly Gly Gly Thr Lys Leu Glu Ile Lys
            100                 105

<210> SEQ ID NO 6
<211> LENGTH: 111
<212> TYPE: PRT
<213> ORGANISM: Mus musculus

<400> SEQUENCE: 6

Asn Ile Val Leu Thr Gln Ser Pro Ala Ser Leu Ala Val Ser Leu Gly
1               5                   10                  15

Gln Arg Ala Thr Ile Ser Cys Arg Ala Asn Glu Ser Val Tyr Ser Tyr
            20                  25                  30

Gly Asp Ser Phe Met His Trp Tyr Gln Gln Lys Pro Gly Gln Pro Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Thr Asp Asp Ala Ala Thr Tyr Tyr Cys Gln Gln Asn Asn
```

```
                85                  90                  95
Glu Asp Pro Trp Thr Phe Gly Gly Gly Thr Lys Leu Glu Ile Lys
            100                 105                 110
```

<210> SEQ ID NO 7
<211> LENGTH: 105
<212> TYPE: PRT
<213> ORGANISM: Mus musculus

<400> SEQUENCE: 7

```
Gln Ile Ile Leu Thr Gln Ser Pro Ala Ile Met Ser Ala Ser Pro Gly
  1               5                  10                  15

Glu Lys Val Thr Met Thr Cys Ser Ala Ser Ser Asp Ile Ser Tyr Met
             20                  25                  30

His Trp Tyr Gln Gln Lys Ser Asp Thr Ser Pro Lys Ile Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Thr Met Glu Ala Glu
 65                  70                  75                  80

Asp Ala Ala Thr Tyr Tyr Cys His Gln Arg Ser Ser Tyr Pro Thr Phe
                 85                  90                  95

Gly Gly Gly Thr Lys Leu Glu Ile Lys
            100                 105
```

<210> SEQ ID NO 8
<211> LENGTH: 107
<212> TYPE: PRT
<213> ORGANISM: Mus musculus

<400> SEQUENCE: 8

```
Asp Ile Ala Met Thr Gln Thr Thr Ser Ser Leu Ser Ala Ser Leu Gly
  1               5                  10                  15

Gln Lys Val Thr Ile Ser Cys Arg Ala Ser Gln Asp Ile Gly Asn Tyr
             20                  25                  30

Leu Asn Trp Tyr Gln Gln Lys Pro Asp Gly Thr Val Arg Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Ser
 65                  70                  75                  80

Glu Asp Ile Ala Thr Tyr Phe Cys Gln Asn Gly Gly Thr Asn Pro Trp
                 85                  90                  95

Thr Phe Gly Gly Gly Thr Lys Leu Glu Val Lys
            100                 105
```

<210> SEQ ID NO 9
<211> LENGTH: 107
<212> TYPE: PRT
<213> ORGANISM: Mus musculus

<400> SEQUENCE: 9

```
Asp Ile Gln Met Thr Gln Ser Pro Ser Ser Leu Ser Ala Thr Leu Gly
  1               5                  10                  15

Gly Lys Val Thr Ile Thr Cys Lys Ala Ser Gln Asp Ile Asn Lys Tyr
             20                  25                  30

Ile Ala Trp Tyr Gln His Lys Pro Gly Lys Gly Pro Arg Leu Leu Ile
         35                  40                  45
```

```
His Tyr Thr Ser Thr Leu Gln Pro Gly Asn Pro Ser Arg Phe Ser Gly
    50                  55                  60

Ser Gly Ser Gly Arg Asp Tyr Ser Phe Ser Ile Ser Asn Leu Glu Ala
65                  70                  75                  80

Glu Asp Ile Ala Ile Tyr Tyr Cys Leu Gln Tyr Asp Asn Leu Gln Arg
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Mus musculus

<400> SEQUENCE: 10

Asp Ile Gln Met Thr Gln Ser Pro Ser Ser Leu Ser Ala Ser Leu Gly
1               5                   10                  15

Asp Arg Val Thr Ile Ser Cys Ser Ala Ser Gln Asp Ile Asn Lys Tyr
            20                  25                  30

Leu Asn Trp Tyr Gln Gln Lys Pro Asp Gly Ala Val Lys Leu Leu Ile
        35                  40                  45

Phe Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Glu Lys Leu Pro Trp
                85                  90                  95

Thr Phe Gly Gly Gly Thr Lys Leu Glu Val Lys
            100                 105

<210> SEQ ID NO 11
<211> LENGTH: 107
<212> TYPE: PRT
<213> ORGANISM: Mus musculus

<400> SEQUENCE: 11

Asn Ile Val Leu Thr Gln Ser Pro Lys Ser Met Ser Val Ser Val Gly
1               5                   10                  15

Glu Arg Val Thr Leu Ser Cys Lys Ala Ser Glu Asn Val Asp Thr Tyr
            20                  25                  30

Val Phe Trp Phe Gln Gln Lys Pro Asp Gln Ser Pro Lys Leu Leu Leu
        35                  40                  45

Tyr Gly Pro Ser Asn Arg Tyr Thr Gly Val Pro Asp Arg Phe Thr Gly
    50                  55                  60

Ser Gly Ser Thr Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Tyr
                85                  90                  95

Thr Phe Gly Gly Gly Thr Lys Leu Glu Ile Lys
            100                 105

<210> SEQ ID NO 12
<211> LENGTH: 107
<212> TYPE: PRT
<213> ORGANISM: Mus musculus

<400> SEQUENCE: 12

Asp Ile Lys Met Thr Gln Ser Pro Ser Ser Met Tyr Thr Ser Leu Gly
1               5                   10                  15
```

Glu Arg Val Thr Ile Thr Cys Lys Ala Ser Gln Asp Ile Asn Ser Phe
            20                  25                  30

Leu Thr Trp Phe Leu Gln Lys Pro Gly Lys Ser Pro Lys Thr Leu Ile
        35                  40                  45

Tyr Arg Ala Asn Arg Leu Met Ile Gly Val Pro Ser Arg Phe Ser Gly
    50                  55                  60

Ser Gly Ser Gly Gln Thr Tyr Ser Leu Thr Ile Ser Ser Leu Glu Tyr
65                  70                  75                  80

Glu Asp Met Gly Ile Tyr Tyr Cys Leu Gln Tyr Asp Asp Phe Pro Leu
                85                  90                  95

Thr Phe Gly Ala Gly Thr Lys Leu Asp Leu Lys
            100                 105

<210> SEQ ID NO 13
<211> LENGTH: 107
<212> TYPE: PRT
<213> ORGANISM: Mus musculus

<400> SEQUENCE: 13

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Asn Ser Tyr Pro Tyr
                85                  90                  95

Thr Phe Gly Gly Gly Thr Lys Leu Glu Ile Lys
            100                 105

<210> SEQ ID NO 14
<211> LENGTH: 106
<212> TYPE: PRT
<213> ORGANISM: Mus musculus

<400> SEQUENCE: 14

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Thr Tyr
            20                  25                  30

Leu Asn Trp Tyr Gln Gln Lys Pro Asp Gly Thr Val Lys Leu Leu Ile
        35                  40                  45

Phe Tyr Thr Ser Arg Leu Arg Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Arg Ile Pro Pro
                85                  90                  95

Thr Phe Gly Gly Gly Thr Lys Leu Glu Ile
            100                 105

<210> SEQ ID NO 15
<211> LENGTH: 107

```
<212> TYPE: PRT
<213> ORGANISM: Homo sapiens

<400> SEQUENCE: 15

Ile Ala Leu Thr Gln Ser Pro Gly Thr Leu Ser Leu Ser Pro Gly Glu
 1               5                  10                  15

Arg Ala Thr Leu Ser Cys Arg Ala Ser Gln Ser Phe Ser Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Lys Tyr Gly Thr Ser Ala Ile
                85                  90                  95

Thr Phe Gly Gln Gly Thr Arg Leu Glu Ile Lys
            100                 105

<210> SEQ ID NO 16
<211> LENGTH: 107
<212> TYPE: PRT
<213> ORGANISM: Mus musculus

<400> SEQUENCE: 16

Asp Ile Val Leu Thr Gln Ser Pro Ala Thr Leu Ser Val Thr Pro Gly
 1               5                  10                  15

Asn Ser Val Ser Leu Ser Cys Arg Ala Ser Gln Ser Ile Gly Asn Asn
                20                  25                  30

Leu His Trp Tyr Gln Gln Lys Ser His Glu Ser Pro Arg Leu Leu Ile
            35                  40                  45

Lys Phe Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Mus musculus

<400> SEQUENCE: 17

Asp Ile Glu Leu Thr Gln Ser Pro Ser Tyr Leu Val Ala Ser Pro Gly
 1               5                  10                  15

Glu Thr Ile Thr Ile Asn Cys Arg Ala Ser Lys Ser Ile Ser Lys Ser
                20                  25                  30

Leu Ala Trp Tyr Gln Glu Lys Pro Gly Lys Thr Asn Asn Leu Leu Ile
            35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Ile Cys Gln Gln His Asn Glu Tyr Pro Trp
                85                  90                  95
```

```
Thr Phe Gly Gly Gly Thr Lys Leu Glu Ile Lys
            100                 105

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gln Gly Thr Lys Val Glu Ile Lys
            100                 105

<210> SEQ ID NO 19
<211> LENGTH: 105
<212> TYPE: PRT
<213> ORGANISM: Mus musculus

<400> SEQUENCE: 19

Val Glu Met Thr Gln Ser Pro Ser Ser Phe Ser Val Ser Leu Gly Asp
1               5                   10                  15

Arg Val Thr Ile Thr Cys Lys Ala Ser Glu Asp Ile Tyr Asn Arg Leu
            20                  25                  30

Ala Trp Tyr Gln Gln Lys Pro Gly Asn Ala Pro Arg Leu Leu Ile Ser
        35                  40                  45

Gly Ala Thr Ser Leu Glu Thr Glu Val Pro Ser Arg Phe Ser Gly Ser
    50                  55                  60

Gly Ser Gly Lys Asp Tyr Thr Leu Ser Ile Thr Ser Leu Gln Thr Glu
65                  70                  75                  80

Asp Val Ala Thr Tyr Tyr Cys Gln Gln Tyr Trp Ser Thr Trp Thr Phe
                85                  90                  95

Gly Gly Gly Thr Lys Leu Glu Ile Lys
            100                 105

<210> SEQ ID NO 20
<211> LENGTH: 106
<212> TYPE: PRT
<213> ORGANISM: Mus musculus

<400> SEQUENCE: 20

Asp Ile Val Leu Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
```

```
                50                  55                  60
Ser Gly Ser Ala Thr Asp Phe Thr Leu Lys Ile Ser Ser Val Gln Ala
 65                  70                  75                  80

Glu Asp Leu Ala Asp Tyr His Cys Gly Gln Thr Tyr Ser Tyr Pro Thr
                 85                  90                  95

Phe Gly Gly Gly Thr Lys Leu Ala Ile Lys
                100                 105

<210> SEQ ID NO 21
<211> LENGTH: 107
<212> TYPE: PRT
<213> ORGANISM: Mus musculus

<400> SEQUENCE: 21

Asp Ile Glu Leu Thr Gln Ser Pro Ala Thr Leu Ser Val Thr Pro Gly
  1               5                  10                  15

Asp Ser Val Ser Leu Ser Cys Arg Ala Ser Gln Ser Ile Ser Asn Asn
                 20                  25                  30

Leu His Trp Tyr Gln Gln Lys Ser His Glu Ser Pro Arg Leu Leu Ile
             35                  40                  45

Lys Tyr Val Ser Gln Ser Ser Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Arg
                 85                  90                  95

Thr Phe Gly Gly Gly Thr Lys Leu Glu Ile Lys
                100                 105

<210> SEQ ID NO 22
<211> LENGTH: 107
<212> TYPE: PRT
<213> ORGANISM: Mus musculus

<400> SEQUENCE: 22

Asp Ile Val Leu Thr Gln Ser Pro Ala Thr Leu Ser Val Thr Pro Gly
  1               5                  10                  15

Asp Ser Val Ser Leu Ser Cys Arg Ala Ser Gln Ser Ile Ser Asn Asn
                 20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                 85                  90                  95

Thr Phe Gly Gly Gly Thr Lys Leu Glu Ile Lys
                100                 105

<210> SEQ ID NO 23
<211> LENGTH: 107
<212> TYPE: PRT
<213> ORGANISM: Mus musculus

<400> SEQUENCE: 23

Asp Ile Val Met Thr Gln Ser Pro Lys Phe Met Ser Thr Ser Val Gly
  1               5                  10                  15
```

Asp Arg Val Thr Ile Thr Cys Lys Ala Ser Gln Asp Val Ser Thr Ala
            20                  25                  30

Val Val Trp Tyr Gln Lys Pro Gly Gln Ser Pro Lys Leu Leu Ile
        35                  40                  45

Tyr Trp Ala Ser Thr Arg His Ile Gly Val Pro Asp Arg Phe Ala Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Pro Pro Trp
                85                  90                  95

Thr Phe Gly Gly Gly Thr Lys Leu Glu Ile Lys
            100                 105

<210> SEQ ID NO 24
<211> LENGTH: 107
<212> TYPE: PRT
<213> ORGANISM: Mus musculus

<400> SEQUENCE: 24

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 25
<211> LENGTH: 107
<212> TYPE: PRT
<213> ORGANISM: Mus musculus

<400> SEQUENCE: 25

Ile Val Met Thr Gln Thr Pro Ala Ile Met Ser Ala Phe Leu Gly Glu
1               5                   10                  15

Arg Val Thr Met Thr Cys Thr Ala Thr Ser Ser Leu Ser Ser Ser Tyr
            20                  25                  30

Leu His Trp Tyr Gln Gln Lys Pro Gly Ser Ser Pro Lys Leu Trp Ile
        35                  40                  45

Tyr Thr Thr Ser Asn Leu Ala Ser Gly Val Pro Ser Arg Phe Ser Gly
    50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys His Gln Phe His His Ser Pro Tyr
                85                  90                  95

Thr Phe Gly Gly Gly Thr Lys Leu Glu Ile Lys
            100                 105

<210> SEQ ID NO 26
<211> LENGTH: 107
<212> TYPE: PRT

<213> ORGANISM: Mus musculus

<400> SEQUENCE: 26

Gln Ile Val Leu Thr Gln Ser Pro Ala Ile Met Ser Ala Ser Leu Gly
1               5                   10                  15

Asp Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Phe His Arg Ser Leu
                85                  90                  95

Thr Phe Gly Ser Gly Thr Lys Leu Glu Ile Lys
            100                 105

<210> SEQ ID NO 27
<211> LENGTH: 106
<212> TYPE: PRT
<213> ORGANISM: Mus musculus

<400> SEQUENCE: 27

Asp Ile Gln Met Ser Gln Ser Ser Ser Phe Ser Val Ser Leu Gly
1               5                   10                  15

Asp Arg Val Thr Ile Thr Cys Lys Ala Ser Glu Asp Ile Tyr Ser Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Trp Val Pro Ser Arg Phe Ser Gly
    50                  55                  60

Ser Asp Ser Gly Lys Asp Tyr Thr Leu Ser Ile Thr Ser Leu Gln Thr
65                  70                  75                  80

Glu Asp Val Ala Thr Tyr Phe Cys Gln Gln Tyr Trp Ser Pro Pro Pro
                85                  90                  95

Thr Phe Gly Gly Gly Thr Lys Leu Glu Ile
            100                 105

<210> SEQ ID NO 28
<211> LENGTH: 104
<212> TYPE: PRT
<213> ORGANISM: Mus musculus

<400> SEQUENCE: 28

Ile Val Leu Thr Gln Ser Pro Ala Ile Met Ser Ala Ala Pro Gly Asp
1               5                   10                  15

Lys Val Thr Met Thr Cys Ser Ala Ser Ser Ser Val Ser Tyr Ile His
            20                  25                  30

Trp Tyr Gln Gln Lys Ser Gly Thr Ser Pro Lys Arg Trp Ile Tyr Asp
        35                  40                  45

Thr Ser Lys Leu Thr Ser Gly Val Pro Val Arg Phe Ser Gly Ser Gly
    50                  55                  60

Ser Gly Thr Ser Tyr Ser Leu Thr Ile Asn Thr Met Glu Ala Glu Asp
65                  70                  75                  80

Ala Ala Thr Tyr Tyr Cys Gln Gln Trp Ser Ser His Pro Gln Thr Phe
                85                  90                  95

```
Gly Gly Gly Thr Lys Leu Glu Ile
            100

<210> SEQ ID NO 29
<211> LENGTH: 107
<212> TYPE: PRT
<213> ORGANISM: Mus musculus

<400> SEQUENCE: 29

Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Thr Ser Gln Ser Met Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Gly Ser Trp Pro Arg
                85                  90                  95

Thr Phe Gly Gly Gly Thr Lys Leu Asp Ile Lys
            100                 105

<210> SEQ ID NO 30
<211> LENGTH: 112
<212> TYPE: PRT
<213> ORGANISM: Mus musculus

<400> SEQUENCE: 30

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Thr Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

<210> SEQ ID NO 31
<211> LENGTH: 111
<212> TYPE: PRT
<213> ORGANISM: Mus musculus

<400> SEQUENCE: 31

Asn Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Phe Pro Thr Phe Gly Gly Gly Thr Lys Leu Glu Ile Lys
                100                 105                 110

<210> SEQ ID NO 32
<211> LENGTH: 107
<212> TYPE: PRT
<213> ORGANISM: Mus musculus

<400> SEQUENCE: 32

Asp Ile Gln Met Thr Gln Thr Thr Ser Ser Leu Ser Ala Ser Leu Gly
  1               5                  10                  15

Asp Arg Val Thr Ile Ser Cys Ser Ala Ser Gln Asp Ile Ser Ser Tyr
                 20                  25                  30

Leu Asn Trp Tyr Gln Gln Lys Pro Glu Gly Thr Val Lys Leu Leu Ile
             35                  40                  45

Tyr Tyr Thr Ser Ser Leu His Ser Gly Val Pro Ser Arg Phe Ser Gly
         50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Phe Pro Trp
                 85                  90                  95

Thr Phe Gly Gly Gly Thr Lys Leu Glu Ile Lys
                100                 105

<210> SEQ ID NO 33
<211> LENGTH: 107
<212> TYPE: PRT
<213> ORGANISM: Mus musculus

<400> SEQUENCE: 33

Asp Ile Gln Met Asn Gln Ser Pro Ser Ser Leu Ser Ala Ser Leu Gly
  1               5                  10                  15

Asp Thr Ile Thr Ile Thr Cys His Ala Ser Gln Asn Ile Asn Val Trp
                 20                  25                  30

Leu Asn Trp Phe Gln Gln Lys Pro Gly Ser Ile Pro Lys Leu Leu Ile
             35                  40                  45

Tyr Met Ala Ser Asn Leu His Thr Gly Val Pro Ser Arg Phe Ser Gly
         50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Phe Pro Leu
                 85                  90                  95

Thr Phe Gly Gly Gly Thr Lys Leu Glu Ile Lys
                100                 105

<210> SEQ ID NO 34
<211> LENGTH: 107
<212> TYPE: PRT
<213> ORGANISM: Homo sapiens

<400> SEQUENCE: 34

Ala Leu Gln Leu Thr Gln Ser Pro Ser Ser Leu Ser Ala Ser Val Gly
  1               5                  10                  15

Asp Arg Ile Thr Ile Thr Cys Arg Ala Ser Gln Gly Val Thr Ser Ala
```

-continued

```
                    20                  25                  30
Leu Ala Trp Tyr Arg Gln Lys Pro Gly Ser Pro Gln Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Thr Leu Arg Pro
 65                  70                  75                  80

Glu Asp Phe Ala Thr Tyr Tyr Cys Gln Gln Leu His Phe Tyr Pro His
                 85                  90                  95

Thr Phe Gly Gly Gly Thr Arg Val Asp Val Arg
                100                 105
```

```
<210> SEQ ID NO 35
<211> LENGTH: 112
<212> TYPE: PRT
<213> ORGANISM: Mus musculus

<400> SEQUENCE: 35

Asp Val Val Met Ser Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Ile Tyr Phe Cys Trp Gln Gly
                 85                  90                  95

Ser His Phe Pro Gln Thr Phe Gly Gly Gly Thr Lys Leu Glu Ile Lys
                100                 105                 110
```

```
<210> SEQ ID NO 36
<211> LENGTH: 107
<212> TYPE: PRT
<213> ORGANISM: Mus musculus

<400> SEQUENCE: 36

Asp Ile Leu Met Thr Gln Ser Pro Ser Ser Met Ser Val Ser Leu Gly
 1               5                  10                  15

Asp Thr Val Ser Ile Thr Cys His Ala Ser Gln Gly Ile Ser Ser Asn
                20                  25                  30

Ile Gly Trp Leu Gln Gln Lys Pro Gly Lys Ser Phe Met Gly Leu Ile
        35                  40                  45

Tyr Tyr Gly Thr Asn Leu Val Asp Gly Val Pro Ser Arg Phe Ser Gly
 50                  55                  60

Ser Gly Ser Gly Ala Asp Tyr Ser Leu Thr Ile Ser Ser Leu Asp Ser
 65                  70                  75                  80

Glu Asp Phe Ala Asp Tyr Tyr Cys Val Gln Tyr Ala Gln Leu Pro Tyr
                 85                  90                  95

Thr Phe Gly Gly Gly Thr Lys Leu Glu Ile Lys
                100                 105
```

```
<210> SEQ ID NO 37
<211> LENGTH: 104
<212> TYPE: PRT
<213> ORGANISM: Mus musculus
```

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ser Tyr Ser Ser
            20                  25                  30

Val Ala Trp Tyr Gln Gln Lys Pro Gly Lys Ala Pro Lys Leu Leu Ile
        35                  40                  45

Tyr Ala Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Ala Ser Pro Ala Thr
                85                  90                  95

Phe Gly Gln Gly Thr Lys Val Glu
            100

<210> SEQ ID NO 38
<211> LENGTH: 107
<212> TYPE: PRT
<213> ORGANISM: Mus musculus

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Tyr Ala Tyr Ala
            20                  25                  30

Val Ala Trp Tyr Gln Gln Lys Pro Gly Lys Ala Pro Lys Leu Leu Ile
        35                  40                  45

Tyr Asp Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Ser Pro Asp
                85                  90                  95

Thr Phe Gly Gln Gly Thr Lys Val Glu Ile Lys
            100                 105

<210> SEQ ID NO 39
<211> LENGTH: 107
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Lys Ser Phe
            20                  25                  30

Leu Ser Trp Tyr Gln Gln Lys Pro Glu Lys Ala Pro Lys Ser Leu Ile
        35                  40                  45

Tyr Tyr Ala Thr Ser Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Tyr
                85                  90                  95

Thr Phe Gly Gly Gly Thr Lys Val Glu Ile Lys

-continued

<210> SEQ ID NO 40
<211> LENGTH: 106
<212> TYPE: PRT
<213> ORGANISM: Mus musculus

<400> SEQUENCE: 40

Ile Val Met Thr Gln Thr Pro Ala Ser Gln Ser Ala Ser Leu Gly Glu
1               5                   10                  15

Ser Val Thr Ile Thr Cys Leu Ala Ser Gln Thr Ile Gly Thr Trp Leu
            20                  25                  30

Ala Trp Tyr Gln Gln Lys Pro Gly Lys Ser Pro Gln Leu Leu Ile Tyr
        35                  40                  45

Ala Ala Thr Ser Leu Ala Asp Gly Val Pro Ser Arg Phe Ser Gly Ser
    50                  55                  60

Gly Ser Gly Thr Lys Phe Ser Phe Lys Ile Ser Ser Leu Gln Ala Glu
65                  70                  75                  80

Asp Phe Val Ser Tyr Tyr Cys Gln Gln Leu Ser Ser Thr Pro Tyr Thr
                85                  90                  95

Phe Gly Gly Gly Thr Lys Leu Glu Ile Lys
            100                 105

<210> SEQ ID NO 41
<211> LENGTH: 112
<212> TYPE: PRT
<213> ORGANISM: Mus musculus

<400> SEQUENCE: 41

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu Tyr Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Val Pro Trp Thr Phe Gly Gly Gly Thr Lys Leu Glu Ile Lys
            100                 105                 110

<210> SEQ ID NO 42
<211> LENGTH: 106
<212> TYPE: PRT
<213> ORGANISM: Mus musculus

<400> SEQUENCE: 42

Gln Val Val Leu Thr Gln Ser Pro Gly Ile Met Ser Ala Ser Pro Gly
1               5                   10                  15

Glu Lys Val Thr Ile Thr Cys Ser Ala Ser Ser Ser Val Ser Tyr Met
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Arg Gly Ser
    50                  55                  60

```
Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Gly Tyr Pro Arg Thr
                 85                  90                  95

Phe Gly Gly Gly Thr Lys Leu Glu Ile Lys
            100                 105

<210> SEQ ID NO 43
<211> LENGTH: 107
<212> TYPE: PRT
<213> ORGANISM: Mus musculus

<400> SEQUENCE: 43

Asp Ile Gln Met Thr Gln Ser Pro Ala Ser Leu Ser Ala Ser Val Gly
  1               5                  10                  15

Glu Thr Val Thr Ile Thr Cys Arg Ala Ser Gly Asn Ile His Asn Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Thr Pro Trp
                 85                  90                  95

Thr Phe Gly Gly Gly Thr Lys Leu Glu Ile Lys
            100                 105

<210> SEQ ID NO 44
<211> LENGTH: 104
<212> TYPE: PRT
<213> ORGANISM: Mus musculus

<400> SEQUENCE: 44

Ile Val Leu Thr Gln Ser Pro Ala Ile Met Ser Ala Ser Pro Gly Glu
  1               5                  10                  15

Lys Val Thr Met Thr Cys Ser Ala Ser Ser Ser Val Asn Tyr Met Tyr
                 20                  25                  30

Trp Tyr Gln Gln Lys Ser Gly Thr Ser Pro Lys Arg Trp Ile Tyr Asp
             35                  40                  45

Thr Ser Lys Leu Ala Ser Gly Val Pro Val Arg Phe Ser Gly Ser Gly
 50                  55                  60

Ser Gly Thr Ser Tyr Ser Leu Thr Ile Ser Ser Met Glu Thr Glu Asp
 65                  70                  75                  80

Ala Ala Thr Tyr Tyr Cys Gln Gln Trp Gly Arg Asn Pro Thr Phe Gly
                 85                  90                  95

Gly Gly Thr Lys Leu Glu Ile Lys
            100

<210> SEQ ID NO 45
<211> LENGTH: 107
<212> TYPE: PRT
<213> ORGANISM: Mus musculus

<400> SEQUENCE: 45

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ser Thr Ala
                 20                  25                  30
```

```
Val Ala Trp Tyr Gln Gln Lys Pro Gly Gln Ser Pro Lys Leu Leu Ile
            35                  40                  45

Ser Trp Ala Ser Thr Arg His Thr Gly Val Pro Asp Arg Phe Thr Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Thr Thr Pro Leu
                 85                  90                  95

Thr Phe Gly Ala Gly Thr Lys Leu Glu Leu Lys
                100                 105
```

<210> SEQ ID NO 46
<211> LENGTH: 106
<212> TYPE: PRT
<213> ORGANISM: Mus musculus

<400> SEQUENCE: 46

```
Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Arg Thr
                 85                  90                  95

Phe Gly Gly Gly Thr Lys Leu Glu Ile Lys
                100                 105
```

<210> SEQ ID NO 47
<211> LENGTH: 107
<212> TYPE: PRT
<213> ORGANISM: Mus musculus

<400> SEQUENCE: 47

```
Asp Ile Leu Met Thr Gln Ser Gln Lys Phe Leu Ser Thr Ser Val Gly
 1               5                  10                  15

Asp Arg Val Ser Val Thr Cys Lys Ala Ser Gln Asn Val Gly Thr Asn
            20                  25                  30

Val Ala Trp Tyr Gln Lys Lys Pro Gly Gln Ser Pro Lys Pro Leu Met
            35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Phe Asn Arg Tyr Pro Leu
                 85                  90                  95

Thr Phe Gly Ser Gly Thr Lys Leu Glu Leu Lys
                100                 105
```

<210> SEQ ID NO 48
<211> LENGTH: 107
<212> TYPE: PRT
<213> ORGANISM: Mus musculus

```
<400> SEQUENCE: 48

Asp Ile Gln Met Thr Gln Ser Ser Ser Phe Ser Val Ser Leu Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Phe Trp Ser Ala Pro Tyr
                85                  90                  95

Thr Phe Gly Gly Gly Thr Lys Leu Glu Ile Lys
            100                 105

<210> SEQ ID NO 49
<211> LENGTH: 106
<212> TYPE: PRT
<213> ORGANISM: Mus musculus

<400> SEQUENCE: 49

Val Leu Thr Gln Ser Pro Ala Ile Met Ser Ala Ser Pro Gly Glu Lys
1               5                   10                  15

Val Thr Met Thr Cys Arg Ala Ser Ser Val Ser Ser Ser Tyr Leu
            20                  25                  30

His Trp Tyr Gln Gln Lys Ser Gly Ala Ser Pro Lys Leu Trp Ile Tyr
        35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Tyr Ser Gly Tyr Pro Tyr Thr
                85                  90                  95

Phe Gly Gly Gly Thr Lys Leu Glu Ile Lys
            100                 105

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105
```

```
<210> SEQ ID NO 51
<211> LENGTH: 107
<212> TYPE: PRT
<213> ORGANISM: Mus musculus

<400> SEQUENCE: 51

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 52
<211> LENGTH: 105
<212> TYPE: PRT
<213> ORGANISM: Mus musculus

<400> SEQUENCE: 52

Asp Ile Val Leu Thr Gln Ser Pro Asp Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Phe
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Phe Thr Phe
                85                  90                  95

Gly Gly Gly Thr Lys Leu Glu Ile Lys
            100                 105

<210> SEQ ID NO 53
<211> LENGTH: 107
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                 65                  70                  75                  80
Glu Asp Phe Ala Thr Tyr Tyr Cys Gln Gln Ser Tyr Thr Thr Pro Pro
                         85                  90                  95

Thr Phe Gly Gln Gly Thr Lys Val Glu Ile Lys
                100                 105
```

<210> SEQ ID NO 54
<211> LENGTH: 112
<212> TYPE: PRT
<213> ORGANISM: Mus musculus

<400> SEQUENCE: 54

```
Asp Ile Val Met Ser Gln Ser Pro Ser Ser Leu Ala Val Ser Ala Gly
1               5                   10                  15

Glu Arg Val Thr Met Thr Cys Lys Ser Ser Gln Ser Leu Phe Asn Ser
                20                  25                  30

Lys Thr Arg Arg Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Glu Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
                100                 105                 110
```

<210> SEQ ID NO 55
<211> LENGTH: 107
<212> TYPE: PRT
<213> ORGANISM: Homo sapiens

<400> SEQUENCE: 55

```
Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
                20                  25                  30

Leu Ala Trp Tyr Gln Gln Lys Pro Gly Gln Ala Pro Arg Pro Leu Ile
            35                  40                  45

Tyr Asp Ala Ser Thr Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Val Lys
                100                 105
```

<210> SEQ ID NO 56
<211> LENGTH: 107
<212> TYPE: PRT
<213> ORGANISM: Mus musculus

<400> SEQUENCE: 56

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asp
                20                  25                  30
```

-continued

```
Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asn Tyr Tyr Cys Gln Gln Ser Asn Arg Trp Pro Phe
                85                  90                  95

Thr Phe Gly Ser Gly Thr Lys Leu Glu Ile Lys
                100                 105
```

<210> SEQ ID NO 57
<211> LENGTH: 112
<212> TYPE: PRT
<213> ORGANISM: Mus musculus

<400> SEQUENCE: 57

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
                100                 105                 110
```

<210> SEQ ID NO 58
<211> LENGTH: 107
<212> TYPE: PRT
<213> ORGANISM: Mus musculus

<400> SEQUENCE: 58

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Ser Ser Tyr
            20                  25                  30

Leu Asn Trp Tyr Gln Gln Lys Pro Glu Gly Thr Val Lys Leu Leu Ile
        35                  40                  45

Tyr Tyr Thr Ser Ser Leu His Ser Gly Val Pro Ser Ala Phe Ser Gly
    50                  55                  60

Ser Gly Ser Gly Thr Asp Tyr Ser Leu Thr Ile Ser Asn Leu Glu Pro
65                  70                  75                  80

Glu Asp Phe Ala Thr Tyr Tyr Cys Gln Gln Tyr Ser Lys Phe Pro Trp
                85                  90                  95

Thr Phe Gly Gly Gly Thr Lys Leu Glu Ile Lys
                100                 105
```

<210> SEQ ID NO 59
<211> LENGTH: 111
<212> TYPE: PRT
<213> ORGANISM: Mus musculus

<400> SEQUENCE: 59

```
Asp Thr Val Leu Thr Gln Ser Pro Ala Ser Leu Ala Val Ser Leu Gly
 1               5                  10                 15

Gln Arg Ala Thr Ile Ser Cys Arg Ala Ser Glu Ser Val Asp Tyr Tyr
             20                 25                 30

Gly Lys Ser Phe Met Asn Trp Phe Gln Gln Lys Pro Gly Gln Pro Pro
         35                 40                 45

Lys Leu Leu Ile Tyr Ala Ala Ser Asn Gln Gly Ser Gly Val Pro Ala
     50                 55                 60

Arg Phe Ser Gly Ser Gly Ser Gly Thr Asp Phe Ser Leu His Ile His
 65                 70                 75                 80

Pro Met Glu Glu Asp Asp Ser Ala Met Tyr Phe Cys Gln Gln Ser Lys
                 85                 90                 95

Glu Val Pro Trp Thr Phe Gly Gly Gly Thr Lys Leu Glu Ile Lys
             100                105                110
```

<210> SEQ ID NO 60
<211> LENGTH: 107
<212> TYPE: PRT
<213> ORGANISM: Mus musculus

<400> SEQUENCE: 60

```
Asp Ile Leu Leu Thr Gln Ser Pro Ala Ile Leu Ser Val Ser Pro Gly
 1               5                  10                 15

Glu Arg Val Ser Phe Ser Cys Arg Ala Ser Gln Ser Ile Gly Thr Asp
             20                 25                 30

Ile His Trp Tyr Gln Gln Arg Thr Asn Gly Ser Pro Arg Leu Leu Ile
         35                 40                 45

Lys Tyr Ala Ser Glu Ser Ile Ser Gly Ile Pro Ser Arg Phe Ser Gly
     50                 55                 60

Ser Gly Ser Gly Thr Asp Phe Thr Leu Ser Ile Asn Ser Val Glu Ser
 65                 70                 75                 80

Glu Asp Ile Ala Asn Tyr Tyr Cys Gln Gln Ser Asn Arg Trp Pro Phe
                 85                 90                 95

Thr Phe Gly Ser Gly Thr Lys Leu Glu Ile Lys
             100                105
```

<210> SEQ ID NO 61
<211> LENGTH: 107
<212> TYPE: PRT
<213> ORGANISM: Mus musculus

<400> SEQUENCE: 61

```
Asp Ile Glu Leu Thr Gln Thr Pro Val Ser Leu Ala Ala Ser Leu Gly
 1               5                  10                 15

Asp Arg Val Thr Ile Ser Cys Arg Ala Ser Gln Asp Ile Asn Asn Phe
             20                 25                 30

Leu Asn Trp Tyr Gln Gln Lys Pro Asp Gly Thr Ile Lys Leu Leu Ile
         35                 40                 45

Tyr Tyr Thr Ser Arg Leu His Ala Gly Val Pro Ser Arg Phe Ser Gly
     50                 55                 60

Ser Gly Ser Gly Thr Asp Tyr Ser Leu Thr Ile Ser Asn Leu Glu Pro
 65                 70                 75                 80

Glu Asp Ile Ala Thr Tyr Phe Cys Gln His Ile Lys Phe Pro Trp
                 85                 90                 95

Thr Phe Gly Ala Gly Thr Lys Leu Glu Ile Lys
             100                105
```

<210> SEQ ID NO 62
<211> LENGTH: 107
<212> TYPE: PRT
<213> ORGANISM: Mus musculus

<400> SEQUENCE: 62

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asp
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asn Tyr Tyr Cys Gln Gln Ser Asn Arg Trp Pro Phe
                85                  90                  95

Thr Phe Gly Ser Gly Thr Lys Leu Glu Ile Lys
            100                 105

<210> SEQ ID NO 63
<211> LENGTH: 104
<212> TYPE: PRT
<213> ORGANISM: Mus musculus

<400> SEQUENCE: 63

Val Leu Ser Gln Ser Pro Ala Ile Leu Ser Ala Ser Pro Gly Glu Lys
1               5                   10                  15

Val Thr Met Thr Cys Arg Ala Arg Ser Ser Val Ser Tyr Met His Trp
            20                  25                  30

Tyr Gln Gln Lys Ser Gly Ser Ser Pro Lys Pro Trp Ile His Ala Thr
        35                  40                  45

Ser Asn Leu Ala Ser Gly Val Pro Ala Arg Phe Ser Gly Ser Gly Ser
    50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Ser His Pro Pro Thr Phe Gly
                85                  90                  95

Ser Gly Thr Lys Leu Glu Ile Lys
            100

<210> SEQ ID NO 64
<211> LENGTH: 112
<212> TYPE: PRT
<213> ORGANISM: Mus musculus

<400> SEQUENCE: 64

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 65
<211> LENGTH: 109
<212> TYPE: PRT
<213> ORGANISM: Homo sapiens

<400> SEQUENCE: 65

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Arg Tyr Thr Phe Gly Gln Gly Thr Arg Leu Glu Ile Lys
            100                 105

<210> SEQ ID NO 66
<211> LENGTH: 107
<212> TYPE: PRT
<213> ORGANISM: Mus musculus

<400> SEQUENCE: 66

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Phe Gln Gln Arg Ile Asn Gly Ser Pro Arg Leu Leu Ile
        35                  40                  45

Glu Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Val Trp Pro Phe
                85                  90                  95

Thr Phe Gly Ser Gly Thr Lys Leu Glu Ile Lys
            100                 105

<210> SEQ ID NO 67
<211> LENGTH: 104
<212> TYPE: PRT
<213> ORGANISM: Homo sapiens

<400> SEQUENCE: 67

Ile Gln Met Thr Gln Ser Pro Ser Ser Leu Ser Ala Ser Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Pro Gly Glu Ala Pro Lys Leu Leu Ile Tyr

```
                35                  40                  45
Ser Ala Ser Val Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Val Met Ile Pro Met Thr
                 85                  90                  95

Phe Gly Gln Gly Thr Lys Val Glu
                100

<210> SEQ ID NO 68
<211> LENGTH: 113
<212> TYPE: PRT
<213> ORGANISM: Mus musculus

<400> SEQUENCE: 68

Asp Ile Val Met Thr Gln Ser Pro Ser Ser Leu Thr Val Thr Thr Gly
 1                5                  10                  15

Glu Lys Val Thr Met Thr Cys Lys Ser Ser Gln Ser Leu Leu Asn Ser
                20                  25                  30

Arg Thr Gln Lys Asn Tyr Leu Thr Trp Tyr Gln Gln Lys Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Ser
 65                  70                  75                  80

Ile Ser Gly Val Gln Ala Glu Asp Leu Ala Val Tyr Tyr Cys Gln Asn
                 85                  90                  95

Asn Tyr Asn Tyr Pro Leu Thr Phe Gly Ala Gly Thr Lys Leu Glu Leu
                100                 105                 110

Lys

<210> SEQ ID NO 69
<211> LENGTH: 110
<212> TYPE: PRT
<213> ORGANISM: Mus musculus

<400> SEQUENCE: 69

Asp Ile Val Met Thr Gln Ser Pro Ala Ser Leu Val Val Ser Leu Gly
 1                5                  10                  15

Gln Arg Ala Thr Ile Ser Cys Arg Ala Ser Glu Ser Val Asp Ser Tyr
                20                  25                  30

Gly Lys Ser Phe Met His Trp Tyr Gln Gln Lys Pro Gly Gln Pro Pro
                35                  40                  45

Lys Val Leu Ile Tyr Ile Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Pro Thr Phe Gly Ala Gly Thr Lys Leu Glu Met
                100                 105                 110

<210> SEQ ID NO 70
<211> LENGTH: 107
<212> TYPE: PRT
<213> ORGANISM: Mus musculus
```

-continued

```
<400> SEQUENCE: 70

Asp Ile Gln Met Thr Gln Thr Pro Ser Ser Leu Ser Ala Ser Leu Gly
  1               5                  10                  15

Asp Arg Val Thr Ile Ser Cys Arg Ala Ser Gln Asp Ile Ser His Tyr
             20                  25                  30

Leu Asn Trp Phe Gln Gln Lys Pro Asp Gly Thr Val Lys Leu Leu Ile
         35                  40                  45

Tyr Tyr Thr Ser Thr Leu His Ser Gly Val Pro Ser Arg Phe Ser Gly
 50                  55                  60

Ser Gly Ser Gly Thr Asp Tyr Ser Leu Thr Ile Ser Asn Leu Glu Glu
 65                  70                  75                  80

Glu Asp Ile Ala Phe Tyr Phe Cys Gln Gln Gly Gly Ala Leu Pro Phe
                 85                  90                  95

Thr Phe Gly Ser Gly Thr Lys Leu Ala Ile Lys
            100                 105

<210> SEQ ID NO 71
<211> LENGTH: 111
<212> TYPE: PRT
<213> ORGANISM: Mus musculus

<400> SEQUENCE: 71

Asp Ile Val Leu Thr Gln Ser Pro Ala Ser Leu Ala Val Ser Leu Gly
  1               5                  10                  15

Gln Arg Ala Thr Ile Ser Cys Lys Ala Ser Gln Gly Val Asp Phe Asp
             20                  25                  30

Gly Ala Ser Phe Met Asn Trp Tyr Gln Gln Lys Pro Gly Gln Pro Pro
         35                  40                  45

Lys Leu Leu Ile Phe Ala Ala Ser Thr Leu Glu Ser Gly Ile Pro Ala
 50                  55                  60

Arg Phe Ser Gly Arg Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser His
                 85                  90                  95

Glu Asp Pro Leu Thr Phe Gly Ala Gly Thr Lys Leu Glu Leu Lys
            100                 105                 110

<210> SEQ ID NO 72
<211> LENGTH: 112
<212> TYPE: PRT
<213> ORGANISM: Mus musculus

<400> SEQUENCE: 72

Asp Val Gln Met Thr Gln Thr Pro Leu Thr Leu Ser Val Thr Ile Gly
  1               5                  10                  15

Gln Pro Ala Ser Ile Ser Cys Glu Ser Ser Gln Ser Leu Leu Tyr Ser
             20                  25                  30

Asn Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Arg Ile
 65                  70                  75                  80

Ser Arg Val Glu Ala Glu Asp Leu Gly Val Tyr Tyr Cys Val Gln Gly
                 85                  90                  95

Thr His Phe Pro Arg Thr Phe Gly Gly Gly Thr Lys Leu Glu Ile Lys
            100                 105                 110
```

<210> SEQ ID NO 73
<211> LENGTH: 113
<212> TYPE: PRT
<213> ORGANISM: Mus musculus

<400> SEQUENCE: 73

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Lys Arg Lys Asn Phe Leu Thr Trp Tyr His Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Val Gln Ala Glu Asp Leu Ala Ile Tyr Tyr Cys Gln Asn
                85                  90                  95

Asp Tyr Ser His Pro Leu Thr Phe Gly Ala Gly Thr Lys Leu Glu Leu
            100                 105                 110

Lys

<210> SEQ ID NO 74
<211> LENGTH: 111
<212> TYPE: PRT
<213> ORGANISM: Mus musculus

<400> SEQUENCE: 74

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Asp Asp
            20                  25                  30

Gly Asn Ser Phe Leu His Trp Tyr Gln Gln Lys Pro Gly Gln Pro Pro
        35                  40                  45

Lys Leu Leu Ile Tyr Arg Ser Ser Asn Leu Ile Ser Gly Ile Pro Asp
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Ile Lys
            100                 105                 110

<210> SEQ ID NO 75
<211> LENGTH: 103
<212> TYPE: PRT
<213> ORGANISM: Mus musculus

<400> SEQUENCE: 75

Leu Thr Gln Ser Pro Ala Ser Leu Ser Val Ala Thr Gly Glu Lys Val
1               5                   10                  15

Thr Ile Arg Cys Met Thr Ser Thr Asp Ile Asp Asp Asp Met Asn Trp
            20                  25                  30

Tyr Gln Gln Lys Pro Gly Glu Pro Pro Lys Phe Leu Ile Ser Glu Gly
        35                  40                  45

Asn Thr Leu Arg Pro Gly Val Pro Ser Arg Phe Ser Ser Ser Gly Thr
    50                  55                  60

-continued

Gly Thr Asp Phe Val Phe Thr Ile Glu Asn Thr Leu Ser Glu Asp Val
65                  70                  75                  80

Gly Asp Tyr Tyr Cys Leu Gln Ser Phe Asn Val Pro Leu Thr Phe Gly
                85                  90                  95

Cys Gly Thr Lys Leu Glu Ile
            100

<210> SEQ ID NO 76
<211> LENGTH: 113
<212> TYPE: PRT
<213> ORGANISM: Mus musculus

<400> SEQUENCE: 76

Asp Ile Val Met Thr Gln Ser Pro Ser Ser Leu Thr Val Thr Ala Gly
1               5                   10                  15

Glu Lys Val Thr Met Ser Cys Thr Ser Ser Gln Ser Leu Phe Asn Ser
            20                  25                  30

Gly Lys Gln Lys Asn Tyr Leu Thr Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Asn Pro Leu Thr Phe Gly Gly Gly Thr Lys Leu Glu Leu
            100                 105                 110

Lys

<210> SEQ ID NO 77
<211> LENGTH: 107
<212> TYPE: PRT
<213> ORGANISM: Mus musculus

<400> SEQUENCE: 77

Asp Ile Val Leu Thr Gln Ser Pro Lys Ser Met Ser Met Ser Val Gly
1               5                   10                  15

Glu Lys Val Thr Leu Ser Cys Lys Ala Ser Glu Asn Val Asp Thr Tyr
            20                  25                  30

Val Ser Trp Tyr Gln Gln Arg Pro Glu Gln Pro Pro Ala Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Gly Gly Thr Lys Leu Glu Leu Lys
            100                 105

<210> SEQ ID NO 78
<211> LENGTH: 107
<212> TYPE: PRT
<213> ORGANISM: Mus musculus

<400> SEQUENCE: 78

Asp Ile Val Met Thr Gln Ser Pro Lys Ser Met Gly Met Ser Val Gly
1               5                   10                  15

```
Glu Ala Val Thr Leu Asn Cys Lys Ala Ser Glu Asn Val Gly Thr Tyr
                20                  25                  30

Val Ser Trp Tyr Gln Gln Lys Pro Gly Gln Ser Pro Val Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Asp Asp Asp Ala Asp Tyr Tyr Cys Gly Gln Ser Tyr Ser Ser Pro Leu
                85                  90                  95

Thr Phe Gly Gly Gly Thr Lys Leu Glu Leu Lys
                100                 105

<210> SEQ ID NO 79
<211> LENGTH: 112
<212> TYPE: PRT
<213> ORGANISM: Mus musculus

<400> SEQUENCE: 79

Asp Ile Leu Met Thr Gln Thr Pro Ser Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

<210> SEQ ID NO 80
<211> LENGTH: 112
<212> TYPE: PRT
<213> ORGANISM: Mus musculus

<400> SEQUENCE: 80

Asp Ile Val Met Thr Gln Thr Pro Leu Ser Leu Pro Val Ser Leu Gly
1               5                   10                  15

Asp Lys Ala Ser Ile Ser Cys Arg Ser Ser Gln Ala Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Arg Thr Phe Gly Gly Gly Thr Lys Leu Glu Ile Lys
                100                 105                 110

<210> SEQ ID NO 81
<211> LENGTH: 112
```

```
<212> TYPE: PRT
<213> ORGANISM: Mus musculus

<400> SEQUENCE: 81

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
             20                  25                  30

Gly Asn Gln Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Pro
            100                 105                 110

<210> SEQ ID NO 82
<211> LENGTH: 108
<212> TYPE: PRT
<213> ORGANISM: Homo sapiens

<400> SEQUENCE: 82

Glu Ile Val Leu Thr Gln Ser Pro Gly Thr Leu Ser Leu Ser Pro Gly
 1               5                  10                  15

Glu Arg Ala Thr Phe Ser Cys Arg Ser Ser His Ser Ile Arg Ser Arg
             20                  25                  30

Arg Val Ala Trp Tyr Gln His Lys Pro Gly Gln Ala Pro Arg Leu Val
         35                  40                  45

Ile His Gly Val Ser Asn Arg Ala Ser Gly Ile Ser Asp Arg Phe Ser
     50                  55                  60

Gly Ser Gly Ser Gly Thr Asp Phe Thr Leu Thr Ile Thr Arg Val Glu
 65                  70                  75                  80

Pro Glu Asp Phe Ala Leu Tyr Tyr Cys Gln Val Tyr Gly Ala Ser Ser
                 85                  90                  95

Tyr Thr Phe Gly Gln Gly Thr Lys Leu Glu Arg Lys
            100                 105

<210> SEQ ID NO 83
<211> LENGTH: 112
<212> TYPE: PRT
<213> ORGANISM: Mus musculus

<400> SEQUENCE: 83

Asp Val Val Met Thr Gln Ser Pro Val Ser Leu Pro Val Ser Leu Gly
 1               5                  10                  15

Asp Gln Ala Ser Ile Ser Cys Arg Ser Ser Gln Ser Leu Gly His Ser
             20                  25                  30

Ser Gly Asn Thr Tyr Leu His Trp Phe Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Phe Lys Ile
 65                  70                  75                  80

Ser Arg Val Glu Ala Glu Asp Leu Gly Val Tyr Phe Cys Phe Gln Thr
                 85                  90                  95
```

Thr His Asp Pro Tyr Thr Phe Gly Gly Gly Thr Lys Leu Glu Ile Lys
        100                 105                 110

<210> SEQ ID NO 84
<211> LENGTH: 111
<212> TYPE: PRT
<213> ORGANISM: Mus musculus

<400> SEQUENCE: 84

Asp Val Val Leu Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Thr Phe Gly Gly Gly Thr Lys Leu Glu Ile Lys
        100                 105                 110

<210> SEQ ID NO 85
<211> LENGTH: 111
<212> TYPE: PRT
<213> ORGANISM: Mus musculus

<400> SEQUENCE: 85

Asp Ile Leu Met Thr Gln Thr Pro Leu Tyr Leu Pro Val Ser Leu Gly
1               5                   10                  15

Asp Gln Ala Ser Ile Ser Cys Arg Ser Ser Gln Thr Ile Val His Asn
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Phe Pro Pro Thr Phe Gly Gly Gly Thr Lys Leu Glu Ile
        100                 105                 110

<210> SEQ ID NO 86
<211> LENGTH: 112
<212> TYPE: PRT
<213> ORGANISM: Mus musculus

<400> SEQUENCE: 86

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Ser Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                     85                  90                  95

Ser His Ile Pro Phe Thr Phe Gly Ser Gly Thr Lys Leu Glu Ile Lys
                100                 105                 110

<210> SEQ ID NO 87
<211> LENGTH: 112
<212> TYPE: PRT
<213> ORGANISM: Mus musculus

<400> SEQUENCE: 87

Asp Ile Val Met Thr Gln Ala Ala Phe Ser Asn Pro Val Thr Leu Gly
  1               5                  10                  15

Thr Ser Ala Ser Ile Ser Cys Arg Ser Ser Lys Ser Leu Leu His Ser
                 20                  25                  30

Asn Gly Ile Thr Tyr Leu Tyr Trp Tyr Leu Gln Arg Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Asp Phe Ala Leu Arg Ile
 65                  70                  75                  80

Ser Arg Val Glu Ala Glu Asp Val Gly Val Tyr Tyr Cys Gly Gln Met
                     85                  90                  95

Leu Glu His Pro Leu Thr Phe Gly Thr Gly Thr Lys Leu Glu Leu Lys
                100                 105                 110

<210> SEQ ID NO 88
<211> LENGTH: 107
<212> TYPE: PRT
<213> ORGANISM: Mus musculus

<400> SEQUENCE: 88

Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Arg
                     85                  90                  95

Thr Phe Gly Gly Gly Thr Lys Leu Glu Ile Lys
                100                 105

<210> SEQ ID NO 89
<211> LENGTH: 112
<212> TYPE: PRT
<213> ORGANISM: Mus musculus

<400> SEQUENCE: 89

Asp Ile Gln Leu Thr Gln Ser Pro Ser Ser Leu Ala Val Ser Ala Gly
  1               5                  10                  15
```

```
Glu Lys Val Thr Met Asn Cys Lys Ser Ser Gln Asn Leu Leu His Ser
                20                  25                  30

Ile Thr Arg Lys Asn Tyr Leu Ala Trp Tyr Gln Lys Pro Gly Gln
            35                  40                  45

Ser Pro Lys Leu Leu Ile Tyr Trp Ala Ser Thr Arg Gly Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110
```

<210> SEQ ID NO 90
<211> LENGTH: 108
<212> TYPE: PRT
<213> ORGANISM: Homo sapiens

<400> SEQUENCE: 90

```
Glu Ile Val Leu Thr Gln Ser Pro Gly Thr Gln Ser Leu Ser Pro Gly
 1               5                  10                  15

Glu Arg Ala Thr Leu Ser Cys Arg Ala Ser Gln Ser Val Gly Asn Asn
                20                  25                  30

Lys Leu Ala Trp Tyr Gln Arg Pro Gly Gln Ala Pro Arg Leu Leu
            35                  40                  45

Ile Tyr Gly Ala Ser Ser Arg Pro Ser Gly Val Ala Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys
            100                 105
```

<210> SEQ ID NO 91
<211> LENGTH: 111
<212> TYPE: PRT
<213> ORGANISM: Mus musculus

<400> SEQUENCE: 91

```
Asp Ile Val Leu Thr Gln Ser Pro Ala Ser Leu Ala Val Ser Leu Gly
 1               5                  10                  15

Gln Pro Ala Thr Ile Ser Cys Gly Ala Ser Lys Ser Val Arg Thr Ser
                20                  25                  30

Gly Tyr Ser Tyr Met Asp Trp Asn Gln Gln Lys Pro Gly Gln Pro Pro
            35                  40                  45

Arg Arg Leu Ile Tyr Leu Val Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Ser His Ile Arg
                85                  90                  95

Glu Leu Pro Arg Ser Ser Gly Gly Gly Thr Lys Leu Glu Ile Lys
            100                 105                 110
```

<210> SEQ ID NO 92
<211> LENGTH: 107
<212> TYPE: PRT

<213> ORGANISM: Homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys
            100                 105

<210> SEQ ID NO 93
<211> LENGTH: 111
<212> TYPE: PRT
<213> ORGANISM: Mus musculus

<400> SEQUENCE: 93

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Leu Leu Ser
            20                  25                  30

Asp Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile
            100                 105                 110

<210> SEQ ID NO 94
<211> LENGTH: 112
<212> TYPE: PRT
<213> ORGANISM: Mus musculus

<400> SEQUENCE: 94

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

```
Ser His Val Pro Leu Thr Phe Gly Ala Gly Thr Lys Leu Glu Leu Lys
            100                 105                 110
```

<210> SEQ ID NO 95
<211> LENGTH: 112
<212> TYPE: PRT
<213> ORGANISM: Mus musculus

<400> SEQUENCE: 95

```
Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Ile Lys
            100                 105                 110
```

<210> SEQ ID NO 96
<211> LENGTH: 112
<212> TYPE: PRT
<213> ORGANISM: Mus musculus

<400> SEQUENCE: 96

```
Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
            100                 105                 110
```

<210> SEQ ID NO 97
<211> LENGTH: 105
<212> TYPE: PRT
<213> ORGANISM: Mus musculus

<400> SEQUENCE: 97

```
Ile Glu Leu Thr Gln Ser Pro Ser Ser Leu Ser Ala Ser Leu Gly Gly
  1               5                  10                  15

Lys Val Thr Ile Thr Cys Lys Ala Ser Gln Asp Ile Lys Lys Tyr Ile
             20                  25                  30

Gly Trp Tyr Gln His Lys Pro Gly Lys Gln Pro Arg Leu Leu Ile His
         35                  40                  45

Tyr Thr Ser Thr Leu Leu Pro Gly Ile Pro Ser Arg Phe Arg Gly Ser
     50                  55                  60
```

```
Gly Ser Gly Arg Asp Tyr Ser Phe Ser Ile Ser Asn Leu Glu Pro Glu
65                  70                  75                  80

Asp Ile Ala Thr Tyr Tyr Cys Leu Gln Tyr Tyr Asn Leu Arg Thr Phe
                85                  90                  95

Gly Gly Gly Thr Lys Leu Glu Ile Lys
            100                 105
```

<210> SEQ ID NO 98
<211> LENGTH: 112
<212> TYPE: PRT
<213> ORGANISM: Mus musculus

<400> SEQUENCE: 98

```
Asp Ile Val Leu Thr Gln Ala Ala Phe Ser Asn Pro Val Thr Leu Gly
1               5                   10                  15

Ala Ser Ala Ser Ile Ser Cys Arg Ser Ser Lys Ser Leu Leu Asn Ser
                20                  25                  30

Asn Gly Ile Ile His Met Tyr Trp Tyr Leu Gln Lys Pro Gly Gln Ser
            35                  40                  45

Pro Gln Leu Leu Ile Tyr Gln Met Ser Lys Leu Ala Ser Gly Ala Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110
```

<210> SEQ ID NO 99
<211> LENGTH: 111
<212> TYPE: PRT
<213> ORGANISM: Mus musculus

<400> SEQUENCE: 99

```
Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Val
                85                  90                  95

Thr His Val Pro Pro Thr Phe Gly Gly Gly Thr Lys Leu Glu Ile
            100                 105                 110
```

<210> SEQ ID NO 100
<211> LENGTH: 107
<212> TYPE: PRT
<213> ORGANISM: Mus musculus

<400> SEQUENCE: 100

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Tyr Tyr Met
```

```
                  20                  25                  30
Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Pro Ile
                 85                  90                  95

Thr Phe Gly Val Gly Thr Lys Leu Glu Leu Lys
            100                 105

<210> SEQ ID NO 101
<211> LENGTH: 107
<212> TYPE: PRT
<213> ORGANISM: Mus musculus

<400> SEQUENCE: 101

Asp Ile Glu Leu Thr Gln Ser Pro Ser Ser Met Ser Val Ser Leu Gly
 1               5                  10                  15

Asp Thr Val Ser Ile Thr Cys His Ala Ser Gln Gly Ile Ser Ser Asn
                 20                  25                  30

Ile Gly Trp Leu Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
     50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Val Gln Phe Pro Phe
                 85                  90                  95

Thr Phe Gly Ser Gly Thr Lys Leu Glu Ile Lys
            100                 105

<210> SEQ ID NO 102
<211> LENGTH: 111
<212> TYPE: PRT
<213> ORGANISM: Mus musculus

<400> SEQUENCE: 102

Glu Leu Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
            35                  40                  45

Pro Lys Phe Leu Ile Tyr Lys Val Ser Asn Arg Phe Ser Gly Val Pro
     50                  55                  60

Asp Arg Phe Gly Gly Ser Gly Ser Gly Thr Asp Phe Ile Leu Lys Ile
 65                  70                  75                  80

Ser Arg Val Glu Ala Glu Asp Leu Gly Val Tyr Phe Cys Phe Gln Ser
                 85                  90                  95

Thr His Phe Phe Pro Thr Phe Gly Gly Gly Thr Lys Leu Glu Ile
            100                 105                 110

<210> SEQ ID NO 103
<211> LENGTH: 112
<212> TYPE: PRT
<213> ORGANISM: Mus musculus
```

<400> SEQUENCE: 103

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
                100                 105                 110

<210> SEQ ID NO 104
<211> LENGTH: 107
<212> TYPE: PRT
<213> ORGANISM: Mus musculus

<400> SEQUENCE: 104

Ile Val Leu Thr Gln Ser Pro Thr Ile Met Ser Val Ser Pro Gly Glu
1               5                   10                  15

Lys Val Thr Leu Thr Cys Ser Ala Ser Ser Ser Val Ser Ser Asn Tyr
            20                  25                  30

Val Tyr Trp Tyr Gln Gln Lys Pro Gly Ser Ser Pro Lys Val Trp Ile
        35                  40                  45

Tyr Ser Thr Ser Asn Leu Ala Ser Gly Val Pro Ala Arg Phe Ser Gly
    50                  55                  60

Ser Gly Ser Gly Thr Ser Tyr Ser Leu Thr Ile Ser Ser Met Glu Ala
65                  70                  75                  80

Glu Asp Ala Ala Ser Tyr Phe Cys Leu Gln Trp Ser Ser Phe Pro Tyr
                85                  90                  95

Thr Phe Gly Gly Gly Thr Lys Leu Glu Leu Lys
                100                 105

<210> SEQ ID NO 105
<211> LENGTH: 107
<212> TYPE: PRT
<213> ORGANISM: Mus musculus

<400> SEQUENCE: 105

Glu Leu Val Met Thr Gln Thr Pro Ala Thr Leu Ser Val Thr Pro Gly
1               5                   10                  15

Asp Ser Val Ser Leu Ser Cys Arg Ala Ser Gln Ser Val Ser Asn Lys
            20                  25                  30

Leu His Trp Tyr Gln Gln Lys Ser His Glu Ser Pro Arg Leu Leu Ile
        35                  40                  45

Lys Phe Ala Ser Gln Ser Ile Pro Gly Ile Pro Ser Arg Phe Ser Gly
    50                  55                  60

Ser Gly Ser Gly Ser Asp Phe Thr Leu Ser Ile Asn Ser Val Glu Thr
65                  70                  75                  80

Glu Asp Phe Gly Ile Tyr Phe Cys His Gln Thr His Gly Arg Pro Leu
                85                  90                  95

Thr Phe Gly Ala Gly Thr Lys Leu Glu Leu Lys

<210> SEQ ID NO 106
<211> LENGTH: 111
<212> TYPE: PRT
<213> ORGANISM: Mus musculus

<400> SEQUENCE: 106

Asp Val Val Met Thr Gln Ile Pro Leu Ser Leu Pro Val Asn Leu Gly
1               5                   10                  15

Asp Gln Ala Ser Ile Ser Cys Arg Ser Ser Gln Ser Leu Ile His Ser
            20                  25                  30

Asn Gly Asn Thr Tyr Leu His Trp Tyr Leu Gln Lys Pro Gly Gln Ser
        35                  40                  45

Pro Lys Leu Leu Met Tyr Lys Val Ser Asn Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ser His Val Pro Pro Thr Phe Gly Gly Gly Thr Lys Leu Glu Ile
            100                 105                 110

<210> SEQ ID NO 107
<211> LENGTH: 106
<212> TYPE: PRT
<213> ORGANISM: Mus musculus

<400> SEQUENCE: 107

Asp Ile Glu Leu Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Tyr
            20                  25                  30

Ile Gly Trp Tyr Gln His Lys Pro Gly Lys Gly Pro Arg Leu Leu Ile
        35                  40                  45

His Tyr Thr Ser Thr Leu Leu Pro Gly Ile Pro Ser Arg Phe Arg Gly
    50                  55                  60

Ser Gly Ser Gly Arg Asp Tyr Ser Phe Ser Ile Ser Asn Leu Glu Gly
65                  70                  75                  80

Gly Asp Ile Ala Thr Tyr Tyr Cys Leu Gln Tyr Tyr Asn Leu Arg Thr
                85                  90                  95

Phe Gly Gly Gly Thr Lys Leu Glu Ile Lys
            100                 105

<210> SEQ ID NO 108
<211> LENGTH: 111
<212> TYPE: PRT
<213> ORGANISM: Mus musculus

<400> SEQUENCE: 108

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Thr Phe Gly Gly Gly Thr Lys Leu Glu Ile Lys
            100                 105                 110
```

<210> SEQ ID NO 109
<211> LENGTH: 112
<212> TYPE: PRT
<213> ORGANISM: Mus musculus

<400> SEQUENCE: 109

```
Asp Val Leu Met Thr Gln Thr Pro Leu Ser Leu Pro Val Ser Leu Gly
1               5                   10                  15

Asp Gln Val Ser Ile Ser Cys Arg Ser Ser Gln Ser Ile Phe His Ser
            20                  25                  30

Asp Gly Lys Thr Tyr Leu Glu Trp His Leu Gln Lys Pro Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 110
<211> LENGTH: 112
<212> TYPE: PRT
<213> ORGANISM: Mus musculus

<400> SEQUENCE: 110

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 111
<211> LENGTH: 106
<212> TYPE: PRT
<213> ORGANISM: Mus musculus

<400> SEQUENCE: 111

```
Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30
```

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu
            100                 105

<210> SEQ ID NO 112
<211> LENGTH: 110
<212> TYPE: PRT
<213> ORGANISM: Mus musculus

<400> SEQUENCE: 112

Ile Val Leu Thr Gln Ser Pro Ala Ser Leu Ala Val Ser Leu Gly Gln
 1               5                  10                  15

Arg Ala Thr Ile Ser Cys Arg Ala Ser Lys Ser Val Ser Thr Ser Gly
            20                  25                  30

Tyr Ser His Ile His Trp Tyr Gln Gln Lys Pro Gly Gln Pro Pro Lys
            35                  40                  45

Leu Leu Ile Tyr Leu Ala Ser Ile Leu Glu Ser Gly Val Pro Ala Arg
 50                  55                  60

Phe Ser Gly Ser Gly Ser Gly Thr Asp Phe Thr Leu Asn Ile His Pro
 65                  70                  75                  80

Val Glu Glu Glu Asp Ala Ala Thr Tyr Tyr Cys Gln His Ser Arg Glu
                85                  90                  95

Tyr Pro Leu Thr Phe Gly Ala Gly Thr Glu Leu Glu Leu Lys
            100                 105                 110

<210> SEQ ID NO 113
<211> LENGTH: 111
<212> TYPE: PRT
<213> ORGANISM: Mus musculus

<400> SEQUENCE: 113

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu Asn Trp Tyr Leu Gln Lys Ala Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Thr
                85                  90                  95

Thr His Val Pro Pro Thr Phe Gly Gly Gly Thr Lys Leu Glu Ile
            100                 105                 110

<210> SEQ ID NO 114
<211> LENGTH: 107
<212> TYPE: PRT
<213> ORGANISM: Mus musculus

```
<400> SEQUENCE: 114

Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Thr Tyr Tyr Cys His His Phe Trp Ser Thr Pro Trp
            85                  90                  95

Thr Phe Gly Gly Gly Thr Lys Leu Glu Val Lys
            100                 105

<210> SEQ ID NO 115
<211> LENGTH: 113
<212> TYPE: PRT
<213> ORGANISM: Mus musculus

<400> SEQUENCE: 115

Glu Val Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
            85                  90                  95

Thr His Val Pro Pro Leu Thr Phe Gly Ala Gly Thr Lys Leu Glu Leu
            100                 105                 110

Lys

<210> SEQ ID NO 116
<211> LENGTH: 112
<212> TYPE: PRT
<213> ORGANISM: Mus musculus

<400> SEQUENCE: 116

Asp Val Val Met Thr Gln Thr Pro Leu Ser Leu Ser Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Ser Arg Phe Ser Gly Phe Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
            85                  90                  95
```

```
Thr His Val Pro Phe Thr Phe Gly Ser Gly Thr Lys Leu Glu Ile Lys
            100                 105                 110
```

<210> SEQ ID NO 117
<211> LENGTH: 111
<212> TYPE: PRT
<213> ORGANISM: Mus musculus

<400> SEQUENCE: 117

```
Asp Val Val Val Thr Gln Thr Pro Leu Ser Leu Pro Val Ser Leu Gly
  1               5                  10                  15

Asp Gln Ala Ser Ile Ser Cys Arg Ser Ser Glu Val Ile Val Thr Arg
             20                  25                  30

Asn Gly Tyr Thr Pro Ile Glu Trp Tyr Leu Gln Lys Pro Gly Gln Ser
         35                  40                  45

Pro Lys Leu Leu Ile Tyr Lys Ala Tyr Lys Arg Phe Pro Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Asp Gly
                 85                  90                  95

Ser Thr Val Pro Pro Lys Phe Gly Gly Gly Thr Lys Leu Glu Ile
            100                 105                 110
```

<210> SEQ ID NO 118
<211> LENGTH: 112
<212> TYPE: PRT
<213> ORGANISM: Mus musculus

<400> SEQUENCE: 118

```
Asp Val Leu Met Thr Gln Thr Pro Leu Ser Leu Pro Val Ser Leu Gly
  1               5                  10                  15

Asp Gln Val Ser Ile Phe Cys Thr Ser Ser Gln Thr Ile Val His Thr
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Leu Gly Ile Tyr Tyr Cys Phe Gln Gly
                 85                  90                  95

Ser His Phe Pro Leu Ala Phe Gly Ala Gly Thr Lys Leu Glu Leu Lys
            100                 105                 110
```

<210> SEQ ID NO 119
<211> LENGTH: 107
<212> TYPE: PRT
<213> ORGANISM: Mus musculus

<400> SEQUENCE: 119

```
Asp Ile Val Met Thr Gln Ser Gln Lys Phe Met Ser Thr Ser Leu Gly
  1               5                  10                  15

Asn Arg Val Ser Val Thr Cys Lys Ala Ser Gln Asn Val Gly Thr Asn
             20                  25                  30

Val Ala Trp Phe Gln Gln Lys Pro Gly Gln Ser Pro Lys Thr Leu Ile
         35                  40                  45

Tyr Ser Ala Ser Tyr Arg Tyr Ser Gly Val Pro Asp Arg Phe Thr Gly
     50                  55                  60
```

```
Ser Gly Ser Gly Thr Asp Phe Thr Leu Thr Ile Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
            100                 105

<210> SEQ ID NO 120
<211> LENGTH: 112
<212> TYPE: PRT
<213> ORGANISM: Mus musculus

<400> SEQUENCE: 120

Asp Ile Val Met Thr Gln Ala Ala Pro Ser Val Ser Val Thr Pro Gly
 1               5                  10                  15

Glu Ser Val Ser Ile Ser Cys Arg Ser Ser Lys Ser Leu Leu His Ser
             20                  25                  30

Asn Gly Asn Thr Tyr Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Leu Gln His
                 85                  90                  95

Leu Glu Tyr Pro Phe Thr Phe Gly Ala Gly Thr Lys Leu Glu Leu Lys
            100                 105                 110

<210> SEQ ID NO 121
<211> LENGTH: 112
<212> TYPE: PRT
<213> ORGANISM: Mus musculus

<400> SEQUENCE: 121

Glu Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
             20                  25                  30

Asn Gly Asn Thr Tyr Leu Asn Trp Phe Leu Gln Arg Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Glu Thr Ala Phe Thr Leu Arg Thr
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ser Gly Thr Lys Leu Glu Leu Lys
            100                 105                 110

<210> SEQ ID NO 122
<211> LENGTH: 112
<212> TYPE: PRT
<213> ORGANISM: Mus musculus

<400> SEQUENCE: 122

Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
```

```
                    20                  25                  30
Asn Gly Asn Thr Tyr Leu Tyr Trp Phe Leu Gln Arg Pro Gly Gln Ser
                35                  40                  45
Pro Gln Leu Leu Ile Tyr Arg Met Ser Asn Leu Ala Ser Gly Val Pro
            50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Leu Gln His
                85                  90                  95
Leu Glu Tyr Pro Phe Thr Phe Gly Ala Gly Thr Lys Leu Glu Leu Lys
                100                 105                 110
```

<210> SEQ ID NO 123
<211> LENGTH: 112
<212> TYPE: PRT
<213> ORGANISM: Mus musculus

<400> SEQUENCE: 123

```
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Val His Ser
                20                  25                  30
Asn Gly Asn Thr Tyr Leu His Trp Tyr Leu Gln Lys Pro Gly Gln Ser
                35                  40                  45
Pro Lys Leu Leu Ile Tyr Lys Val Ser Asn Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Arg Thr Phe Gly Gly Gly Thr Lys Leu Glu Ile Lys
                100                 105                 110
```

<210> SEQ ID NO 124
<211> LENGTH: 104
<212> TYPE: PRT
<213> ORGANISM: Homo sapiens

<400> SEQUENCE: 124

```
Met Thr Gln Thr Pro Lys Phe Met Ser Thr Ser Val Gly Asp Arg Val
1               5                   10                  15
Ser Ile Thr Cys Lys Ala Ser Gln Asn Val Gly Thr Ala Val Ala Trp
                20                  25                  30
Tyr Gln Gln Lys Pro Gly Gln Ser Pro Lys Leu Leu Ile Tyr Ser Ala
                35                  40                  45
Ser Asn Arg Tyr Thr Gly Val Pro Asp Arg Phe Thr Gly Ser Gly Ser
            50                  55                  60
Gly Thr Asp Phe Thr Leu Thr Ile Ser Asn Met Gln Ser Glu Asp Leu
65                  70                  75                  80
Ala Asp Tyr Phe Cys Gln Gln Tyr Ser Ser Tyr Pro Leu Thr Phe Gly
                85                  90                  95
Gly Gly Thr Lys Val Glu Ile Lys
                100
```

<210> SEQ ID NO 125
<211> LENGTH: 112
<212> TYPE: PRT
<213> ORGANISM: Mus musculus -continued

<400> SEQUENCE: 125

Asp Val Val Met Thr Gln Ser Pro Lys Thr Ile Ser Val Thr Ile Gly
1               5                   10                  15

Gln Pro Ala Ser Ile Ser Cys Lys Ser Ser Gln Arg Leu Leu Asn Ser
            20                  25                  30

Asn Gly Lys Thr Phe Leu Asn Trp Leu Leu Gln Arg Pro Gly Gln Ser
        35                  40                  45

Pro Lys Arg Leu Ile Tyr Leu Gly Thr Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 126
<211> LENGTH: 112
<212> TYPE: PRT
<213> ORGANISM: Mus musculus

<400> SEQUENCE: 126

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Tyr Thr Tyr Leu His Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Phe
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 127
<211> LENGTH: 112
<212> TYPE: PRT
<213> ORGANISM: Mus musculus

<400> SEQUENCE: 127

Asp Val Val Met Thr Gln Ser Pro Lys Thr Ile Ser Val Thr Ile Gly
1               5                   10                  15

Gln Pro Ala Ser Ile Ser Cys Lys Ser Ser Gln Arg Leu Leu Asn Ser
            20                  25                  30

Asn Gly Lys Thr Phe Leu Asn Trp Leu Leu Gln Arg Pro Gly Gln Ser
        35                  40                  45

Pro Lys Arg Leu Ile Tyr Leu Gly Thr Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys

<210> SEQ ID NO 128
<211> LENGTH: 105
<212> TYPE: PRT
<213> ORGANISM: Mus musculus

<400> SEQUENCE: 128

Ile Val Leu Thr Gln Ser Pro Ala Ile Met Ser Ala Ser Leu Gly Ser
1               5                   10                  15

Ser Val Thr Leu Thr Cys Ser Ala Ser Ser Val Ser Tyr Met His
            20                  25                  30

Trp Tyr Gln Gln Lys Ser Gly Thr Ser Pro Val Leu Leu Ile Tyr Thr
        35                  40                  45

Thr Ser Asn Leu Ala Ser Gly Val Pro Ser Arg Phe Ser Gly Ser Gly
    50                  55                  60

Ser Gly Thr Phe Tyr Ser Leu Thr Ile Ser Ser Val Glu Ala Ser Asp
65                  70                  75                  80

Ala Ala Asp Tyr Tyr Cys His Gln Trp Ser Ser Tyr Pro Trp Thr Phe
                85                  90                  95

Gly Gly Gly Thr Lys Leu Glu Ile Lys
            100                 105

<210> SEQ ID NO 129
<211> LENGTH: 112
<212> TYPE: PRT
<213> ORGANISM: Mus musculus

<400> SEQUENCE: 129

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 130
<211> LENGTH: 111
<212> TYPE: PRT
<213> ORGANISM: Mus musculus

<400> SEQUENCE: 130

Asp Ile Val Met Thr Gln Ala Ala Phe Ser Asn Pro Val Thr Leu Gly
1               5                   10                  15

Thr Ser Ala Ser Ile Ser Cys Arg Ser Thr Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

```
Asn Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Pro Thr Phe Gly Gly Gly Thr Lys Leu Glu Ile
            100                 105                 110
```

<210> SEQ ID NO 131
<211> LENGTH: 107
<212> TYPE: PRT
<213> ORGANISM: Mus musculus

<400> SEQUENCE: 131

```
Glu Leu Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Leu
                 85                  90                  95

Thr Phe Gly Ala Gly Thr Lys Leu Glu Leu Lys
            100                 105
```

<210> SEQ ID NO 132
<211> LENGTH: 111
<212> TYPE: PRT
<213> ORGANISM: Mus musculus

<400> SEQUENCE: 132

```
Asp Ile Val Met Thr Gln Ser Pro Leu Thr Leu Ser Val Thr Ile Gly
 1               5                  10                  15

Gln Pro Ala Ser Ile Ser Cys Lys Ser Ser Gln Ser Leu Leu Tyr Ser
                 20                  25                  30

Asn Gly Lys Thr Tyr Leu Ser Trp Leu Leu Gln Arg Pro Gly Gln Ser
             35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Ala Asp Leu Gly Leu Tyr Tyr Cys Val Gln Gly
                 85                  90                  95

Thr His Phe Pro Tyr Thr Phe Gly Gly Gly Thr Lys Leu Glu Ile
            100                 105                 110
```

<210> SEQ ID NO 133
<211> LENGTH: 111
<212> TYPE: PRT
<213> ORGANISM: Mus musculus

<400> SEQUENCE: 133

```
Asp Ile Val Met Thr Gln Ser Pro Leu Thr Leu Ser Val Thr Ile Gly
 1               5                  10                  15

Gln Pro Ala Ser Ile Ser Cys Lys Ser Ser Gln Ser Leu Leu Tyr Ser
                 20                  25                  30
```

Asn Gly Lys Thr Tyr Leu Asn Trp Leu Leu Gln Arg Pro Gly Gln Ser
            35                  40                  45

Pro Lys Arg Leu Ile His Leu Val Ser Lys Leu Asp Ser Gly Val Pro
 50                  55                  60

Asp Arg Ile Thr Gly Ser Gly Ser Gly Thr Asp Phe Thr Leu Lys Ile
 65                  70                  75                  80

Ser Arg Val Glu Ala Ala Asp Leu Gly Val Tyr Tyr Cys Val Gln Gly
                 85                  90                  95

Thr His Phe Pro Tyr Thr Phe Gly Gly Gly Thr Lys Leu Glu Ile
            100                 105                 110

<210> SEQ ID NO 134
<211> LENGTH: 112
<212> TYPE: PRT
<213> ORGANISM: Mus musculus

<400> SEQUENCE: 134

Glu Leu Val Met Thr Gln Ser Pro Leu Ser Leu Pro Val Ser Leu Gly
 1               5                  10                  15

Asp Gln Ala Ser Ile Ser Cys Arg Pro Ser Gln Ser Leu Val His Ser
             20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Ala Phe Thr Leu Lys Ile
 65                  70                  75                  80

Ser Arg Val Glu Ala Glu Asp Leu Gly Val Tyr Phe Cys Ser Gln Gly
                 85                  90                  95

Thr His Val Pro Tyr Thr Phe Gly Gly Gly Thr Lys Leu Glu Leu Lys
            100                 105                 110

<210> SEQ ID NO 135
<211> LENGTH: 107
<212> TYPE: PRT
<213> ORGANISM: Mus musculus

<400> SEQUENCE: 135

Ile Val Leu Thr Gln Ser Pro Ala Ile Met Ser Ala Ser Leu Gly Glu
 1               5                  10                  15

Arg Val Thr Met Thr Cys Thr Ala Ser Ser Ser Val Ser Ser Ser Asn
             20                  25                  30

Leu His Trp Tyr Gln Gln Lys Pro Gly Ser Ser Pro Lys Leu Trp Ile
            35                  40                  45

Tyr Ser Thr Ser Asn Leu Ala Ser Gly Val Pro Ala Arg Phe Ser Gly
 50                  55                  60

Ser Gly Ser Gly Thr Ser Tyr Ser Leu Thr Ile Ser Ser Met Glu Ala
 65                  70                  75                  80

Glu Asp Ala Ala Thr Tyr Tyr Cys His Gln Tyr His Arg Ser Pro Tyr
                 85                  90                  95

Thr Phe Gly Gly Gly Thr Lys Leu Glu Ile Lys
            100                 105

<210> SEQ ID NO 136
<211> LENGTH: 112
<212> TYPE: PRT
<213> ORGANISM: Mus musculus

<400> SEQUENCE: 136

```
Asp Ile Val Ile Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Lys
            20                  25                  30

Asp Gly Arg Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Phe
                85                  90                  95

Val Glu Tyr Pro Phe Thr Phe Gly Ser Gly Thr Lys Leu Glu Ile Lys
            100                 105                 110
```

<210> SEQ ID NO 137
<211> LENGTH: 112
<212> TYPE: PRT
<213> ORGANISM: Mus musculus

<400> SEQUENCE: 137

```
Glu Leu Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Asp Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Val Gln Gly
                85                  90                  95

Ser His Phe Pro Pro Thr Phe Gly Ala Gly Thr Lys Leu Glu Leu Lys
            100                 105                 110
```

<210> SEQ ID NO 138
<211> LENGTH: 112
<212> TYPE: PRT
<213> ORGANISM: Mus musculus

<400> SEQUENCE: 138

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 139
<211> LENGTH: 111
<212> TYPE: PRT
<213> ORGANISM: Mus musculus

<400> SEQUENCE: 139

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Asp Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile
            100                 105                 110

<210> SEQ ID NO 140
<211> LENGTH: 112
<212> TYPE: PRT
<213> ORGANISM: Mus musculus

<400> SEQUENCE: 140

Asp Val Val Met Thr Gln Thr Pro Leu Thr Leu Ser Val Thr Ile Gly
1               5                   10                  15

Gln Pro Ala Ser Ile Ser Cys Arg Ser Ser Gln Ser Leu Leu Tyr Ile
            20                  25                  30

Asn Gly Lys Thr His Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Leu Gln Ser
                85                  90                  95

Thr His Phe Pro Leu Thr Phe Gly Ala Gly Thr Lys Leu Glu Leu Lys
            100                 105                 110

<210> SEQ ID NO 141
<211> LENGTH: 112
<212> TYPE: PRT
<213> ORGANISM: Mus musculus

<400> SEQUENCE: 141

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Thr Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Phe Gln Gly
                    85                  90                  95

Ser His Ile Pro Leu Thr Phe Gly Ala Gly Thr Lys Leu Glu Val Lys
                100                 105                 110

<210> SEQ ID NO 142
<211> LENGTH: 112
<212> TYPE: PRT
<213> ORGANISM: Mus musculus

<400> SEQUENCE: 142

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Thr Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                    85                  90                  95

Thr His Ala Pro Tyr Thr Phe Gly Gly Gly Thr Lys Leu Glu Ile Lys
                100                 105                 110

<210> SEQ ID NO 143
<211> LENGTH: 113
<212> TYPE: PRT
<213> ORGANISM: Mus musculus

<400> SEQUENCE: 143

Asp Val Val Met Thr Gln Thr Pro Ser Ser Leu Ala Met Ser Val Gly
1               5                   10                  15

Gln Lys Val Thr Met Ser Cys Lys Ser Ser Gln Ser Leu Leu Asn Ile
                20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Gln Ala Asp Tyr Phe Cys Gln Gln
                    85                  90                  95

His Tyr Arg Ala Pro Arg Thr Phe Gly Gly Gly Thr Lys Leu Glu Ile
                100                 105                 110

Lys

<210> SEQ ID NO 144
<211> LENGTH: 109
<212> TYPE: PRT
<213> ORGANISM: Mus musculus

<400> SEQUENCE: 144

Gln Val Gln Leu Gln Gln Ser Gly Ala Glu Leu Val Lys Pro Gly Ala
1               5                   10                  15

Ser Val Arg Met Ser Cys Lys Ala Ser Gly Tyr Thr Phe Thr Asn Tyr
```

```
                    20                  25                  30
Asn Met Tyr Trp Val Lys Gln Ser Pro Gly Gln Gly Leu Glu Trp Ile
        35                  40                  45

Gly Ile Phe Tyr Pro Gly Asn Gly Asp Thr Ser Tyr Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Trp Gly Gln Gly Thr Thr Val Thr Val
                100                 105

<210> SEQ ID NO 145
<211> LENGTH: 110
<212> TYPE: PRT
<213> ORGANISM: Mus musculus

<400> SEQUENCE: 145

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu His Thr Asp Thr Ala Arg Tyr Tyr Cys Ala
                85                  90                  95

Arg Asp Tyr Trp Gly Gln Gly Thr Thr Leu Thr Val Ser Ser
                100                 105                 110

<210> SEQ ID NO 146
<211> LENGTH: 111
<212> TYPE: PRT
<213> ORGANISM: Mus musculus

<400> SEQUENCE: 146

Glu Val Lys Leu Gln Glu Ser Gly Gly Asp Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Trp Val
        35                  40                  45

Ala Ser Ile Asn Asn Gly Gly Arg Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg Asp Tyr Trp Gly Gln Gly Thr Thr Val Thr Val Ser Ser
                100                 105                 110

<210> SEQ ID NO 147
<211> LENGTH: 110
<212> TYPE: PRT
<213> ORGANISM: Mus musculus
```

```
<400> SEQUENCE: 147

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30

Tyr Trp Ser Trp Ile Arg Lys Phe Pro Gly Asn Arg Leu Glu Tyr Met
        35                  40                  45

Gly Tyr Val Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Asp Tyr Trp Gly Gln Gly Thr Leu Val Thr Val Ser Ala
            100                 105                 110

<210> SEQ ID NO 148
<211> LENGTH: 111
<212> TYPE: PRT
<213> ORGANISM: Mus musculus

<400> SEQUENCE: 148

Gln Val Lys Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Asp Val Trp Gly Gln Gly Thr Thr Val Thr Val Ser Ser
            100                 105                 110

<210> SEQ ID NO 149
<211> LENGTH: 111
<212> TYPE: PRT
<213> ORGANISM: Mus musculus

<400> SEQUENCE: 149

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Tyr
            20                  25                  30

Tyr Met Lys Trp Val Lys His Ser His Gly Lys Ser Leu Glu Trp Ile
        35                  40                  45

Gly Asp Ile Asn Pro Ser Asn Gly Gly Thr Leu Tyr Asn Gln Lys Phe
    50                  55                  60

Lys Gly Lys Ala Thr Leu Thr Val Asp Lys Ser Ser Ser Thr Ala Ser
65                  70                  75                  80

Met Gln Leu Ser Arg Leu Thr Ser Glu Asp Ser Ala Val Tyr Tyr Cys
                85                  90                  95

Ser Arg Ala Tyr Trp Gly Gln Gly Thr Thr Val Thr Val Ser Ser
```

<210> SEQ ID NO 150
<211> LENGTH: 111
<212> TYPE: PRT
<213> ORGANISM: Mus musculus

<400> SEQUENCE: 150

Gln Val Gln Leu Gln Gln Ser Gly Ala Glu Leu Met Lys Pro Gly Pro
1               5                   10                  15

Ser Val Lys Ile Ser Cys Lys Ala Thr Gly Tyr Ser Phe Ser Thr Tyr
            20                  25                  30

Phe Ile Glu Trp Ile Arg Gln Arg Pro Gly His Gly Leu Glu Trp Ile
        35                  40                  45

Gly Glu Ile Leu Pro Gly Ser Asp Asn Thr Asn Phe Asn Glu Lys Phe
    50                  55                  60

Lys Asp Arg Ala Thr Phe Thr Ala Asp Thr Pro Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Trp Gly Gln Gly Thr Leu Val Thr Val Ser Ala
            100                 105                 110

<210> SEQ ID NO 151
<211> LENGTH: 109
<212> TYPE: PRT
<213> ORGANISM: Mus musculus

<400> SEQUENCE: 151

Val Lys Leu Val Gln Ser Gly Pro Gly Leu Val Ala Pro Ser Gln Ser
1               5                   10                  15

Leu Ser Ile Thr Cys Thr Val Ser Gly Phe Ser Leu Thr Thr Tyr Gly
            20                  25                  30

Val Ser Trp Val Arg Gln Pro Pro Gly Lys Gly Leu Glu Trp Leu Gly
        35                  40                  45

Val Ile Trp Gly Asp Gly Asn Thr Thr Tyr His Ser Ala Leu Ile Ser
    50                  55                  60

Arg Leu Ser Ile Ser Lys Asp Asn Ser Arg Ser Gln Val Phe Leu Lys
65                  70                  75                  80

Leu Asn Ser Leu His Thr Asp Asp Thr Ala Thr Tyr Tyr Cys Ala Gly
                85                  90                  95

Asp Tyr Trp Gly Gln Gly Thr Ser Val Thr Val Ser Ser
            100                 105

<210> SEQ ID NO 152
<211> LENGTH: 111
<212> TYPE: PRT
<213> ORGANISM: Mus musculus

<400> SEQUENCE: 152

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met Tyr Trp Val Lys Gln Ala Pro Gly Lys Gly Leu Lys Arg Met
            35                  40                  45

Gly Trp Ile Asn Thr Glu Thr Gly Glu Pro Thr Tyr Ala Asp Asp Phe
    50                  55                  60

```
Lys Gly Arg Phe Ala Leu Ser Leu Asp Thr Ser Ala Ser Thr Ala Tyr
 65                  70                  75                  80

Leu His Ile Ser Asn Leu Lys Asn Glu Asp Thr Ala Thr Tyr Phe Cys
                 85                  90                  95

Ala Arg Asp Ser Trp Gly Gln Gly Thr Ser Val Thr Val Ser Ser
            100                 105                 110

<210> SEQ ID NO 153
<211> LENGTH: 107
<212> TYPE: PRT
<213> ORGANISM: Mus musculus

<400> SEQUENCE: 153

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Asp Tyr
                20                  25                  30

Gly Val Asp Trp Val Arg Gln Pro Pro Gly Lys Gly Leu Glu Trp Leu
            35                  40                  45

Gly Met Ile Trp Gly Asp Gly Ser Thr Asp Tyr Asn Ser Ala Leu Lys
 50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Ala Arg Tyr Tyr Cys Val
                 85                  90                  95

Arg Asp Tyr Trp Gly Gln Gly Thr Ser Val Thr
            100                 105

<210> SEQ ID NO 154
<211> LENGTH: 110
<212> TYPE: PRT
<213> ORGANISM: Mus musculus

<400> SEQUENCE: 154

Gln Val Gln Leu Gln Gln Pro Gly Thr Glu Leu Val Arg Pro Gly Ala
 1               5                  10                  15

Ser Val Ile Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Val
            35                  40                  45

Gly Asn Ile Phe Pro Ser Asp Ser Tyr Thr Asn Tyr Asn Gln Lys Phe
 50                  55                  60

Lys Asp Lys Ala Thr Leu Thr Val Asp Lys Ser Ser Ser Thr Ala Tyr
 65                  70                  75                  80

Met Gln Val Asn Ser Pro Thr Ser Glu Asp Ser Ala Val Tyr Tyr Cys
                 85                  90                  95

Thr Arg Ala Tyr Trp Gly Gln Gly Thr Leu Val Thr Val Ser
            100                 105                 110

<210> SEQ ID NO 155
<211> LENGTH: 111
<212> TYPE: PRT
<213> ORGANISM: Mus musculus

<400> SEQUENCE: 155

Gln Asp Gln Leu Gln Gln Ser Gly Ala Glu Leu Val Arg Pro Gly Ala
 1               5                  10                  15

Ser Val Lys Leu Ser Cys Lys Ala Leu Gly Tyr Ile Phe Thr Asp Tyr
                20                  25                  30
```

Glu Ile His Trp Val Lys Gln Thr Pro Val His Gly Leu Glu Trp Ile
                35                  40                  45

Gly Gly Ile His Pro Gly Ser Ser Gly Thr Ala Tyr Asn Gln Lys Phe
        50                  55                  60

Lys Gly Lys Ala Thr Leu Thr Ala Asp Lys Ser Thr Thr Ala Phe
65                  70                  75                  80

Met Glu Leu Ser Ser Leu Thr Ser Glu Asp Ser Ala Val Tyr Tyr Cys
                85                  90                  95

Thr Arg Asp Tyr Trp Gly Gln Gly Thr Leu Val Thr Val Ser Ala
                100                 105                 110

<210> SEQ ID NO 156
<211> LENGTH: 111
<212> TYPE: PRT
<213> ORGANISM: Mus musculus

<400> SEQUENCE: 156

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
                35                  40                  45

Ala Tyr Ile Ser Ser Gly Ser Ser Thr Leu His Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Gly Met Tyr Tyr Cys
                85                  90                  95

Ala Arg Asp Tyr Trp Gly Gln Gly Thr Ser Val Thr Val Ser Ser
                100                 105                 110

<210> SEQ ID NO 157
<211> LENGTH: 111
<212> TYPE: PRT
<213> ORGANISM: Mus musculus

<400> SEQUENCE: 157

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Asn Ser Glu Lys Arg Leu Glu Trp Val
                35                  40                  45

Ala Phe Ile Ser Asn Gly Gly Gly Ser Ala Phe Tyr Ala Asp Ile Val
        50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Thr Arg Ala Asp Trp Gly Gln Gly Thr Leu Val Thr Val Ser Ala
                100                 105                 110

<210> SEQ ID NO 158
<211> LENGTH: 111
<212> TYPE: PRT
<213> ORGANISM: Homo sapiens

```
<400> SEQUENCE: 158

Gln Val Gln Leu Val Gln Ser Gly Ala Glu Val Lys Lys Pro Gly Ala
 1               5                   10                  15

Ser Val Lys Val Ser Cys Lys Val Ser Gly Tyr Thr Leu Thr Glu Leu
             20                  25                  30

Pro Val His Trp Val Arg Gln Ala Pro Gly Lys Gly Leu Glu Trp Val
         35                  40                  45

Gly Ser Phe Asp Pro Glu Ser Gly Glu Ser Ile Tyr Ala Arg Glu Phe
 50                  55                  60

Gln Gly Ser Val Thr Met Thr Ala Asp Thr Ser Thr Asn Ile Ala Tyr
65                   70                  75                  80

Met Glu Leu Ser Ser Leu Arg Ser Asp Asp Thr Ala Val Tyr Tyr Cys
                 85                  90                  95

Ala Val Asp Ile Trp Gly Gln Gly Thr Met Val Thr Val Ser Ser
            100                 105                 110

<210> SEQ ID NO 159
<211> LENGTH: 110
<212> TYPE: PRT
<213> ORGANISM: Mus musculus

<400> SEQUENCE: 159

Asp Val Gln Leu Gln Glu Ser Gly Pro Ser Leu Val Lys Pro Ser Gln
 1               5                   10                  15

Thr Leu Ser Leu Thr Cys Ser Val Thr Gly Asp Ser Ile Thr Ser Asp
             20                  25                  30

Tyr Trp Ser Trp Ile Arg Lys Phe Pro Gly Asn Arg Leu Glu Tyr Met
         35                  40                  45

Gly Tyr Val Ser Tyr Ser Gly Ser Thr Tyr Tyr Asn Pro Ser Leu Lys
 50                  55                  60

Ser Arg Ile Ser Ile Thr Arg Asp Thr Ser Lys Asn Gln Tyr Tyr Leu
65                   70                  75                  80

Asp Leu Asn Ser Val Thr Thr Glu Asp Thr Ala Thr Tyr Tyr Cys Ala
                 85                  90                  95

Asn Asp Tyr Trp Gly Gln Gly Thr Leu Val Thr Val Ser Ala
            100                 105                 110

<210> SEQ ID NO 160
<211> LENGTH: 109
<212> TYPE: PRT
<213> ORGANISM: Mus musculus

<400> SEQUENCE: 160

Gln Val Gln Leu Gln Gln Ser Gly Ala Glu Leu Val Arg Pro Gly Ala
 1               5                   10                  15

Ser Val Lys Leu Ser Cys Lys Ala Ser Gly Tyr Thr Phe Ile Ser Tyr
             20                  25                  30

Trp Ile Asn Trp Val Lys Gln Arg Pro Gly Gln Gly Leu Glu Trp Ile
         35                  40                  45

Gly Asn Ile Tyr Pro Ser Asp Ser Tyr Thr Asn Tyr Asn Gln Lys Phe
 50                  55                  60

Lys Asp Lys Ala Thr Leu Thr Val Asp Lys Ser Ser Ser Thr Ala Tyr
65                   70                  75                  80

Met Gln Leu Ser Ser Pro Thr Ser Glu Asp Ser Ala Val Tyr Tyr Cys
                 85                  90                  95

Thr Arg Asp Tyr Trp Gly Gln Gly Thr Thr Val Thr Val
            100                 105
```

<210> SEQ ID NO 161
<211> LENGTH: 111
<212> TYPE: PRT
<213> ORGANISM: Homo sapiens

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Gln Gly Thr Leu Val Thr Val Ser Ser
            100                 105                 110

<210> SEQ ID NO 162
<211> LENGTH: 111
<212> TYPE: PRT
<213> ORGANISM: Mus musculus

<400> SEQUENCE: 162

Val Lys Leu Gln Glu Ser Gly Pro Gly Ile Leu Lys Pro Ser Gln Thr
1               5                   10                  15

Leu Ser Leu Thr Cys Ser Phe Ser Gly Phe Ser Leu Thr Thr Tyr Gly
            20                  25                  30

Met Gly Val Gly Trp Ile Arg Gln Ser Ser Gly Lys Gly Leu Glu Trp
        35                  40                  45

Leu Ala His Ile Trp Trp Asp Asp Asp Lys Tyr Tyr Asn Pro Ser Leu
    50                  55                  60

Lys Ser Arg Leu Thr Ile Ser Lys Asp Thr Ser Arg Asn Gln Val Phe
65                  70                  75                  80

Leu Lys Ile Thr Ser Val Ala Thr Ala Asp Thr Ala Thr Tyr Tyr Cys
                85                  90                  95

Ala Arg Asp Tyr Trp Gly Gln Gly Thr Thr Val Thr Val Ser Ser
            100                 105                 110

<210> SEQ ID NO 163
<211> LENGTH: 109
<212> TYPE: PRT
<213> ORGANISM: Mus musculus

<400> SEQUENCE: 163

Val Ala Leu Gln Glu Ser Gly Pro Gly Leu Val Lys Pro Ser Gln Ser
1               5                   10                  15

Leu Ser Leu Thr Cys Thr Val Thr Gly Tyr Ser Ile Ser Asp Tyr Ala
            20                  25                  30

Trp Asn Trp Ile Arg Gln Phe Pro Gly Asn Lys Leu Glu Trp Met Gly
        35                  40                  45

Tyr Ile Arg Asn Gly Gly Ser Thr Thr Tyr Asn Pro Ser Leu Ala Ser
    50                  55                  60

Arg Ile Ser Ile Thr Arg Asp Thr Ser Lys Asn Gln Phe Phe Leu Gln

-continued

```
                 65                  70                  75                  80
Leu Asn Ser Val Thr Thr Glu Asp Thr Ala Thr Tyr Tyr Cys Ala Arg
                 85                  90                  95
Thr Tyr Trp Gly Ala Gly Thr Leu Val Thr Val Ser Ala
                100                 105

<210> SEQ ID NO 164
<211> LENGTH: 111
<212> TYPE: PRT
<213> ORGANISM: Mus musculus

<400> SEQUENCE: 164

Gln Val Gln Leu Gln Glu Ser Gly Ala Glu Val Met Lys Pro Gly Ala
  1               5                  10                  15
Ser Val Lys Ile Ser Cys Lys Ala Thr Gly Tyr Thr Phe Ser Thr Tyr
                 20                  25                  30
Trp Ile Glu Trp Val Lys Gln Arg Pro Gly His Gly Leu Glu Trp Ile
                 35                  40                  45
Gly Glu Ile Leu Pro Gly Ser Gly Ser Thr Tyr Tyr Asn Glu Lys Phe
         50                  55                  60
Lys Gly Lys Ala Thr Phe Thr Ala Asp Thr Ser Ser Asn Thr Ala Tyr
 65                  70                  75                  80
Met Gln Leu Ser Ser Leu Thr Ser Glu Asp Ser Ala Val Tyr Tyr Cys
                 85                  90                  95
Ala Arg Gly Tyr Trp Gly Gln Gly Thr Thr Leu Thr Val Ser Ser
                100                 105                 110

<210> SEQ ID NO 165
<211> LENGTH: 110
<212> TYPE: PRT
<213> ORGANISM: Mus musculus

<400> SEQUENCE: 165

Glu Val Gln Leu Gln Glu Ser Gly Pro Ser Leu Val Lys Pro Ser Gln
  1               5                  10                  15
Thr Leu Ser Leu Thr Cys Ser Val Thr Gly Asp Ser Val Thr Ser Asp
                 20                  25                  30
Tyr Trp Ser Trp Ile Arg Lys Phe Pro Gly Asn Lys Leu Glu Tyr Met
                 35                  40                  45
Gly Tyr Ile Ser Tyr Ser Gly Ser Thr Tyr Tyr His Pro Ser Leu Lys
         50                  55                  60
Ser Arg Ile Ser Ile Thr Arg Asp Thr Ser Lys Asn Gln Tyr Tyr Leu
 65                  70                  75                  80
Gln Leu Asn Ser Val Thr Thr Glu Asp Thr Ala Thr Tyr Tyr Cys Ala
                 85                  90                  95
Ser Asp Val Trp Gly Ala Gly Thr Thr Val Thr Val Ser Ser
                100                 105                 110

<210> SEQ ID NO 166
<211> LENGTH: 111
<212> TYPE: PRT
<213> ORGANISM: Mus musculus

<400> SEQUENCE: 166

Gln Ile Gln Leu Val Gln Ser Gly Pro Glu Leu Lys Lys Pro Gly Glu
  1               5                  10                  15
Thr Val Lys Ile Ser Cys Lys Ala Ser Gly Tyr Thr Phe Thr Asn Tyr
                 20                  25                  30
```

```
Gly Met Asn Trp Val Lys Gln Ala Pro Gly Lys Gly Leu Lys Trp Met
         35                  40                  45
Gly Trp Ile Asn Thr Asn Thr Gly Glu Pro Thr Tyr Gly Glu Glu Phe
 50                  55                  60
Lys Gly Arg Phe Ala Phe Ser Leu Glu Thr Ser Ala Ser Thr Ala Asn
 65                  70                  75                  80
Leu Gln Ile Asn Asn Leu Lys Asn Glu Asp Thr Ala Thr Phe Phe Cys
                 85                  90                  95
Ala Arg Asp Tyr Trp Gly Gln Gly Thr Thr Val Thr Val Ser Ser
                100                 105                 110
```

<210> SEQ ID NO 167
<211> LENGTH: 110
<212> TYPE: PRT
<213> ORGANISM: Mus musculus

<400> SEQUENCE: 167

```
Glu Val Gln Leu Gln Glu Ser Gly Pro Ser Leu Val Lys Pro Ser Gln
  1               5                  10                  15
Thr Leu Ser Leu Thr Cys Ser Val Thr Gly Asp Ser Ile Ile Arg Asp
                 20                  25                  30
Tyr Trp Ser Trp Ile Arg Lys Phe Pro Gly Asn Lys Leu Glu Tyr Met
         35                  40                  45
Gly Tyr Ile Ser Phe Ser Gly Asn Thr Phe Tyr His Pro Ser Leu Lys
 50                  55                  60
Ser Arg Ile Ser Ile Thr Arg Asp Thr Ser Lys Asn Gln His Tyr Leu
 65                  70                  75                  80
Gln Leu Ser Ser Val Thr Thr Glu Asp Thr Ala Thr Tyr Tyr Cys Ala
                 85                  90                  95
Asn Thr Tyr Trp Gly Glu Gly Thr Leu Val Thr Val Ser Ala
                100                 105                 110
```

<210> SEQ ID NO 168
<211> LENGTH: 111
<212> TYPE: PRT
<213> ORGANISM: Mus musculus

<400> SEQUENCE: 168

```
Glu Leu Gln Leu Val Gln Ser Gly Pro Gln Leu Lys Lys Pro Gly Glu
  1               5                  10                  15
Thr Val Arg Ile Ser Cys Lys Ala Ser Gly Tyr Thr Phe Thr Thr Ala
                 20                  25                  30
Gly Ile Gln Trp Val Gln Arg Leu Pro Gly Lys Asp Leu Lys Trp Ile
         35                  40                  45
Gly Trp Ile Asn Thr His Ser Gly Val Pro Gln Tyr Ala Asp Asp Phe
 50                  55                  60
Lys Gly Arg Phe Ala Phe Ser Leu Glu Thr Ser Ala Ser Thr Ala Phe
 65                  70                  75                  80
Leu Gln Ile Ile Asn Leu Lys Asn Glu Asp Thr Ala Thr Tyr Phe Cys
                 85                  90                  95
Ala Arg Asp Phe Trp Gly Gln Gly Thr Ser Val Thr Val Ser Ser
                100                 105                 110
```

<210> SEQ ID NO 169
<211> LENGTH: 110
<212> TYPE: PRT
<213> ORGANISM: Mus musculus

<400> SEQUENCE: 169

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Asn Asn Tyr
             20                  25                  30

Ala Trp Asn Trp Ile Arg Gln Phe Pro Gly Asn Lys Leu Glu Trp Met
             35                  40                  45

Gly Tyr Ile Asn Tyr Ser Gly Thr Thr Ser Tyr Asn Pro Ser Leu Lys
 50                  55                  60

Ser Arg Ile Ser Ile Thr Arg Asp Thr Ser Lys Asn Gln Phe Phe Leu
 65                  70                  75                  80

Gln Leu Asn Ser Val Thr Thr Glu Asp Thr Ala Thr Tyr Phe Cys Val
                 85                  90                  95

Arg Asp Tyr Trp Gly Gln Gly Thr Ser Val Thr Val Ser Ser
            100                 105                 110
```

<210> SEQ ID NO 170
<211> LENGTH: 110
<212> TYPE: PRT
<213> ORGANISM: Mus musculus

<400> SEQUENCE: 170

```
Glu Val Gln Leu Gln Glu Ser Gly Pro Ser Leu Val Lys Pro Ser Gln
 1               5                  10                  15

Thr Leu Ser Leu Thr Cys Ser Val Thr Gly Glu Pro Ile Thr Ser Gly
             20                  25                  30

Phe Trp Asp Trp Ile Arg Lys Phe Pro Gly Asn Lys Leu Glu Phe Met
             35                  40                  45

Gly Tyr Ile Arg Tyr Gly Gly Gly Thr Tyr Tyr Asn Pro Ser Leu Lys
 50                  55                  60

Ser Pro Ile Ser Ile Thr Arg Asp Thr Ser Lys Asn His Tyr Tyr Leu
 65                  70                  75                  80

Gln Leu Asn Ser Val Val Thr Glu Asp Thr Ala Thr Tyr Tyr Cys Ala
                 85                  90                  95

Arg Ala Phe Trp Gly Glu Gly Thr Leu Val Thr Val Ser Ala
            100                 105                 110
```

<210> SEQ ID NO 171
<211> LENGTH: 110
<212> TYPE: PRT
<213> ORGANISM: Mus musculus

<400> SEQUENCE: 171

```
Val Arg Leu Leu Glu Ser Gly Gly Gly Leu Val Gln Pro Gly Gly Ser
 1               5                  10                  15

Leu Lys Leu Ser Cys Ala Ala Ser Gly Phe Asp Tyr Ser Arg Tyr Trp
             20                  25                  30

Met Ser Trp Val Arg Gln Ala Pro Gly Lys Gly Leu Lys Trp Ile Gly
             35                  40                  45

Glu Ile Asn Pro Val Ser Ser Thr Ile Asn Tyr Thr Pro Ser Leu Lys
 50                  55                  60

Asp Lys Phe Ile Ile Ser Arg Asp Asn Ala Lys Asp Thr Leu Tyr Leu
 65                  70                  75                  80

Gln Ile Ser Lys Val Arg Ser Glu Asp Thr Ala Leu Tyr Tyr Cys Ala
                 85                  90                  95

Arg Asp Val Trp Gly Ala Gly Thr Thr Val Thr Val Ser Ser
            100                 105                 110
```

-continued

<210> SEQ ID NO 172
<211> LENGTH: 111
<212> TYPE: PRT
<213> ORGANISM: Mus musculus

<400> SEQUENCE: 172

Glu Val Gln Leu Gln Glu Ser Gly Ala Glu Leu Met Lys Pro Gly Ala
1               5                   10                  15

Ser Val Lys Ile Ser Cys Lys Ala Thr Gly Tyr Thr Phe Thr Thr Tyr
            20                  25                  30

Trp Ile Glu Trp Ile Lys Gln Arg Pro Gly His Ser Leu Glu Trp Ile
        35                  40                  45

Gly Glu Ile Leu Pro Gly Ser Asp Ser Thr Tyr Tyr Asn Glu Lys Val
    50                  55                  60

Lys Gly Lys Val Thr Phe Thr Ala Asp Ala Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Val Tyr Trp Gly Gln Gly Thr Thr Leu Thr Val Ser Ser
            100                 105                 110

<210> SEQ ID NO 173
<211> LENGTH: 111
<212> TYPE: PRT
<213> ORGANISM: Mus musculus

<400> SEQUENCE: 173

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Leu Thr Thr Tyr
            20                  25                  30

Trp Met Asn Trp Phe Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Arg Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Tyr Trp Gly Gln Gly Thr Ser Val Thr Val Ser Ser
            100                 105                 110

<210> SEQ ID NO 174
<211> LENGTH: 111
<212> TYPE: PRT
<213> ORGANISM: Mus musculus

<400> SEQUENCE: 174

Asp Val Lys Leu Val Glu Ser Gly Gly Gly Leu Val Lys Pro Gly Arg
1               5                   10                  15

Ser Leu Lys Leu Ser Cys Ala Ala Ser Gly Phe Thr Phe Ser Asp Tyr
            20                  25                  30

Tyr Met Phe Trp Val Arg Gln Thr Pro Glu Gln Arg Leu Glu Trp Val
        35                  40                  45

Ala Thr Ile Ser Asp Gly Gly Ala Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Lys Ser Glu Asp Thr Gly Met Tyr Tyr Cys
                    85                  90                  95

Ala Arg Asp Tyr Trp Gly Gln Gly Thr Ser Val Ala Val Ser Ser
                100                 105                 110

<210> SEQ ID NO 175
<211> LENGTH: 112
<212> TYPE: PRT
<213> ORGANISM: Mus musculus

<400> SEQUENCE: 175

Gln Ile Thr Leu Lys Glu Ser Gly Pro Gly Ile Val Gln Pro Ser Gln
1               5                   10                  15

Pro Phe Arg Leu Thr Cys Thr Phe Ser Gly Phe Ser Leu Ser Thr Ser
                20                  25                  30

Gly Ile Gly Val Thr Trp Ile Arg Gln Pro Ser Gly Lys Gly Leu Glu
            35                  40                  45

Trp Leu Ala Thr Ile Trp Trp Asp Asp Asp Asn Arg Tyr Asn Pro Ser
    50                  55                  60

Leu Lys Ser Arg Leu Thr Val Ser Lys Asp Thr Ser Asn Asn Gln Ala
65                  70                  75                  80

Phe Leu Asn Met Met Thr Val Glu Thr Ala Asp Thr Ala Ile Tyr Tyr
                85                  90                  95

Cys Ala Gln Asp His Trp Gly Gln Gly Thr Ser Val Thr Val Ser Ser
                100                 105                 110

<210> SEQ ID NO 176
<211> LENGTH: 111
<212> TYPE: PRT
<213> ORGANISM: Mus musculus

<400> SEQUENCE: 176

Gln Val Gln Leu Gln Gln Pro Gly Ser Val Leu Val Arg Pro Gly Ala
1               5                   10                  15

Ser Val Lys Leu Ser Cys Lys Ala Ser Gly Phe Thr Phe Thr Ser Ser
                20                  25                  30

Trp Met His Trp Ala Lys Gln Arg Pro Gly Gln Gly Leu Glu Trp Ile
            35                  40                  45

Gly Glu Ile His Pro Asn Ser Gly Asn Thr His Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Asp Asn Trp Gly Gln Gly Thr Ser Val Thr Val Ser Ser
                100                 105                 110

<210> SEQ ID NO 177
<211> LENGTH: 110
<212> TYPE: PRT
<213> ORGANISM: Homo sapiens

<400> SEQUENCE: 177

Arg Ile Thr Leu Lys Glu Ser Gly Pro Leu Val Lys Pro Thr Gln
1               5                   10                  15

Thr Leu Thr Leu Thr Cys Ser Phe Ser Gly Phe Ser Leu Ser Asp Phe
                20                  25                  30

Gly Val Gly Val Gly Trp Ile Arg Gln Pro Pro Gly Lys Ala Leu Glu

```
                    35                  40                  45
Trp Leu Ala Ile Ile Tyr Ser Asp Asp Asp Lys Arg Tyr Ser Pro Ser
 50                  55                  60

Leu Asn Thr Arg Leu Thr Ile Thr Lys Asp Thr Ser Lys Asn Gln Val
 65                  70                  75                  80

Val Leu Val Met Thr Arg Val Ser Pro Val Asp Thr Ala Thr Tyr Phe
                 85                  90                  95

Cys Ala His Asp Val Trp Gly Gln Gly Ile Thr Val Thr Ile
                100                 105                 110

<210> SEQ ID NO 178
<211> LENGTH: 111
<212> TYPE: PRT
<213> ORGANISM: Mus musculus

<400> SEQUENCE: 178

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Leu Val Lys Gln Ala Pro Gly Lys Gly Phe Glu Trp Met
             35                  40                  45

Gly Trp Ile Asn Thr Phe Thr Gly Glu Pro Thr Tyr Ala Asp Asp Phe
 50                  55                  60

Lys Gly Arg Phe Val Phe Ser Leu Asp Thr Ser Ala Ser Thr Ala Tyr
 65                  70                  75                  80

Leu Gln Ile Asn Asn Leu Lys Asn Glu Asp Thr Ala Thr Tyr Phe Phe
                 85                  90                  95

Thr Arg Asp Tyr Trp Gly Gln Gly Thr Thr Leu Thr Val Ser Ser
                100                 105                 110

<210> SEQ ID NO 179
<211> LENGTH: 111
<212> TYPE: PRT
<213> ORGANISM: Mus musculus

<400> SEQUENCE: 179

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                20                  25                  30

Tyr Val His Trp Val Lys Gln Arg Pro Glu Gln Gly Leu Glu Trp Ile
             35                  40                  45

Gly Arg Ile Asp Pro Ala Asn Gly Tyr Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Val Arg Asp Tyr Trp Gly Gln Gly Thr Ser Val Thr Val Ser Ser
                100                 105                 110

<210> SEQ ID NO 180
<211> LENGTH: 111
<212> TYPE: PRT
<213> ORGANISM: Mus musculus

<400> SEQUENCE: 180
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Tyr Asp Asp
            20                  25                  30

Asp Ile His Trp Val Arg Gln Ala Pro Gly Lys Gly Leu Glu Trp Val
        35                  40                  45

Ala Tyr Ile Ala Pro Ser Tyr Gly Tyr Thr Tyr Ala Asp Ser Val
50                      55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Tyr Trp Gly Gln Gly Thr Leu Val Thr Val Ser Ser
            100                 105                 110

<210> SEQ ID NO 181
<211> LENGTH: 111
<212> TYPE: PRT
<213> ORGANISM: Mus musculus

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Tyr Asp Tyr
            20                  25                  30

Asp Ile His Trp Val Arg Gln Ala Pro Gly Lys Gly Leu Glu Trp Val
        35                  40                  45

Ala Asp Ile Ala Pro Tyr Ala Gly Ala Thr Ala Tyr Ala Asp Ser Val
50                      55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Tyr Trp Gly Gln Gly Thr Leu Val Thr Val Ser Ser
            100                 105                 110

<210> SEQ ID NO 182
<211> LENGTH: 111
<212> TYPE: PRT
<213> ORGANISM: Homo sapiens

<400> SEQUENCE: 182

Gln Val Gln Leu Leu Glu Ser Gly Ala Val Leu Ala Arg Pro Gly Thr
1               5                   10                  15

Ser Val Lys Ile Ser Cys Lys Ala Ser Gly Phe Asn Ile Lys Asp Tyr
            20                  25                  30

Tyr Met His Trp Val Lys Gln Arg Pro Gly Gln Gly Leu Glu Trp Ile
        35                  40                  45

Gly Gly Asn Asp Pro Ala Asn Gly His Ser Met Tyr Asp Pro Lys Phe
50                      55                  60

Gln Gly Arg Val Thr Ile Thr Ala Asp Thr Ser Ser Thr Val Phe
65                  70                  75                  80

Met Glu Leu Ser Ser Leu Arg Ser Glu Asp Thr Ala Val Tyr Tyr Cys
                85                  90                  95

Ala Arg Asp Tyr Trp Gly Gln Gly Thr Leu Val Thr Val Ser Ser
            100                 105                 110

```
<210> SEQ ID NO 183
<211> LENGTH: 110
<212> TYPE: PRT
<213> ORGANISM: Mus musculus

<400> SEQUENCE: 183

Val Gln Leu Gln Gln Ser Gly Pro Glu Leu Lys Lys Pro Gly Glu Thr
1               5                   10                  15
Val Lys Leu Ser Cys Lys Ala Ser Gly Tyr Thr Phe Thr Asn Phe Gly
                20                  25                  30
Leu Asn Trp Met Lys Gln Ala Pro Gly Lys Gly Leu Lys Trp Met Gly
            35                  40                  45
Trp Ile Asn Thr Tyr Thr Gly Glu Ser Thr Tyr Ala Asp Asp Phe Lys
        50                  55                  60
Gly Arg Phe Ala Phe Ser Leu Glu Thr Ser Ala Ser Thr Ala Tyr Leu
65                  70                  75                  80
Gln Ile Asn Asn Val Lys Asn Glu Asp Thr Ala Thr Tyr Phe Cys Ala
                85                  90                  95
Arg Asp Tyr Trp Gly Gln Gly Thr Thr Leu Thr Val Ser Ser
            100                 105                 110

<210> SEQ ID NO 184
<211> LENGTH: 111
<212> TYPE: PRT
<213> ORGANISM: Mus musculus

<400> SEQUENCE: 184

Glu Val Lys Leu Leu Glu Ser Gly Gly Gly Leu Val Gln Pro Gly Gly
1               5                   10                  15
Ser Gln Lys Leu Ser Cys Ala Ala Ser Gly Phe Asp Phe Ser Gly Tyr
                20                  25                  30
Trp Met Ser Trp Val Arg Gln Ala Pro Gly Lys Gly Leu Glu Trp Ile
            35                  40                  45
Gly Glu Ile Asn Pro Asp Ser Ser Thr Ile Asn Tyr Thr Pro Ser Leu
        50                  55                  60
Lys Asp Lys Phe Ile Ile Ser Arg Asp Asn Ala Lys Asn Thr Leu Tyr
65                  70                  75                  80
Leu Gln Met Ser Lys Val Arg Ser Glu Asp Thr Ala Leu Tyr Tyr Cys
                85                  90                  95
Ala Arg Asp Tyr Trp Gly Gln Gly Thr Thr Leu Thr Val Ser Ser
            100                 105                 110

<210> SEQ ID NO 185
<211> LENGTH: 113
<212> TYPE: PRT
<213> ORGANISM: Mus musculus

<400> SEQUENCE: 185

Glu Val Lys Leu Glu Glu Ser Gly Gly Gly Leu Val Gln Pro Gly Gly
1               5                   10                  15
Ser Met Lys Leu Ser Cys Ala Ala Ser Gly Phe Thr Phe Ser Asp Ala
                20                  25                  30
Trp Met Asp Trp Val Arg Gln Ser Pro Glu Lys Gly Leu Glu Trp Val
            35                  40                  45
Ala Glu Ile Arg Ser Lys Val Asn Asn His Ala Ile His Tyr Ala Glu
        50                  55                  60
Ser Val Lys Gly Arg Phe Thr Val Ser Arg Asp Asp Ser Lys Ser Ser
65                  70                  75                  80
```

```
Val Tyr Leu Gln Met Asn Ser Leu Arg Ala Glu Asp Thr Gly Ile Tyr
                85                  90                  95

Tyr Cys Ser Gly Leu Tyr Trp Gly Gln Gly Thr Leu Val Thr Val Ser
            100                 105                 110

Ala

<210> SEQ ID NO 186
<211> LENGTH: 111
<212> TYPE: PRT
<213> ORGANISM: Mus musculus

<400> SEQUENCE: 186

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Lys Gly Leu Glu Trp Ile
        35                  40                  45

Gly Arg Ile Asp Pro Ala Ser Gly Asn Thr Lys Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Gly Asp Tyr Trp Gly Gln Gly Thr Thr Leu Thr Val Ser Ser
            100                 105                 110

<210> SEQ ID NO 187
<211> LENGTH: 111
<212> TYPE: PRT
<213> ORGANISM: Mus musculus

<400> SEQUENCE: 187

Glu Val Gln Leu Gln Gln Ser Gly Ala Glu Leu Met Lys Pro Gly Ala
1               5                   10                  15

Ser Val Lys Ile Ser Cys Lys Ala Ser Gly Tyr Thr Phe Ser Asp Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr His Glu Arg Phe
    50                  55                  60

Lys Gly Lys Ala Thr Phe Thr Ala Asp Thr Ser Ser Thr Ala Tyr
65                  70                  75                  80

Met Gln Leu Asn Ser Leu Thr Ser Glu Asp Ser Gly Val Tyr Tyr Cys
                85                  90                  95

Leu His Asp Gly Trp Gly Gln Gly Thr Thr Leu Thr Val Ser Ser
            100                 105                 110

<210> SEQ ID NO 188
<211> LENGTH: 111
<212> TYPE: PRT
<213> ORGANISM: Mus musculus

<400> SEQUENCE: 188

Gln Val Gln Leu Gln Gln Ser Gly Ser Glu Leu Met Lys Pro Gly Ala
1               5                   10                  15

Ser Val Gln Ile Ser Cys Lys Ala Thr Gly Tyr Thr Phe Ser Asp Tyr
            20                  25                  30
```

Trp Ile Glu Trp Val Lys Gln Arg Pro Gly His Gly Leu Glu Trp Ile
    35                  40                  45

Gly Asp Ile Leu Cys Gly Thr Gly Arg Thr Arg Tyr Asn Glu Lys Leu
50                      55                  60

Lys Ala Met Ala Thr Phe Thr Ala Asp Thr Ser Ser Asn Thr Ala Phe
65                  70                  75                  80

Met Gln Leu Ser Ser Leu Thr Ser Glu Asp Ser Ala Val Tyr Tyr Cys
                85                  90                  95

Ala Arg Asp Tyr Trp Gly His Gly Thr Thr Leu Thr Val Ser Ser
            100                 105                 110

<210> SEQ ID NO 189
<211> LENGTH: 111
<212> TYPE: PRT
<213> ORGANISM: Mus musculus

<400> SEQUENCE: 189

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Lys Asn Thr Asn Thr Gly Glu Thr Thr Tyr Gly Glu Glu Phe
50                  55                  60

Arg Gly Arg Phe Ala Phe Ser Leu Glu Thr Ser Val Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Tyr Trp Gly Gln Gly Thr Thr Val Thr Val Ser Ser
            100                 105                 110

<210> SEQ ID NO 190
<211> LENGTH: 113
<212> TYPE: PRT
<213> ORGANISM: Mus musculus

<400> SEQUENCE: 190

Glu Val Lys Leu Val Glu Ser Gly Gly Gly Leu Val Gln Pro Gly Gly
1               5                   10                  15

Ser Leu Ser Leu Ser Cys Ala Thr Ser Gly Phe Thr Phe Ile Asp Tyr
            20                  25                  30

Tyr Met Ser Trp Phe Arg Gln Pro Pro Gly Lys Ala Leu Glu Trp Leu
        35                  40                  45

Gly Leu Ile Arg Asn Lys Gly Asn Gly Tyr Thr Met Glu Tyr Ser Ala
50                  55                  60

Ser Leu Lys Gly Arg Phe Thr Ile Ser Arg Asp Asn Ser Gln Ser Ile
65                  70                  75                  80

Val Tyr Leu His Met Asn Thr Leu Thr Ala Glu Asp Ser Ala Thr Tyr
                85                  90                  95

Tyr Cys Ala Arg Asp Tyr Trp Gly Gln Gly Thr Thr Leu Thr Val Ser
            100                 105                 110

Ser

<210> SEQ ID NO 191
<211> LENGTH: 111
<212> TYPE: PRT
<213> ORGANISM: Mus musculus

<400> SEQUENCE: 191

Glu Val Gln Leu Gln Gln Ser Gly Ala Glu Leu Val Lys Ala Gly Ala
1               5                   10                  15

Ser Val Lys Leu Ser Cys Pro Ala Ser Gly Leu Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Asp Tyr Trp Gly Gln Gly Thr Thr Leu Thr Val Ser Ser
            100                 105                 110

<210> SEQ ID NO 192
<211> LENGTH: 110
<212> TYPE: PRT
<213> ORGANISM: Mus musculus

<400> SEQUENCE: 192

Val Gln Leu Glu Gln Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Ala Asp Asp Phe Lys
    50                  55                  60

Glu Arg Phe Ala Phe Ser Leu Glu Thr Ser Ala Ser Ala Ala Tyr Leu
65                  70                  75                  80

Gln Ile Asn Asn Leu Lys Asn Glu Asp Thr Ala Thr Tyr Phe Cys Ala
                85                  90                  95

Arg Asp Tyr Trp Gly Gln Gly Thr Thr Val Thr Val Ser Ser
            100                 105                 110

<210> SEQ ID NO 193
<211> LENGTH: 109
<212> TYPE: PRT
<213> ORGANISM: Homo sapiens

<400> SEQUENCE: 193

Gln Leu Val Gln Ser Gly Ala Glu Val Arg Lys Pro Gly Ala Ser Val
1               5                   10                  15

Lys Val Ser Cys Lys Ala Ser Gly Asp Thr Phe Ser Ser Tyr Ala Ile
            20                  25                  30

Ser Trp Val Arg Gln Ala Pro Gly Gln Gly Leu Glu Trp Met Gly Gly
        35                  40                  45

Ile Ile Pro Ile Phe Gly Thr Ala Asn Tyr Ala Gln Ala Phe Gln Gly
    50                  55                  60

Arg Val Thr Ile Thr Ala Asn Glu Ser Ser Thr Ala Tyr Met Glu
65                  70                  75                  80

Leu Ser Ser Leu Arg Ser Glu Asp Thr Ala Ile Tyr Tyr Cys Ala Arg
                85                  90                  95

Asp Tyr Trp Gly Ala Gly Thr Leu Val Thr Val Ser Ser

<210> SEQ ID NO 194
<211> LENGTH: 110
<212> TYPE: PRT
<213> ORGANISM: Mus musculus

<400> SEQUENCE: 194

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30

Phe Trp Ser Trp Ile Arg Lys Phe Pro Gly Asn Arg Leu Glu Tyr Met
        35                  40                  45

Gly Tyr Val Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Asp Tyr Trp Gly Gln Gly Thr Leu Val Thr Val Ser Ala
            100                 105                 110

<210> SEQ ID NO 195
<211> LENGTH: 110
<212> TYPE: PRT
<213> ORGANISM: Mus musculus

<400> SEQUENCE: 195

Val Lys Leu Gln Gln Ser Gly Pro Glu Val Val Lys Pro Gly Ala Ser
1               5                   10                  15

Val Lys Ile Ser Cys Lys Ala Ser Gly Tyr Ser Phe Thr Asn Phe Tyr
            20                  25                  30

Ile His Trp Val Lys Gln Arg Pro Gly Gln Gly Leu Glu Trp Ile Gly
        35                  40                  45

Trp Ile Phe His Gly Ser Asp Asn Thr Glu Tyr Asn Glu Lys Phe Lys
    50                  55                  60

Asp Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Asp Val Trp Gly Gln Gly Thr Thr Val Thr Val Ser Ser
            100                 105                 110

<210> SEQ ID NO 196
<211> LENGTH: 111
<212> TYPE: PRT
<213> ORGANISM: Homo sapiens

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

-continued

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Trp Gly Gln Gly Thr Leu Val Thr Val Ser Ser
            100                 105                 110

<210> SEQ ID NO 197
<211> LENGTH: 113
<212> TYPE: PRT
<213> ORGANISM: Mus musculus

<400> SEQUENCE: 197

Glu Val Asn Leu Val Glu Ser Gly Gly Gly Leu Val Gln Pro Gly Gly
  1               5                  10                  15

Ser Leu Arg Leu Ser Cys Ala Thr Ser Gly Phe Thr Phe Ile Asp Asn
             20                  25                  30

Tyr Met Ser Trp Val Arg Gln Pro Pro Gly Lys Ala Leu Glu Trp Leu
         35                  40                  45

Gly Phe Ile Arg Asn Lys Val Asn Gly Tyr Thr Thr Glu Tyr Gly Pro
     50                  55                  60

Ser Val Lys Gly Arg Phe Thr Ile Ser Arg Asp Asp Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Val Arg Asp Val Trp Gly Ala Gly Thr Thr Val Thr Val Ser
            100                 105                 110

Ser

<210> SEQ ID NO 198
<211> LENGTH: 111
<212> TYPE: PRT
<213> ORGANISM: Homo sapiens

<400> SEQUENCE: 198

Glu Val Gln Leu Val Gln Ser Gly Gly Gly Val Val Gln Pro Gly Lys
  1               5                  10                  15

Ser Leu Arg Leu Ser Cys Ala Ala Ser Gly Phe Ala Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Trp Gly Gln Gly Thr Leu Val Thr Val Ser Ser
            100                 105                 110

<210> SEQ ID NO 199
<211> LENGTH: 111
<212> TYPE: PRT
<213> ORGANISM: Mus musculus

<400> SEQUENCE: 199

Gln Val Gln Leu Gln Gln Pro Gly Ala Glu Leu Val Lys Pro Gly Ala
  1               5                  10                  15
```

```
Ser Val Lys Leu Ser Cys Lys Ala Ser Gly Tyr Thr Phe Thr Ser Asp
             20                  25                  30

Trp Ile His Trp Val Lys Gln Arg Pro Gly His Gly Leu Glu Trp Ile
         35                  40                  45

Gly Glu Ile Ile Pro Ser Tyr Gly Arg Ala Asn Tyr Asn Glu Lys Ile
 50                  55                  60

Gln Lys Lys Ala Thr Leu Thr Ala Asp Lys Ser Ser Ser Thr Ala Phe
 65                  70                  75                  80

Met Gln Leu Ser Ser Leu Thr Ser Glu Asp Ser Ala Val Tyr Tyr Cys
                 85                  90                  95

Ala Arg Ala Val Trp Gly Ala Gly Thr Thr Val Thr Val Ser Ser
            100                 105                 110

<210> SEQ ID NO 200
<211> LENGTH: 113
<212> TYPE: PRT
<213> ORGANISM: Mus musculus

<400> SEQUENCE: 200

Glu Val Gln Val Val Glu Ser Gly Gly Gly Leu Val Gln Pro Lys Gly
 1               5                  10                  15

Ser Leu Lys Leu Ser Cys Val Val Ser Gly Ser Thr Leu Asn Asn Tyr
             20                  25                  30

Ala Met Asn Trp Val Arg Gln Ala Pro Gly Lys Gly Leu Glu Trp Val
         35                  40                  45

Ala Arg Ile Arg Ser Lys Ser Asn Asn Tyr Ala Thr Tyr Tyr Ala Asp
     50                  55                  60

Ser Val Lys Asp Arg Phe Thr Ile Ser Arg Asp Asp Ser Gln Ser Met
 65                  70                  75                  80

Ile Tyr Leu Gln Met Asn Asn Leu Lys Thr Glu Asp Thr Ala Met Tyr
                 85                  90                  95

Tyr Cys Val Thr Ala Tyr Trp Gly Gln Gly Thr Leu Val Thr Val Ser
            100                 105                 110

Ala

<210> SEQ ID NO 201
<211> LENGTH: 112
<212> TYPE: PRT
<213> ORGANISM: Mus musculus

<400> SEQUENCE: 201

Gln Ile Thr Leu Lys Glu Ser Gly Pro Gly Ile Val Gln Pro Ser Gln
 1               5                  10                  15

Pro Phe Arg Leu Thr Cys Thr Phe Ser Gly Phe Ser Leu Ser Thr Ser
             20                  25                  30

Gly Ile Gly Val Thr Trp Ile Arg Gln Pro Ser Gly Lys Gly Leu Glu
         35                  40                  45

Trp Leu Ala Thr Ile Trp Trp Asp Asp Asp Asn Arg Tyr Asn Pro Ser
     50                  55                  60

Leu Lys Ser Arg Leu Thr Val Ser Lys Asp Thr Ser Asn Asn Gln Ala
 65                  70                  75                  80

Phe Leu Asn Met Met Thr Val Glu Thr Ala Thr Ala Ile Tyr Tyr
                 85                  90                  95

Cys Ala Gln Asp His Trp Gly Gln Gly Thr Ser Val Thr Val Ser Ser
            100                 105                 110

<210> SEQ ID NO 202
```

```
<211> LENGTH: 111
<212> TYPE: PRT
<213> ORGANISM: Mus musculus

<400> SEQUENCE: 202

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Met Arg Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Leu Tyr Tyr Cys
                85                  90                  95

Ala Arg Asp Tyr Trp Gly Gln Gly Thr Ser Val Thr Val Ser Ser
            100                 105                 110

<210> SEQ ID NO 203
<211> LENGTH: 111
<212> TYPE: PRT
<213> ORGANISM: Mus musculus

<400> SEQUENCE: 203

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Asp
                20                  25                  30

Trp Ile His Trp Val Lys Gln Arg Pro Gly His Gly Leu Glu Trp Ile
            35                  40                  45

Gly Glu Ile Ile Pro Ser Tyr Gly Arg Ala Asn Tyr Asn Glu Lys Ile
        50                  55                  60

Gln Lys Lys Ala Thr Leu Thr Ala Asp Lys Ser Ser Ser Thr Ala Phe
65                  70                  75                  80

Met Gln Leu Ser Ser Leu Thr Ser Glu Asp Ser Ala Val Tyr Tyr Cys
                85                  90                  95

Ala Arg Ala Val Trp Gly Ala Gly Thr Thr Val Thr Val Ser Ser
            100                 105                 110

<210> SEQ ID NO 204
<211> LENGTH: 110
<212> TYPE: PRT
<213> ORGANISM: Mus musculus

<400> SEQUENCE: 204

Glu Val Lys Leu Gln Glu Ser Gly Ala Gly Leu Val Gln Pro Ser Gln
1               5                   10                  15

Ser Leu Ser Leu Thr Cys Ser Val Thr Gly Tyr Ser Ile Ser Gly Tyr
                20                  25                  30

Tyr Trp Asn Trp Ile Arg Leu Phe Pro Gly Asn Lys Leu Glu Trp Val
            35                  40                  45

Gly Tyr Ile Ser Asn Val Gly Asp Asn Tyr Asn Pro Ser Leu Lys
        50                  55                  60

Asp Arg Leu Ser Ile Thr Arg Asp Thr Ser Lys Asn Gln Phe Phe Leu
65                  70                  75                  80

Lys Leu Asn Ser Val Thr Thr Glu Asp Thr Ala Thr Tyr Tyr Cys Ala
```

```
                        85                  90                  95

Arg Asp Tyr Trp Gly Gln Gly Thr Thr Val Thr Val Ser Ser
                100                 105                 110

<210> SEQ ID NO 205
<211> LENGTH: 111
<212> TYPE: PRT
<213> ORGANISM: Mus musculus

<400> SEQUENCE: 205

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Asp
            20                  25                  30

Trp Ile His Trp Val Lys Gln Arg Pro Gly His Gly Leu Glu Trp Ile
        35                  40                  45

Gly Glu Ile Ile Pro Ser Tyr Gly Arg Ala Asn Tyr Asn Glu Lys Ile
    50                  55                  60

Gln Lys Lys Ala Thr Leu Thr Ala Asp Lys Ser Ser Ser Thr Ala Phe
65                  70                  75                  80

Met Gln Leu Ser Ser Leu Thr Ser Glu Asp Ser Ala Val Tyr Tyr Cys
                85                  90                  95

Ala Arg Ala Val Trp Gly Ala Gly Thr Thr Val Thr Val Ser Ser
                100                 105                 110

<210> SEQ ID NO 206
<211> LENGTH: 110
<212> TYPE: PRT
<213> ORGANISM: Mus musculus

<400> SEQUENCE: 206

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Asn Ser Tyr Thr Tyr Tyr Val Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Ile Tyr Tyr Cys
                85                  90                  95

Ala Arg Gly Tyr Trp Gly Gln Gly Thr Leu Val Thr Val Ser
                100                 105                 110

<210> SEQ ID NO 207
<211> LENGTH: 111
<212> TYPE: PRT
<213> ORGANISM: Mus musculus

<400> SEQUENCE: 207

Gln Val Gln Leu Ala Gln Ser Gly Pro Glu Leu Val Arg Pro Gly Val
1               5                   10                  15

Ser Val Lys Ile Ser Cys Lys Gly Ser Gly Tyr Thr Phe Thr Thr Tyr
            20                  25                  30

Ala Met His Trp Val Lys Gln Ser His Ala Lys Ser Leu Glu Trp Ile
        35                  40                  45
```

```
Gly Leu Ile Ser Thr Tyr Ser Gly Tyr Thr Asn Tyr Asn Gln Lys Phe
            50                  55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                    85                  90                  95

Ala Arg Asp Val Trp Gly Ala Gly Thr Thr Val Ile Val Ser Ser
                100                 105                 110

<210> SEQ ID NO 208
<211> LENGTH: 110
<212> TYPE: PRT
<213> ORGANISM: Homo sapiens

<400> SEQUENCE: 208

Glu Val Gln Leu Val Glu Ser Gly Ala Glu Val Lys Lys Pro Gly Ser
  1               5                  10                  15

Ser Val Lys Val Ser Cys Lys Ala Ser Gly Asp Thr Phe Ile Arg Tyr
                 20                  25                  30

Ser Phe Thr Trp Val Arg Gln Ala Pro Gly Gln Gly Leu Glu Trp Met
             35                  40                  45

Gly Arg Ile Ile Thr Ile Leu Asp Val Ala His Tyr Ala Pro His Leu
 50                  55                  60

Gln Gly Arg Val Thr Ile Thr Ala Asp Lys Ser Thr Ser Thr Val Tyr
 65                  70                  75                  80

Leu Glu Leu Arg Asn Leu Arg Ser Asp Asp Thr Ala Val Tyr Phe Cys
                    85                  90                  95

Ala Gly Lys His Trp Gly Gln Gly Thr Leu Val Thr Val Ser
                100                 105                 110

<210> SEQ ID NO 209
<211> LENGTH: 111
<212> TYPE: PRT
<213> ORGANISM: Mus musculus

<400> SEQUENCE: 209

Glu Val Gln Leu Gln Gln Ser Gly Pro Glu Leu Val Gln Pro Gly Ala
  1               5                  10                  15

Ser Val Lys Ile Ser Cys Lys Thr Ser Gly Tyr Thr Phe Ser Glu Phe
                 20                  25                  30

Thr Met His Trp Val Lys Gln Ser His Gly Lys Ser Leu Glu Trp Ile
             35                  40                  45

Gly Gly Ile Asn Thr Ile Asn Gly Gly Ser Tyr Lys Gln Ser Phe
 50                  55                  60

Lys Asp Lys Ala Thr Leu Thr Val Asp Lys Ser Ser Ser Thr Ala Tyr
 65                  70                  75                  80

Met Glu Leu Asn Ser Leu Thr Ser Glu Asp Ser Ala Val Tyr Tyr Cys
                    85                  90                  95

Ala Thr Ala Tyr Trp Gly Gln Gly Thr Leu Val Thr Val Ser Ala
                100                 105                 110

<210> SEQ ID NO 210
<211> LENGTH: 110
<212> TYPE: PRT
<213> ORGANISM: Homo sapiens

<400> SEQUENCE: 210

Glu Val Gln Leu Leu Glu Ser Gly Gly Gly Leu Val Gln Pro Gly Gly
  1               5                  10                  15
```

```
Ser Leu Arg Leu Ser Cys Ala Ala Ser Gly Phe Thr Phe Ser Thr Phe
            20                  25                  30

Ser Met Asn Trp Val Arg Gln Ala Pro Gly Lys Gly Leu Glu Trp Val
        35                  40                  45

Ser Tyr Ile Ser Arg Thr Ser Lys Thr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Gln Gly Thr Leu Val Thr Val Ser
            100                 105                 110
```

<210> SEQ ID NO 211
<211> LENGTH: 110
<212> TYPE: PRT
<213> ORGANISM: Mus musculus

<400> SEQUENCE: 211

```
Val Gln Leu Gln Gln Ser Gly Ala Glu Leu Val Arg Pro Gly Ala Ser
1               5                   10                  15

Val Lys Leu Ser Cys Thr Thr Ser Gly Phe Asn Ile Lys Asp Ile Tyr
            20                  25                  30

Ile His Trp Val Lys Gln Arg Pro Glu Gln Gly Leu Glu Trp Ile Gly
        35                  40                  45

Arg Leu Asp Pro Ala Asn Gly Tyr Thr Lys Tyr Asp Pro Lys Phe Gln
50                  55                  60

Gly Lys Ala Thr Ile Thr Val Asp Thr Ser Ser Asn Thr Ala Tyr Leu
65                  70                  75                  80

His Leu Ser Ser Leu Thr Ser Glu Asp Thr Ala Val Tyr Tyr Cys Asp
                85                  90                  95

Gly Asp Tyr Trp Gly Pro Gly Thr Ser Val Thr Val Ser Ser
            100                 105                 110
```

<210> SEQ ID NO 212
<211> LENGTH: 112
<212> TYPE: PRT
<213> ORGANISM: Mus musculus

<400> SEQUENCE: 212

```
Gln Val Lys Leu Gln Glu Ser Gly Pro Ala Val Ile Lys Pro Ser Gln
1               5                   10                  15

Ser Leu Ser Leu Thr Cys Ile Val Ser Gly Phe Ser Ile Thr Arg Thr
            20                  25                  30

Asn Tyr Cys Trp His Trp Ile Arg Gln Ala Pro Gly Lys Gly Leu Glu
        35                  40                  45

Trp Met Gly Arg Ile Cys Tyr Glu Gly Ser Ile Tyr Tyr Ser Pro Ser
50                  55                  60

Ile Lys Ser Arg Ser Thr Ile Ser Arg Asp Thr Ser Leu Asn Lys Phe
65                  70                  75                  80

Phe Ile Gln Leu Ile Ser Val Thr Asn Glu Asp Thr Ala Met Tyr Tyr
                85                  90                  95

Cys Ser Arg Asp Val Trp Gly Gln Gly Thr Thr Val Thr Val Ser Ser
            100                 105                 110
```

<210> SEQ ID NO 213
<211> LENGTH: 111

```
<212> TYPE: PRT
<213> ORGANISM: Mus musculus

<400> SEQUENCE: 213

Gln Val Gln Leu Gln Gln Pro Gly Ala Glu Leu Val Lys Pro Gly Pro
1               5                   10                  15

Ser Val Lys Leu Ser Cys Lys Ala Ser Gly Phe Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Leu Pro Ser Asn Gly Arg Thr Asn Tyr Asn Glu Lys Phe
    50                  55                  60

Lys Thr Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Trp Gly Gln Gly Thr Thr Leu Thr Val Ser Ser
            100                 105                 110

<210> SEQ ID NO 214
<211> LENGTH: 110
<212> TYPE: PRT
<213> ORGANISM: Mus musculus

<400> SEQUENCE: 214

Asp Val Gln Leu Gln Gln Ser Gly Pro Asp Leu Val Lys Pro Ser Gln
1               5                   10                  15

Ser Leu Ser Leu Thr Cys Thr Val Thr Gly Tyr Ser Ile Ser Gly Tyr
            20                  25                  30

Ser Trp His Trp Ile Arg Gln Phe Pro Gly Asn Lys Leu Glu Trp Met
        35                  40                  45

Gly Tyr Ile His Tyr Ser Ala Gly Thr Asn Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Asp Cys Trp Gly Gln Gly Thr Thr Val Thr Val Ser Ser
            100                 105                 110

<210> SEQ ID NO 215
<211> LENGTH: 109
<212> TYPE: PRT
<213> ORGANISM: Mus musculus

<400> SEQUENCE: 215

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Ser Asp Tyr Ala
            20                  25                  30

Trp Asn Trp Ile Arg Gln Phe Pro Gly Asn Lys Leu Glu Trp Met Gly
        35                  40                  45

Tyr Ile Thr Tyr Ser Gly Ser Thr Gly Tyr Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Ala Ser
                85                  90                  95
```

Thr Tyr Trp Gly Gln Gly Thr Leu Val Thr Val Ser Ala
                100                 105

<210> SEQ ID NO 216
<211> LENGTH: 111
<212> TYPE: PRT
<213> ORGANISM: Mus musculus

<400> SEQUENCE: 216

Glu Val Leu Val Glu Ser Gly Gly Asp Leu Val Lys Pro Gly Gly
  1               5                  10                  15

Phe Leu Lys Leu Ser Cys Ala Ala Ser Gly Phe Thr Phe Ser Ser Phe
                 20                  25                  30

Gly Met Ser Trp Val Arg His Thr Pro Asp Lys Arg Leu Glu Trp Val
             35                  40                  45

Ala Thr Ile Ser Asn Gly Gly Tyr Thr Tyr Tyr Gln Asp Ser Val
         50                  55                  60

Lys Gly Arg Phe Thr Ile Ser Arg Asp Asn Ala Lys Asn Thr Leu Phe
 65                  70                  75                  80

Leu Glu Met Thr Ser Leu Lys Ser Glu Asp Ala Gly Leu Tyr Tyr Cys
                 85                  90                  95

Ala Arg Ala Tyr Trp Gly Arg Gly Thr Leu Val Thr Val Ser Ala
            100                 105                 110

<210> SEQ ID NO 217
<211> LENGTH: 112
<212> TYPE: PRT
<213> ORGANISM: Mus musculus

<400> SEQUENCE: 217

Gln Val Gln Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Tyr
                 20                  25                  30

Gly Met Gly Val Ser Trp Ile Arg Gln Pro Ser Gly Lys Gly Leu Glu
             35                  40                  45

Trp Leu Ala His Ile Phe Trp Asp Gly Asp Lys Arg Tyr Asn Pro Ser
         50                  55                  60

Leu Lys Ser Arg Leu Lys Ile Ser Lys Asp Thr Ser Asn Asn Gln Val
 65                  70                  75                  80

Phe Leu Lys Ile Thr Ser Val Asp Thr Ala Asp Thr Ala Thr Tyr Tyr
                 85                  90                  95

Cys Val Gln Ile Tyr Trp Gly Gln Gly Thr Ser Val Thr Val Ser Ser
            100                 105                 110

<210> SEQ ID NO 218
<211> LENGTH: 98
<212> TYPE: PRT
<213> ORGANISM: Mus musculus

<400> SEQUENCE: 218

Gln Val Lys Leu Gln Gln Ser Gly Gly Gly Leu Val Lys Pro Gly Ala
  1               5                  10                  15

Ser Leu Lys Leu Ser Cys Val Thr Ser Gly Phe Thr Phe Arg Lys Phe
                 20                  25                  30

Gly Met Ser Trp Val Arg Gln Thr Ser Asp Lys Cys Leu Glu Trp Val
             35                  40                  45

Ala Ser Ile Ser Thr Gly Gly Tyr Asn Thr Tyr Tyr Ser Asp Asn Val

```
                 50                  55                  60
Lys Gly Arg Phe Thr Ile Ser Arg Glu Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Thr Arg

<210> SEQ ID NO 219
<211> LENGTH: 111
<212> TYPE: PRT
<213> ORGANISM: Mus musculus

<400> SEQUENCE: 219

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Ser Phe Ser Ser Tyr
                 20                  25                  30

Gly Met Ser Trp Val Arg Gln Thr Pro Asp Lys Arg Leu Glu Trp Val
                 35                  40                  45

Ala Thr Ile Ser Asn Gly Gly Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Ser Ala Met Tyr Tyr Cys
                 85                  90                  95

Ala Arg Ala Tyr Trp Gly Gln Gly Thr Leu Val Thr Val Ser Ala
                100                 105                 110

<210> SEQ ID NO 220
<211> LENGTH: 109
<212> TYPE: PRT
<213> ORGANISM: Mus musculus

<400> SEQUENCE: 220

Val Lys Leu Gln Gln Ser Gly Pro Gly Leu Val Lys Pro Ser Gln Ser
  1               5                  10                  15

Leu Ser Leu Thr Cys Thr Val Thr Gly Tyr Ser Ile Ser Asp Tyr Ala
                 20                  25                  30

Trp Asn Trp Ile Arg Gln Phe Pro Gly Asn Lys Leu Glu Trp Met Ala
                 35                  40                  45

Tyr Ile Ser Tyr Ser Gly Ser Thr Thr Tyr Asn Pro Ser Leu Lys Ser
 50                  55                  60

Arg Ile Ser Ile Thr Arg Asp Thr Ser Lys Asn Gln Phe Phe Leu Gln
 65                  70                  75                  80

Leu Asn Ser Val Thr Thr Glu Asp Thr Ala Ile Tyr Tyr Cys Ala Arg
                 85                  90                  95

Asp Tyr Trp Gly Ala Gly Thr Thr Leu Thr Val Ser Ala
                100                 105

<210> SEQ ID NO 221
<211> LENGTH: 109
<212> TYPE: PRT
<213> ORGANISM: Mus musculus

<400> SEQUENCE: 221

Val Thr Leu Ser Gln Ser Gly Pro Gly Leu Val Lys Pro Ser Gln Ser
  1               5                  10                  15

Leu Ser Leu Thr Cys Thr Val Thr Ser Tyr Ser Ile Ser Asp Tyr Ala
```

-continued

```
                    20                  25                  30
Trp Asn Trp Ile Arg Gln Phe Ala Gly Gln Ser Leu Glu Trp Met Gly
            35                  40                  45

Tyr Ile Ser Tyr Ser Gly Ser Thr Ser Tyr Asn Pro Ser Leu Lys Ser
        50                  55                  60

Arg Ile Ser Ile Thr Arg Asp Thr Ser Lys Asn Gln Phe Phe Leu Gln
 65                 70                  75                  80

Leu Asn Ser Val Thr Thr Asp Asp Thr Ala Thr Tyr Tyr Cys Ala Arg
                85                  90                  95

Pro Tyr Trp Gly Thr Gly Thr Asn Val Thr Val Ser Ala
            100                 105

<210> SEQ ID NO 222
<211> LENGTH: 111
<212> TYPE: PRT
<213> ORGANISM: Mus musculus

<400> SEQUENCE: 222

Gln Val Gln Leu Gln Gln Ser Gly Pro Glu Asp Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Met Asn Trp Val Lys Gln Ser Pro Gly Lys Gly Leu Glu Trp Ile
            35                  40                  45

Gly Asp Ile Asn Pro Asn Asn Gly Gly Thr Ser Tyr Asn Gln Lys Phe
        50                  55                  60

Lys Gly Arg Ala Thr Leu Thr Val Asp Lys Ser Ser Ser Thr Ala Tyr
 65                 70                  75                  80

Met Glu Leu Arg Ser Leu Thr Ser Glu Asp Ser Ser Val Tyr Tyr Cys
                85                  90                  95

Glu Ser Ala Tyr Trp Gly Gln Gly Thr Thr Val Thr Val Ser Ala
            100                 105                 110

<210> SEQ ID NO 223
<211> LENGTH: 111
<212> TYPE: PRT
<213> ORGANISM: Mus musculus

<400> SEQUENCE: 223

Glu Val Asn Leu Gln Gln Ser Gly Thr Val Leu Ala Arg Pro Gly Ala
 1               5                  10                  15

Ser Val Arg Met Ser Cys Lys Ala Ser Gly Tyr Ser Phe Thr Ser Tyr
                20                  25                  30

Trp Leu His Trp Ile Lys Gln Arg Pro Gly Gln Gly Leu Glu Trp Ile
            35                  40                  45

Gly Gly Ile Tyr Pro Gly Asn Arg Asp Thr Arg Tyr Thr Gln Arg Phe
        50                  55                  60

Lys Asp Lys Ala Lys Leu Thr Ala Val Thr Ser Ala Asn Thr Ala Tyr
 65                 70                  75                  80

Met Glu Leu Ser Ser Leu Thr Asn Glu Asp Ser Ala Val Tyr Tyr Cys
                85                  90                  95

Ser Ile Asp Tyr Trp Gly Gln Gly Thr Thr Val Thr Val Ser Ser
            100                 105                 110

<210> SEQ ID NO 224
<211> LENGTH: 111
<212> TYPE: PRT
<213> ORGANISM: Mus musculus
```

<400> SEQUENCE: 224

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Phe Met His Trp Val Lys Gln Arg Pro Glu Gln Gly Leu Glu Trp Ile
        35                  40                  45

Gly Arg Ile Asp Pro Ala Asn Asp Asn Thr Lys Tyr Ala Pro Lys Phe
50                  55                  60

Gln Asp Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Asp Val Trp Gly Ala Gly Thr Thr Val Thr Val Pro Ser
            100                 105                 110

<210> SEQ ID NO 225
<211> LENGTH: 111
<212> TYPE: PRT
<213> ORGANISM: Homo sapiens

<400> SEQUENCE: 225

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Asp Val Trp Gly Lys Gly Thr Thr Val Ile Val Ser Ser
            100                 105                 110

<210> SEQ ID NO 226
<211> LENGTH: 110
<212> TYPE: PRT
<213> ORGANISM: Mus musculus

<400> SEQUENCE: 226

Glu Val Gln Leu Gln Glu Ser Gly Pro Ser Leu Val Lys Pro Ser Gln
1               5                   10                  15

Thr Leu Ser Leu Thr Cys Ser Val Thr Gly Val Ser Ile Thr Ser Gly
            20                  25                  30

Tyr Trp Asn Trp Ile Arg Lys Phe Pro Gly Asn Lys Phe Glu Tyr Met
        35                  40                  45

Gly Tyr Ile Ser Lys Ser Gly Ser Ala Tyr Tyr Asn Pro Ser Leu Lys
50                  55                  60

Ser Arg Ile Ser Phe Thr Arg Asp Thr Ser Lys Asn Gln Phe Tyr Leu
65                  70                  75                  80

Lys Leu Asn Ser Val Thr Thr Glu Asp Thr Ala Thr Tyr Tyr Cys Ala
                85                  90                  95

Ile Asp Ile Trp Gly Ala Gly Thr Thr Val Thr Val Ser Ser

<210> SEQ ID NO 227
<211> LENGTH: 113
<212> TYPE: PRT
<213> ORGANISM: Mus musculus

<400> SEQUENCE: 227

```
Glu Val Lys Val Glu Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
             20                  25                  30

Trp Met Glu Trp Val Arg Gln Ser Pro Glu Lys Gly Leu Glu Trp Val
         35                  40                  45

Ala Glu Ile Arg Leu Lys Ser Asn Asn Tyr Ala Thr His Tyr Ala Glu
     50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Asp Tyr Trp Gly Gln Gly Thr Ser Val Thr Val Ser
            100                 105                 110

Ser
```

<210> SEQ ID NO 228
<211> LENGTH: 111
<212> TYPE: PRT
<213> ORGANISM: Mus musculus

<400> SEQUENCE: 228

```
Glu Val Gln Leu Gln Gln Ser Gly Pro Glu Leu Lys Lys Pro Gly Glu
  1               5                  10                  15

Thr Val Lys Ile Ser Cys Lys Ala Thr Asn Tyr Ala Phe Thr Asp Tyr
             20                  25                  30

Ser Met His Trp Val Lys Gln Ala Pro Gly Gly Asp Leu Lys Tyr Val
         35                  40                  45

Gly Trp Ile Asn Thr Glu Thr Asp Glu Pro Thr Phe Ala Asp Asp Phe
     50                  55                  60

Lys Gly Arg Phe Ala Phe Ser Leu Asp Thr Ser Thr Ser Thr Ala Phe
 65                  70                  75                  80

Leu Gln Ile Asn Asn Leu Lys Asn Glu Asp Thr Ala Thr Tyr Phe Cys
                 85                  90                  95

Val Arg Thr Tyr Trp Gly Gln Gly Thr Thr Val Thr Val Ser Ser
            100                 105                 110
```

<210> SEQ ID NO 229
<211> LENGTH: 111
<212> TYPE: PRT
<213> ORGANISM: Mus musculus

<400> SEQUENCE: 229

```
Gln Ile Gln Leu Val Gln Ser Gly Pro Glu Leu Lys Thr Pro Gly Glu
  1               5                  10                  15

Thr Val Arg Ile Ser Cys Lys Ala Ser Gly Tyr Thr Phe Thr Thr Tyr
             20                  25                  30

Gly Met Ser Trp Val Lys Gln Thr Pro Gly Lys Gly Phe Lys Trp Met
         35                  40                  45

Gly Trp Ile Asn Thr Tyr Ser Gly Val Pro Thr Tyr Ala Asp Asp Phe
```

```
                50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                    85                  90                  95

Ala Arg Asp Val Trp Gly Thr Gly Thr Thr Val Thr Val Ser Ser
                100                 105                 110

<210> SEQ ID NO 230
<211> LENGTH: 111
<212> TYPE: PRT
<213> ORGANISM: Mus musculus

<400> SEQUENCE: 230

Gln Val Gln Leu Gln Gln Ser Gly Pro Glu Leu Val Arg Pro Gly Ala
 1               5                  10                  15

Ser Val Lys Ile Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Gly Trp Ile Phe Pro Arg Asn Gly Asn Thr Lys Tyr Asn Glu Lys Phe
        50                  55                  60

Lys Gly Lys Ala Thr Leu Thr Val Asp Lys Ser Ser Ser Thr Ala Phe
 65                  70                  75                  80

Met Gln Leu Ser Ser Leu Thr Ser Glu Asp Ser Ala Val Tyr Phe Cys
                85                  90                  95

Ala Thr Asp Tyr Trp Gly Gln Gly Thr Thr Val Thr Val Ser Ser
                100                 105                 110

<210> SEQ ID NO 231
<211> LENGTH: 111
<212> TYPE: PRT
<213> ORGANISM: Mus musculus

<400> SEQUENCE: 231

Glu Val Gln Leu Gln Gln Ser Gly Ala Glu Leu Val Arg Ala Gly Ser
 1               5                  10                  15

Ser Val Lys Met Ser Cys Lys Ala Ser Gly Tyr Thr Phe Thr Ser Tyr
                20                  25                  30

Gly Ile Asn Trp Val Lys Gln Arg Pro Gly Gln Gly Leu Glu Trp Ile
            35                  40                  45

Gly Tyr Ile Asn Pro Gly Asn Gly Tyr Thr Lys Tyr Asn Glu Lys Phe
        50                  55                  60

Lys Gly Lys Thr Thr Leu Thr Val Asp Lys Ser Ser Ser Thr Ala Tyr
 65                  70                  75                  80

Met Gln Leu Arg Ser Leu Thr Ser Glu Asp Ser Ala Val Tyr Phe Cys
                85                  90                  95

Ala Arg Asp Tyr Trp Gly Gln Gly Thr Thr Leu Thr Val Ser Ser
                100                 105                 110

<210> SEQ ID NO 232
<211> LENGTH: 113
<212> TYPE: PRT
<213> ORGANISM: Mus musculus

<400> SEQUENCE: 232

Gln Val Gln Leu Gln Glu Ser Gly Gly Gly Leu Val Gln Pro Arg Gly
 1               5                  10                  15
```

```
Ser Leu Lys Leu Ser Cys Ala Ala Ser Gly Phe Thr Phe Asn Thr Asp
            20                  25                  30

Ala Met Asn Trp Val Arg Gln Ala Pro Gly Lys Gly Leu Glu Trp Val
            35                  40                  45

Ala Arg Ile Arg Ser Lys Gly Phe Asn Phe Ala Thr Tyr Tyr Ala Asp
50                  55                  60

Ser Val Arg Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Gly Ile Tyr
                85                  90                  95

Tyr Cys Val Arg Asp Tyr Trp Gly Gln Gly Thr Thr Leu Thr Val Ser
            100                 105                 110

Ser
```

<210> SEQ ID NO 233
<211> LENGTH: 111
<212> TYPE: PRT
<213> ORGANISM: Homo sapiens

<400> SEQUENCE: 233

```
Gln Val Gln Leu Val Gln Ser Gly Ala Glu Val Lys Arg Pro Gly Ser
1               5                   10                  15

Ser Val Thr Val Ser Cys Lys Ala Ser Gly Gly Ser Phe Ser Thr Tyr
            20                  25                  30

Ala Leu Ser Trp Val Arg Gln Ala Pro Gly Arg Gly Leu Glu Trp Met
            35                  40                  45

Gly Gly Val Ile Pro Leu Leu Thr Ile Thr Asn Tyr Ala Pro Arg Phe
50                  55                  60

Gln Gly Arg Ile Thr Ile Thr Ala Asp Arg Ser Thr Ser Thr Ala Tyr
65                  70                  75                  80

Leu Glu Leu Asn Ser Leu Arg Pro Glu Asp Thr Ala Val Tyr Tyr Cys
                85                  90                  95

Ala Arg Ala His Trp Gly Gln Gly Thr Leu Val Thr Val Ser Ser
            100                 105                 110
```

<210> SEQ ID NO 234
<211> LENGTH: 110
<212> TYPE: PRT
<213> ORGANISM: Mus musculus

<400> SEQUENCE: 234

```
Val Gln Leu Gln Gln Ser Gly Ala Glu Leu Val Arg Ser Gly Ala Ser
1               5                   10                  15

Val Lys Leu Ser Cys Thr Ala Ser Gly Phe Asn Ile Lys Asp Tyr Tyr
            20                  25                  30

Met Tyr Trp Val Lys Leu Arg Pro Glu Gln Gly Leu Glu Trp Ile Gly
            35                  40                  45

Trp Ile Asp Pro Glu Asn Gly Asp Thr Glu Tyr Val Pro Thr Phe Gln
50                  55                  60

Gly Lys Val Thr Met Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Asn
                85                  90                  95

Ala Asp Tyr Trp Gly Gln Gly Thr Thr Val Thr Thr Ser Ser
            100                 105                 110
```

<210> SEQ ID NO 235

```
<211> LENGTH: 111
<212> TYPE: PRT
<213> ORGANISM: Homo sapiens

<400> SEQUENCE: 235

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Trp Val Leu Pro Ser Val Gly Phe Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Gln Gly Thr Leu Val Thr Val Ser Ser
            100                 105                 110

<210> SEQ ID NO 236
<211> LENGTH: 111
<212> TYPE: PRT
<213> ORGANISM: Mus musculus

<400> SEQUENCE: 236

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Arg Cys
            20                  25                  30

Ala Met Ser Trp Val Arg Gln Thr Pro Glu Lys Arg Leu Glu Trp Val
        35                  40                  45

Ala Gly Ile Ser Ser Gly Gly Ser Tyr Thr Phe Tyr Pro Asp Thr Val
    50                  55                  60

Lys Gly Arg Phe Ile Ile Ser Arg Asn Asn Ala Arg Asn Thr Leu Ser
65                  70                  75                  80

Leu Gln Met Ser Ser Leu Arg Ser Glu Asp Thr Ala Ile Tyr Tyr Cys
                85                  90                  95

Thr Arg Asp Tyr Trp Gly Gln Gly Thr Thr Leu Thr Val Ser Ser
            100                 105                 110

<210> SEQ ID NO 237
<211> LENGTH: 112
<212> TYPE: PRT
<213> ORGANISM: Mus musculus

<400> SEQUENCE: 237

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Arg Ser Tyr Asn Pro Ser
    50                  55                  60

Leu Lys Ser Gln Leu Thr Ile Ser Lys Asp Ala Ala Arg Asn Gln Val
65                  70                  75                  80

Phe Leu Arg Ile Thr Ser Val Asp Thr Ala Asp Thr Ala Thr Tyr Tyr
```

```
                85                  90                  95

Cys Val Arg Ala Tyr Trp Gly Gln Gly Thr Leu Val Thr Val Ser Ala
                100                 105                 110

<210> SEQ ID NO 238
<211> LENGTH: 112
<212> TYPE: PRT
<213> ORGANISM: Mus musculus

<400> SEQUENCE: 238

Gln Val Thr Leu Lys Glu Ser Gly Pro Gly Ile Leu Lys Pro Ser Gln
1               5                   10                  15

Thr Leu Ser Leu Thr Cys Ser Leu Ser Gly Phe Ser Leu Arg Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Asp Lys Asn Tyr Asn Pro Ser
        50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Val Arg Ala Tyr Trp Gly Gln Gly Thr Leu Val Thr Val Ser Ala
                100                 105                 110

<210> SEQ ID NO 239
<211> LENGTH: 112
<212> TYPE: PRT
<213> ORGANISM: Mus musculus

<400> SEQUENCE: 239

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Asp Arg Ser Tyr Asn Pro Ser
        50                  55                  60

Leu Lys Ser Gln Leu Thr Ile Ser Lys Asp Thr Ser Arg Asn Gln Val
65                  70                  75                  80

Phe Leu Arg Ile Thr Ser Val Asp Thr Ala Asp Thr Ala Thr Tyr Tyr
                85                  90                  95

Cys Val Arg Ala Tyr Trp Gly Gln Gly Thr Leu Val Thr Val Ser Ala
                100                 105                 110

<210> SEQ ID NO 240
<211> LENGTH: 110
<212> TYPE: PRT
<213> ORGANISM: Mus musculus

<400> SEQUENCE: 240

Val Gln Leu Gln Glu Ser Asp Ala Glu Leu Val Lys Pro Gly Ala Ser
1               5                   10                  15

Val Lys Ile Ser Cys Lys Ala Ser Gly Tyr Thr Phe Thr Asp His Val
                20                  25                  30

Ile His Trp Val Lys Gln Lys Pro Glu Gln Gly Leu Glu Trp Ile Gly
            35                  40                  45
```

-continued

```
Tyr Ile Ser Pro Gly Asn Gly Asp Ile Lys Tyr Asn Glu Lys Phe Lys
        50                  55                  60
Gly Lys Ala Thr Leu Thr Ala Asp Lys Ser Ser Ser Thr Ala Tyr Met
65                  70                  75                  80
Gln Leu Asn Ser Leu Thr Ser Glu Asp Ser Ala Val Tyr Leu Cys Lys
                85                  90                  95
Arg Asp Tyr Trp Gly Gln Gly Thr Thr Leu Thr Val Ser Ser
            100                 105                 110
```

<210> SEQ ID NO 241
<211> LENGTH: 111
<212> TYPE: PRT
<213> ORGANISM: Mus musculus

<400> SEQUENCE: 241

```
Glu Val Gln Leu Glu Glu Ser Gly Pro Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Phe Glu Trp Ile
            35                  40                  45
Gly Asp Ile Tyr Pro Gly Gly Val Tyr Thr Thr Asn Asn Glu Lys Phe
        50                  55                  60
Arg Gly Lys Ala Ile Leu Thr Ala Asp Thr Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Asp Tyr Trp Gly Gln Gly Thr Ser Val Thr Val Ser Ser
            100                 105                 110
```

<210> SEQ ID NO 242
<211> LENGTH: 111
<212> TYPE: PRT
<213> ORGANISM: Mus musculus

<400> SEQUENCE: 242

```
Gln Val Gln Leu Leu Glu Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
                20                  25                  30
Gly Met Asn Trp Val Lys Gln Ala Pro Gly Lys Gly Leu Lys Trp Met
            35                  40                  45
Gly Trp Ile Asn Thr Tyr Thr Gly Glu Pro Thr Tyr Ala Asp Asp Phe
        50                  55                  60
Lys Gly Arg Phe Ala Phe Ser Leu Glu Thr Ser Ala Ser Thr Ala Tyr
65                  70                  75                  80
Leu Gln Ile Asn Asn Leu Lys Asn Glu Asp Thr Ala Thr Tyr Phe Cys
                85                  90                  95
Val Gln Asp Tyr Trp Gly Ala Gly Thr Thr Val Thr Val Ser Ser
            100                 105                 110
```

<210> SEQ ID NO 243
<211> LENGTH: 109
<212> TYPE: PRT
<213> ORGANISM: Mus musculus

<400> SEQUENCE: 243

```
Asp Val Gln Leu Gln Glu Ser Gly Pro Gly Leu Val Lys Pro Ser Gln
1               5                   10                  15
```

Ser Gln Ser Leu Thr Cys Thr Val Thr Gly Tyr Ser Ile Ser Asp Tyr
            20                  25                  30

Ala Trp Asn Trp Ile Arg Gln Phe Pro Gly Asn Lys Leu Glu Trp Met
        35                  40                  45

Gly Tyr Met Ser Tyr Ser Gly Ser Thr Arg Tyr Asn Pro Ser Leu Arg
    50                  55                  60

Ser Arg Ile Ser Ile Thr Arg Asp Thr Ser Lys Asn Gln Phe Phe Leu
65                  70                  75                  80

Gln Leu Lys Ser Val Thr Thr Glu Asp Thr Ala Thr Tyr Phe Cys Ala
                85                  90                  95

Arg Ala Tyr Trp Gly Gln Gly Thr Gln Val Ser Val Ser
                100                 105

<210> SEQ ID NO 244
<211> LENGTH: 109
<212> TYPE: PRT
<213> ORGANISM: Mus musculus

<400> SEQUENCE: 244

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Ser Asp Tyr Ala
            20                  25                  30

Trp Asn Trp Ile Arg Gln Phe Pro Gly Asn Lys Leu Glu Trp Met Gly
        35                  40                  45

Tyr Ile Ser Tyr Ser Gly Ser Thr Ser Tyr Ser Pro Ser Leu Lys Ser
    50                  55                  60

Arg Ile Ser Leu Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Val Thr
                85                  90                  95

Ser Tyr Trp Gly Gln Gly Thr Thr Val Thr Val Ser Ser
                100                 105

<210> SEQ ID NO 245
<211> LENGTH: 111
<212> TYPE: PRT
<213> ORGANISM: Mus musculus

<400> SEQUENCE: 245

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Met Phe Thr Asn Tyr
            20                  25                  30

Gly Met Asn Trp Val Lys Gln Ala Pro Gly Lys Ala Leu Lys Leu Met
        35                  40                  45

Gly Trp Ile Asn Pro Tyr Thr Gly Glu Ser Thr Phe Ala Asp Asp Phe
    50                  55                  60

Lys Gly Arg Phe Ala Phe Phe Leu Glu Thr Ser Ala Thr Thr Ala Tyr
65                  70                  75                  80

Leu Gln Ile Asn Asn Leu Lys Asn Glu Asp Met Ala Thr Tyr Phe Cys
                85                  90                  95

Ala Arg Asp Tyr Trp Gly Gln Gly Thr Ser Leu Thr Val Ser Ser
                100                 105                 110

<210> SEQ ID NO 246
<211> LENGTH: 113

<212> TYPE: PRT
<213> ORGANISM: Mus musculus

<400> SEQUENCE: 246

Glu Val Gln Pro Val Glu Thr Gly Gly Gly Leu Val Gln Pro Lys Gly
1               5                   10                  15

Ser Leu Lys Leu Ser Cys Ala Ala Ser Gly Phe Ser Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Met Tyr
                85                  90                  95

Tyr Cys Val Arg Ala Tyr Trp Gly Gln Gly Thr Leu Val Thr Val Ser
            100                 105                 110

Ala

<210> SEQ ID NO 247
<211> LENGTH: 110
<212> TYPE: PRT
<213> ORGANISM: Mus musculus

<400> SEQUENCE: 247

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Ser Gly Tyr
            20                  25                  30

Ala Trp Asn Trp Ile Arg Gln Phe Pro Gly Asn Lys Leu Glu Trp Met
        35                  40                  45

Gly Tyr Ile Arg Tyr Ser Gly Asp Thr Arg Tyr Asn Pro Ser Leu Lys
50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Ile Asp Tyr Trp Gly Gln Gly Thr Leu Val Thr Val Ser Ala
            100                 105                 110

<210> SEQ ID NO 248
<211> LENGTH: 111
<212> TYPE: PRT
<213> ORGANISM: Mus musculus

<400> SEQUENCE: 248

Gln Val Lys Leu Leu Glu Ser Gly Ala Val Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Asn Trp Leu Lys Gln Lys Pro Gly Gln Ser Leu Glu Trp Ile
        35                  40                  45

Ala Trp Ile Tyr Ala Gly Ser Gly Gly Thr Val Tyr Asn Gln His Phe
50                  55                  60

Thr Asp Lys Ala Arg Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Arg Ala Tyr Trp Gly Gln Gly Thr Leu Val Thr Val Ser Ala
            100                 105                 110

<210> SEQ ID NO 249
<211> LENGTH: 111
<212> TYPE: PRT
<213> ORGANISM: Mus musculus

<400> SEQUENCE: 249

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ala Phe Thr Asn Tyr
            20                  25                  30

Gly Val Asn Trp Val Lys Glu Ala Pro Gly Lys Glu Leu Lys Trp Met
        35                  40                  45

Gly Trp Ile Asn Ile Tyr Thr Gly Glu Pro Thr Tyr Val Asp Asp Phe
    50                  55                  60

Lys Gly Arg Phe Ala Phe Ser Leu Glu Thr Ser Ala Ser Thr Ala Tyr
65                  70                  75                  80

Leu Glu Ile Asn Asn Leu Lys Asn Glu Asp Thr Ala Thr Tyr Phe Cys
                85                  90                  95

Thr Arg Asp Val Trp Gly Ala Gly Thr Thr Val Thr Val Ser Ser
            100                 105                 110

<210> SEQ ID NO 250
<211> LENGTH: 111
<212> TYPE: PRT
<213> ORGANISM: Mus musculus

<400> SEQUENCE: 250

Glu Val Gln Leu Gln Glu Ser Gly Thr Glu Leu Val Lys Pro Gly Ala
1               5                   10                  15

Ser Val Lys Ile Ser Cys Lys Ala Ser Gly Tyr Ile Ser Thr Asp His
            20                  25                  30

Ala Ile His Trp Val Lys Gln Arg Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Val Lys Ala Thr Leu Thr Ala Asp Gln Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Asp Tyr Trp Gly Gln Gly Thr Thr Leu Thr Val Ser Ser
            100                 105                 110

<210> SEQ ID NO 251
<211> LENGTH: 111
<212> TYPE: PRT
<213> ORGANISM: Mus musculus

<400> SEQUENCE: 251

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Phe
            20                  25                  30

Trp Met His Trp Val Lys Gln Arg Pro Gly Gln Gly Leu Glu Trp Ile
        35                  40                  45

Gly Thr Ile Tyr Pro Gly Asn Ser Asp Thr Ser Tyr Asn Gln Lys Phe
            50                  55                  60

Lys Gly Lys Ala Lys Leu Thr Ala Val Thr Ser Ala Ser Thr Ala Tyr
 65                  70                  75                  80

Met Glu Val Ser Ser Leu Thr Asn Glu Asp Ser Ala Val Tyr Tyr Cys
                85                  90                  95

Thr Arg Asp Tyr Trp Gly Gln Gly Thr Ser Val Thr Val Ser Ser
            100                 105                 110

<210> SEQ ID NO 252
<211> LENGTH: 111
<212> TYPE: PRT
<213> ORGANISM: Mus musculus

<400> SEQUENCE: 252

Glu Ile Gln Leu Gln Gln Ser Gly Pro Glu Leu Val Lys Pro Gly Ala
 1               5                   10                  15

Ser Val Lys Val Ser Cys Lys Ala Ser Gly Tyr Ser Phe Ile Asp Tyr
                20                  25                  30

Asn Ile His Trp Val Lys Gln Ser His Gly Lys Ser Leu Glu Trp Ile
            35                  40                  45

Gly Tyr Ile Val Pro Tyr Ser Gly Gly Thr Thr Phe Asn Gln Lys Phe
        50                  55                  60

Lys Gly Lys Ala Thr Leu Thr Val Asp Lys Ser Ser Thr Ala Phe
 65                  70                  75                  80

Met His Leu Asn Ser Leu Thr Phe Glu Asp Ser Ala Val Tyr Tyr Cys
                85                  90                  95

Ala Asn Val Tyr Trp Gly Gln Gly Thr Thr Leu Thr Val Ser Ser
            100                 105                 110

<210> SEQ ID NO 253
<211> LENGTH: 111
<212> TYPE: PRT
<213> ORGANISM: Mus musculus

<400> SEQUENCE: 253

Glu Val Lys Leu Asp Glu Thr Gly Gly Gly Leu Val Gln Pro Gly Arg
 1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Ser Val Tyr
 65                  70                  75                  80

Leu Gln Met Asn Asn Leu Arg Val Glu Asp Met Gly Ile Tyr Tyr Cys
                85                  90                  95

Thr Gly Asp Tyr Trp Gly Gln Gly Thr Ser Val Thr Val Ser Ser
            100                 105                 110

<210> SEQ ID NO 254
<211> LENGTH: 110
<212> TYPE: PRT
<213> ORGANISM: Mus musculus

<400> SEQUENCE: 254

Gln Val Gln Leu Gln Gln Pro Gly Ala Glu Leu Val Arg Pro Gly Ala
 1               5                   10                  15

```
                1               5                  10                 15
Ser Val Lys Leu Ser Cys Lys Ala Ser Gly Tyr Thr Phe Thr Ser Tyr
                    20                  25                 30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                    85                  90                  95

Ala Arg Gly Tyr Trp Gly Gln Gly Thr Leu Val Thr Val Ser
                100                 105                 110

<210> SEQ ID NO 255
<211> LENGTH: 107
<212> TYPE: PRT
<213> ORGANISM: Mus musculus

<400> SEQUENCE: 255

Val His Leu Val Gln Ser Gly Pro Gly Leu Val Ala Pro Ser Gln Ser
1               5                   10                  15

Leu Ser Ile Thr Cys Thr Val Ser Gly Phe Ser Leu Thr Thr Tyr Gly
                20                  25                  30

Val His Trp Phe Arg Gln Pro Pro Gly Lys Gly Leu Glu Trp Leu Gly
            35                  40                  45

Leu Ile Trp Ala Gly Gly Asn Thr Asp Tyr Asn Ser Ala Leu Met Ser
        50                  55                  60

Arg Leu Ser Ile Asn Lys Asp Asn Ser Lys Ser Gln Val Phe Leu Lys
65                  70                  75                  80

Met Asn Ser Leu Gln Ala Asp Asp Thr Ala Met Tyr Tyr Cys Ala Arg
                85                  90                  95

Asp Tyr Trp Gly Gln Gly Thr Ser Val Thr Val
                100                 105

<210> SEQ ID NO 256
<211> LENGTH: 110
<212> TYPE: PRT
<213> ORGANISM: Mus musculus

<400> SEQUENCE: 256

Val Gln Leu Gln Gln Ser Gly Pro Glu Leu Val Lys Pro Gly Ala Ser
1               5                   10                  15

Val Arg Met Ser Cys Lys Ser Ser Gly Tyr Ile Phe Thr Asp Phe Tyr
                20                  25                  30

Met Asn Trp Val Arg Gln Ser His Gly Lys Ser Leu Asp Tyr Ile Gly
            35                  40                  45

Tyr Ile Ser Pro Tyr Ser Gly Val Thr Gly Tyr Asn Gln Lys Phe Lys
        50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Gly Asp Tyr Trp Gly His Gly Ala Ser Val Thr Val Ser Ser
                100                 105                 110

<210> SEQ ID NO 257
```

```
<211> LENGTH: 106
<212> TYPE: PRT
<213> ORGANISM: Mus musculus

<400> SEQUENCE: 257

Gln Ile Gln Leu Val Gln Ser Gly Pro Glu Leu Lys Lys Pro Gly Glu
1               5                   10                  15

Thr Val Arg Ile Ser Cys Lys Ala Ser Asp Tyr Met Thr Ser Gly Met
            20                  25                  30

Gln Trp Val Gln Gln Met Pro Gly Lys Gly Leu Lys Trp Ile Gly Trp
        35                  40                  45

Leu Asn Thr Gln Ser Gly Val Pro Glu Tyr Ala Glu Asp Phe Lys Gly
    50                  55                  60

Arg Phe Ala Phe Ser Leu Glu Thr Thr Ala Tyr Leu Gln Ile Asn Asn
65                  70                  75                  80

Leu Lys Asn Glu Asp Thr Ala Thr Tyr Phe Cys Ala Thr Ala Tyr Trp
                85                  90                  95

Gly Gln Gly Thr Thr Leu Thr Val Ser Ser
            100                 105

<210> SEQ ID NO 258
<211> LENGTH: 110
<212> TYPE: PRT
<213> ORGANISM: Mus musculus

<400> SEQUENCE: 258

Glu Val Lys Leu Val Glu Ser Arg Gly Gly Leu Val Lys Pro Gly Gly
1               5                   10                  15

Ser Leu Gln Leu Ser Cys Ala Ala Ser Gly Phe Thr Phe Ser Gly Tyr
            20                  25                  30

Ala Met Ser Trp Phe Arg Leu Thr Pro Glu Lys Arg Leu Glu Trp Val
        35                  40                  45

Ala Ser Ile Tyr Asn Gly Phe Arg Ile His Tyr Leu Asp Ser Val Lys
    50                  55                  60

Gly Arg Phe Thr Ile Ser Ser Asp Tyr Ala Arg Asn Ile Leu Tyr Leu
65                  70                  75                  80

Gln Met Ser Thr Leu Arg Ser Glu Asp Thr Ala Met Tyr Tyr Cys Ser
                85                  90                  95

Arg Asp Val Trp Gly Ala Gly Thr Thr Val Thr Val Ser Ala
            100                 105                 110

<210> SEQ ID NO 259
<211> LENGTH: 109
<212> TYPE: PRT
<213> ORGANISM: Mus musculus

<400> SEQUENCE: 259

Val Met Leu Val Glu Ser Gly Gly Gly Leu Val Lys Pro Gly Gly Ser
1               5                   10                  15

Leu Lys Leu Ser Cys Ala Ala Ser Gly Phe Thr Phe Ser Ser Tyr Ala
            20                  25                  30

Met Ser Trp Val Arg Gln Thr Pro Glu Arg Arg Leu Glu Trp Val Ala
        35                  40                  45

Thr Ile Thr Thr Arg Gly Tyr Thr Phe Tyr Pro Asp Ser Val Lys Gly
    50                  55                  60

Arg Phe Thr Val Ser Arg Asp Asn Ala Arg Asn Thr Leu Asn Leu Gln
65                  70                  75                  80

Met Ser Ser Leu Arg Ser Glu Asp Thr Ala Met Phe Tyr Cys Thr Arg
```

```
                    85                  90                  95
Asp Tyr Trp Gly Gln Gly Thr Ser Val Thr Val Ser Ser
                100                 105

<210> SEQ ID NO 260
<211> LENGTH: 110
<212> TYPE: PRT
<213> ORGANISM: Mus musculus

<400> SEQUENCE: 260

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Arg Tyr
                 20                  25                  30

Ala Leu Ser Trp Val Arg Gln Thr Ala Asp Lys Arg Leu Glu Trp Val
             35                  40                  45

Ala Ser Ile Val Ser Gly Gly Asn Thr Tyr Tyr Ser Gly Ser Val Lys
         50                  55                  60

Gly Arg Phe Thr Ile Ser Arg Asp Ile Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Val His Trp Gly Gln Gly Thr Leu Val Thr Val Ser Ser
                100                 105                 110

<210> SEQ ID NO 261
<211> LENGTH: 110
<212> TYPE: PRT
<213> ORGANISM: Mus musculus

<400> SEQUENCE: 261

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Ser Phe Arg Asn Tyr
                 20                  25                  30

Gly Met Ser Trp Val Arg Gln Thr Pro Glu Lys Arg Leu Glu Trp Val
             35                  40                  45

Ala Ser Ile Ser Tyr Gly Gly Leu Ile Tyr Tyr Pro Asp Ser Ile Lys
         50                  55                  60

Gly Arg Phe Thr Ile Ser Arg Asp Ile Ala Gln Asn Ile Leu Tyr Leu
 65                  70                  75                  80

Gln Met Ser Ser Leu Arg Ser Glu Asp Thr Ala Met Tyr His Cys Ile
                 85                  90                  95

Arg Thr Phe Trp Gly Gln Gly Thr Leu Val Thr Val Ser Ala
                100                 105                 110

<210> SEQ ID NO 262
<211> LENGTH: 109
<212> TYPE: PRT
<213> ORGANISM: Mus musculus

<400> SEQUENCE: 262

Gln Val Gln Leu Gln Gln Ser Asp Ala Glu Leu Val Lys Pro Gly Ala
  1               5                  10                  15

Ser Val Lys Ile Ser Cys Lys Ala Ser Gly Tyr Thr Phe Thr Asp His
                 20                  25                  30

Ala Ile His Trp Val Lys Gln Lys Pro Gly Leu Glu Trp Ile Gly Tyr
             35                  40                  45
```

```
Ile Ser Pro Gly Asn Gly Asp Ile Lys Tyr Asn Glu Lys Phe Lys Gly
        50                  55                  60

Lys Ala Thr Leu Thr Ala Asp Lys Ser Ser Thr Ala Tyr Met Gln
 65                  70                  75                  80

Leu Asn Ser Leu Thr Ser Glu Asp Ser Ala Val Tyr Phe Cys Lys Met
                 85                  90                  95

Asp Tyr Trp Gly Gln Gly Thr Thr Leu Thr Val Ser Ser
                100                 105
```

<210> SEQ ID NO 263
<211> LENGTH: 110
<212> TYPE: PRT
<213> ORGANISM: Mus musculus

<400> SEQUENCE: 263

```
Val Gln Leu Gln Gln Pro Gly Ala Glu Leu Val Lys Pro Gly Ala Ser
 1               5                  10                  15

Val Lys Leu Ser Cys Lys Ala Ser Gly Tyr Thr Phe Thr Ser Asn Trp
                20                  25                  30

Ile Asn Trp Val Lys Gln Arg Pro Gly Gln Gly Leu Glu Trp Ile Gly
             35                  40                  45

Asn Ile Tyr Pro Asp Ser Tyr Arg Thr Asn Tyr Asn Glu Lys Phe Lys
         50                  55                  60

Arg Lys Ala Thr Leu Thr Val Asp Thr Ser Ser Ser Thr Ala Tyr Met
 65                  70                  75                  80

Gln Leu Ser Ser Leu Thr Ser Asp Asp Ser Ala Val Tyr Tyr Cys Val
                 85                  90                  95

Arg Val Tyr Trp Gly Gln Gly Thr Leu Val Thr Val Ser Ala
                100                 105                 110
```

<210> SEQ ID NO 264
<211> LENGTH: 97
<212> TYPE: PRT
<213> ORGANISM: Mus musculus

<400> SEQUENCE: 264

```
Leu Gln Gln Pro Gly Ala Glu Leu Val Lys Pro Gly Ala Ser Val Lys
 1               5                  10                  15

Leu Ser Cys Ser Ser Trp Ile Asn Trp Val Lys Gln Arg Pro Gly Gln
                20                  25                  30

Gly Leu Glu Trp Ile Gly Asn Val Tyr Pro Ser Thr Asn Tyr Asn Glu
             35                  40                  45

Lys Phe Lys Asn Lys Ala Thr Leu Thr Val Asp Thr Ser Ser Ser Thr
 50                  55                  60

Ala Tyr Met Gln Leu Ser Ser Leu Thr Ser Asp Asp Ser Ala Phe Tyr
 65                  70                  75                  80

Tyr Cys Val Arg Pro Tyr Trp Gly Gln Gly Thr Leu Val Thr Val Ser
                 85                  90                  95

Ala
```

<210> SEQ ID NO 265
<211> LENGTH: 110
<212> TYPE: PRT
<213> ORGANISM: Mus musculus

<400> SEQUENCE: 265

```
Val Gln Leu Gln Gln Pro Gly Ala Glu Leu Val Lys Pro Gly Ala Ser
 1               5                  10                  15
```

Val Lys Leu Ser Cys Lys Ala Ser Gly Tyr Thr Phe Thr Asn Tyr Trp
             20                  25                  30

Ile Asn Trp Val Lys Gln Arg Pro Gly Gln Gly Leu Glu Trp Ile Gly
             35                  40                  45

Asn Ile Tyr Pro Gly Ser Ser Tyr Thr His Tyr Asn Glu Lys Phe Lys
         50                  55                  60

Asn Lys Ala Thr Leu Thr Val Asp Thr Ser Ser Thr Ala Tyr Met
 65                  70                  75                  80

Gln Leu Ser Ser Leu Thr Ser Asp Asp Ser Ala Val Tyr Tyr Cys Ala
                 85                  90                  95

Asn Pro Tyr Trp Gly Gln Gly Thr Leu Val Thr Val Ser Ala
             100                 105                 110

<210> SEQ ID NO 266
<211> LENGTH: 107
<212> TYPE: PRT
<213> ORGANISM: Mus musculus

<400> SEQUENCE: 266

Val Gln Leu Gln Gln Ser Gly Ala Glu Leu Val Lys Pro Gly Ala Ser
 1               5                  10                  15

Val Lys Leu Ser Cys Lys Ala Ser Gly Tyr Thr Phe Thr Ser Tyr Trp
             20                  25                  30

Met Gln Trp Val Lys Gln Arg Pro Gly Gln Gly Leu Glu Trp Ile Gly
             35                  40                  45

Glu Ile Asp Pro Ser Asp Ser Tyr Thr Asn Tyr Asn Gln Lys Phe Lys
         50                  55                  60

Gly Lys Ala Thr Leu Thr Val Asp Ser Thr Ala Tyr Met Gln Leu Ser
 65                  70                  75                  80

Ser Leu Thr Ser Glu Asp Ser Ala Val Tyr Tyr Cys Ala Asn Asp Tyr
                 85                  90                  95

Trp Gly Gln Gly Thr Thr Leu Thr Val Ser Ser
             100                 105

<210> SEQ ID NO 267
<211> LENGTH: 111
<212> TYPE: PRT
<213> ORGANISM: Homo sapiens

<400> SEQUENCE: 267

Gln Val Gln Leu Leu Glu Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Arg Gly Leu Glu Trp Ile
             35                  40                  45

Gly Arg Ile Asp Pro Asn Ser Gly Gly Thr Lys Tyr Asn Glu Lys Phe
         50                  55                  60

Lys Ser Lys Ala Thr Leu Thr Val Asp Lys Pro Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Asp Tyr Trp Gly Ala Gly Thr Thr Val Thr Val Ser Ser
             100                 105                 110

<210> SEQ ID NO 268
<211> LENGTH: 109
<212> TYPE: PRT

<213> ORGANISM: Mus musculus

<400> SEQUENCE: 268

Val Gln Leu Gln Gln Ser Gly Pro Gly Leu Val Lys Pro Ser Gln Ser
1               5                   10                  15

Leu Ser Leu Thr Cys Thr Val Thr Gly Tyr Ser Ile Ser Asp Phe Ala
            20                  25                  30

Trp Asn Trp Ile Arg Gln Phe Pro Gly Asn Lys Leu Glu Trp Met Gly
        35                  40                  45

Tyr Ile Asn Tyr Ser Gly Phe Thr Ser His Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Ala Gly
                85                  90                  95

Gly Ser Trp Gly Gln Gly Thr Leu Val Thr Val Ser Ala
            100                 105

<210> SEQ ID NO 269
<211> LENGTH: 113
<212> TYPE: PRT
<213> ORGANISM: Mus musculus

<400> SEQUENCE: 269

Glu Val Thr Leu Gln Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Val Asp Trp Val Arg Gln Ser Pro Gly Lys Gly Leu Glu Trp Val
        35                  40                  45

Ala Glu Ile Arg Asn Lys Ala Asn Asn His Ala Thr Lys Tyr Thr Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Ser Ala Tyr Trp Gly Gln Gly Thr Leu Val Thr Val Ser
            100                 105                 110

Ala

<210> SEQ ID NO 270
<211> LENGTH: 109
<212> TYPE: PRT
<213> ORGANISM: Mus musculus

<400> SEQUENCE: 270

Val Gln Leu Gln Gln Ser Gly Pro Gly Leu Val Lys Pro Ser Gln Ser
1               5                   10                  15

Leu Ser Leu Thr Cys Thr Val Thr Gly Tyr Ser Ile Ser Asp Phe Ala
            20                  25                  30

Trp Asn Trp Ile Arg Gln Phe Pro Gly Asn Lys Leu Glu Trp Met Gly
        35                  40                  45

Tyr Ile Asn Tyr Ser Gly Phe Thr Ser His Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Ala Gly

```
                        85                  90                  95

Gly Ser Trp Gly Gln Gly Thr Leu Val Thr Val Ser Ala
            100                 105

<210> SEQ ID NO 271
<211> LENGTH: 111
<212> TYPE: PRT
<213> ORGANISM: Mus musculus

<400> SEQUENCE: 271

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Ala Arg Gln Thr Pro Glu Lys Lys Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Asp Arg Trp Gly Gln Gly Thr Ser Val Thr Val Ser Ser
            100                 105                 110

<210> SEQ ID NO 272
<211> LENGTH: 113
<212> TYPE: PRT
<213> ORGANISM: Mus musculus

<400> SEQUENCE: 272

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Met Gly Ile Tyr
                85                  90                  95

Tyr Cys Thr Ser Ala Tyr Trp Gly Gln Gly Thr Leu Val Thr Val Ser
            100                 105                 110

Ala

<210> SEQ ID NO 273
<211> LENGTH: 110
<212> TYPE: PRT
<213> ORGANISM: Mus musculus

<400> SEQUENCE: 273

Glu Val Lys Leu Leu Glu Ser Gly Gly Gly Leu Val Lys Pro Gly Gly
1               5                   10                  15

Ser Leu Lys Leu Ser Cys Thr Ala Ser Gly Ile Thr Phe Ser Arg Tyr
            20                  25                  30

Ile Met Ser Trp Val Arg Gln Ile Pro Glu Lys Arg Leu Glu Trp Val
```

-continued

```
              35                  40                  45
Ala Ser Ile Ser Ser Gly Gly Ile Thr Tyr Tyr Pro Asp Ser Val Ala
 50                  55                  60

Gly Arg Phe Thr Ile Ser Arg Asp Asn Val Arg Asn Ile Leu Tyr Leu
 65                  70                  75                  80

Gln Met Ser Ser Leu Arg Ser Glu Asp Thr Ala Leu Tyr Tyr Cys Ala
                 85                  90                  95

Arg Pro Tyr Trp Gly Gln Gly Thr Leu Val Thr Val Ser Ser
                100                 105                 110

<210> SEQ ID NO 274
<211> LENGTH: 111
<212> TYPE: PRT
<213> ORGANISM: Mus musculus

<400> SEQUENCE: 274

Gln Val Lys Leu Leu Glu Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
             35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Val Arg Asp Tyr Trp Gly Gln Gly Thr Ser Val Thr Val Ser Ser
                100                 105                 110

<210> SEQ ID NO 275
<211> LENGTH: 111
<212> TYPE: PRT
<213> ORGANISM: Mus musculus

<400> SEQUENCE: 275

Glu Val Lys Leu Gln Glu Ser Gly Ala Glu Leu Val Arg Pro Gly Ala
 1               5                  10                  15

Ser Val Lys Leu Ser Cys Lys Thr Ser Gly Tyr Ile Phe Thr Ser Tyr
                20                  25                  30

Trp Ile His Trp Val Lys Gln Arg Ala Ala Gly Leu Glu Trp Ile
             35                  40                  45

Ala Arg Ile Tyr Pro Gly Thr Gly Ser Ser Tyr Tyr Asn Val Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Lys Ser Asp Asp Ser Ala Val Tyr Phe Cys
                 85                  90                  95

Val Arg Asp Tyr Trp Gly Gln Gly Thr Leu Val Thr Val Ser Ser
                100                 105                 110

<210> SEQ ID NO 276
<211> LENGTH: 111
<212> TYPE: PRT
<213> ORGANISM: Mus musculus

<400> SEQUENCE: 276
```

Glu Met Gln Leu Gln Gln Ser Gly Ala Glu Leu Leu Arg Pro Gly Thr
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
            35                  40                  45

Ala Arg Ile Tyr Pro Gly Thr Gly Ser Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Thr Leu Lys Ser Glu Asp Ser Ala Val Tyr Phe Cys
                85                  90                  95

Thr Arg Asp Tyr Trp Gly Gln Gly Thr Leu Val Thr Val Ser Ser
            100                 105                 110

<210> SEQ ID NO 277
<211> LENGTH: 111
<212> TYPE: PRT
<213> ORGANISM: Mus musculus

<400> SEQUENCE: 277

Arg Val Gln Leu Leu Glu Ser Gly Ala Glu Leu Met Lys Pro Gly Ala
1               5                   10                  15

Ser Val Gln Ile Ser Cys Lys Ala Thr Gly Tyr Thr Phe Ser Phe Tyr
            20                  25                  30

Trp Ile Glu Trp Val Lys Glu Arg Pro Gly His Gly Leu Glu Trp Ile
            35                  40                  45

Gly Glu Ile Leu Pro Gly Ser Gly Arg Thr Asn Tyr Arg Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Tyr Trp Gly Gln Gly Thr Ser Val Thr Val Ser Ala
            100                 105                 110

<210> SEQ ID NO 278
<211> LENGTH: 111
<212> TYPE: PRT
<213> ORGANISM: Mus musculus

<400> SEQUENCE: 278

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Lys Pro Glu Gln Gly Leu Glu Trp Ile
            35                  40                  45

Ala Gln Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Ser Ala Val Tyr Tyr Cys
                85                  90                  95

Ala Ala Asp Tyr Trp Gly Gln Gly Thr Thr Leu Thr Val Ser Ser
            100                 105                 110

-continued

<210> SEQ ID NO 279
<211> LENGTH: 110
<212> TYPE: PRT
<213> ORGANISM: Mus musculus

<400> SEQUENCE: 279

Glu Val Lys Leu Ser Glu Ser Gly Pro Gly Leu Val Lys Pro Ser Gln
1               5                   10                  15

Ser Leu Ser Leu Thr Cys Thr Val Thr Gly Tyr Ser Ile Thr Asn Tyr
            20                  25                  30

Ala Trp Thr Trp Ile Arg Gln Phe Pro Gly Asn Lys Leu Glu Trp Met
        35                  40                  45

Gly Tyr Ile Arg Ser Ser Val Ile Thr Arg Tyr Asn Pro Ser Leu Lys
    50                  55                  60

Ser Arg Ile Ser Ile Thr Gln Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Asp Tyr Trp Gly Gln Gly Thr Ser Val Thr Val Ser Ser
            100                 105                 110

<210> SEQ ID NO 280
<211> LENGTH: 110
<212> TYPE: PRT
<213> ORGANISM: Mus musculus

<400> SEQUENCE: 280

Val Gln Leu Gln Gln Ser Gly Ala Glu Leu Val Arg Pro Gly Thr Ser
1               5                   10                  15

Val Lys Leu Ser Cys Lys Ala Ser Gly Tyr Ser Phe Thr Asn Tyr Trp
            20                  25                  30

Met Asn Trp Leu Arg Gln Arg Pro Gly Gln Gly Leu Asp Trp Ile Gly
        35                  40                  45

Met Ile His Pro Ser Asp Ser Glu Thr Arg Leu Asn Gln Lys Phe Lys
    50                  55                  60

Asp Lys Ala Thr Leu Thr Val Asp Arg Ser Ser Ser Thr Ala Tyr Ile
65                  70                  75                  80

Gln Leu Ser Ser Pro Thr Ser Glu Asp Ser Ala Val Tyr Tyr Cys Ala
                85                  90                  95

Arg Ala Phe Trp Gly Gln Gly Thr Leu Val Thr Val Ser Ala
            100                 105                 110

<210> SEQ ID NO 281
<211> LENGTH: 109
<212> TYPE: PRT
<213> ORGANISM: Mus musculus

<400> SEQUENCE: 281

Lys Leu Gln Glu Ser Gly Pro Glu Leu Val Lys Pro Gly Ala Ser Val
1               5                   10                  15

Lys Met Ser Cys Lys Ala Ser Gly Tyr Thr Phe Thr Ser Tyr Val Met
            20                  25                  30

His Trp Val Lys Gln Lys Pro Gly Gln Gly Leu Glu Trp Ile Gly Tyr
        35                  40                  45

Ile Asn Pro Tyr Asn Asp Gly Thr Lys Tyr Asn Glu Lys Phe Lys Gly
    50                  55                  60

Lys Ala Thr Leu Thr Ser Asp Lys Ser Ser Ser Thr Ala Tyr Met Glu
65                  70                  75                  80

-continued

```
Leu Ser Ser Leu Thr Ser Glu Asp Ser Ala Val Tyr Cys Ala Pro
                85                  90                  95

Gly Tyr Trp Gly Gln Gly Thr Thr Val Thr Val Ser Ser
            100                 105
```

<210> SEQ ID NO 282
<211> LENGTH: 110
<212> TYPE: PRT
<213> ORGANISM: Mus musculus

<400> SEQUENCE: 282

```
Glu Val Lys Leu Val Glu Ser Gly Gly Leu Val Lys Pro Gly Gly
 1               5                  10                  15

Ser Leu Lys Leu Ser Cys Ala Ala Ser Gly Phe Thr Phe Ser Asn Tyr
                20                  25                  30

Ala Met Ser Trp Val Arg Gln Thr Pro Glu Lys Arg Leu Glu Trp Val
            35                  40                  45

Val Ser Ile Ser Ser Gly Gly Ser Ile Tyr Tyr Leu Asp Ser Val Lys
        50                  55                  60

Gly Arg Phe Thr Val Ser Arg Asp Asn Ala Arg Asn Ile Leu Tyr Leu
65                  70                  75                  80

Gln Met Thr Ser Leu Arg Ser Glu Asp Thr Ala Met Tyr Phe Cys Ala
                85                  90                  95

Arg Asp Val Trp Gly Ala Gly Thr Ser Val Thr Val Ser Ser
            100                 105                 110
```

<210> SEQ ID NO 283
<211> LENGTH: 111
<212> TYPE: PRT
<213> ORGANISM: Mus musculus

<400> SEQUENCE: 283

```
Gln Val Gln Leu Gln Gln Ser Gly Pro Val Leu Val Lys Pro Gly Thr
 1               5                  10                  15

Ser Leu Lys Met Ser Cys Lys Ala Ser Gly Tyr Thr Phe Thr Ala Tyr
                20                  25                  30

Tyr Met Asn Trp Met Lys Gln Ser His Gly Lys Arg Leu Glu Trp Ile
            35                  40                  45

Ala Val Ile Asn Pro Tyr Asn Gly Phe Thr Thr Tyr Asn Gln Lys Phe
        50                  55                  60

Lys Gly Lys Ala Thr Leu Thr Val Asp Lys Ser Ser Asn Thr Ala Tyr
65                  70                  75                  80

Met Asp Leu Asn Ser Leu Thr Ser Glu Asp Ser Ala Val Tyr Tyr Cys
                85                  90                  95

Val Pro Val Tyr Trp Gly His Gly Thr Leu Val Thr Val Ser Thr
            100                 105                 110
```

<210> SEQ ID NO 284
<211> LENGTH: 109
<212> TYPE: PRT
<213> ORGANISM: Mus musculus

<400> SEQUENCE: 284

```
Glu Val Gln Leu Glu Glu Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Met Asn Trp Leu Arg Gln Lys Pro Gly Gln Gly Leu Glu Trp Ile
            35                  40                  45
```

```
Gly Trp Val Tyr Pro Gly Ser Ile Lys Tyr Asn Glu Lys Phe Lys Asp
        50                  55                  60

Lys Ala Thr Leu Thr Ala Asp Thr Ser Ser Ile Val Tyr Met His
65                  70                  75                  80

Leu Ser Ser Leu Thr Ser Asp Asp Asn Ala Val Tyr Phe Cys Thr Arg
                    85                  90                  95

Asp Tyr Trp Gly Glu Gly Thr Leu Leu Thr Val Ser Ser
            100                 105

<210> SEQ ID NO 285
<211> LENGTH: 111
<212> TYPE: PRT
<213> ORGANISM: Mus musculus

<400> SEQUENCE: 285

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Ile His Trp Asn Lys Gln Ser His Gly Lys Ser Leu Glu Trp Ile
            35                  40                  45

Gly Tyr Ile Tyr Pro Asn Asn Gly Gly Asn Gly Tyr Asn His Lys Phe
        50                  55                  60

Lys Gly Lys Ala Thr Leu Thr Val Asp Lys Ser Ser Ser Thr Ala Tyr
65                  70                  75                  80

Met Asp Val Arg Thr Leu Thr Ser Glu Asp Ser Ala Val Tyr Tyr Cys
                85                  90                  95

Gly Arg Asp Tyr Trp Gly Gln Gly Thr Thr Leu Thr Val Ser Ser
            100                 105                 110

<210> SEQ ID NO 286
<211> LENGTH: 109
<212> TYPE: PRT
<213> ORGANISM: Mus musculus

<400> SEQUENCE: 286

Gln Val Gln Leu Val Glu Ser Gly Pro Gly Leu Val Ala Pro Ser Gln
1               5                   10                  15

Ser Leu Ser Ile Thr Cys Thr Val Ser Gly Ile Ser Leu Ser Arg Tyr
                20                  25                  30

Asn Val His Trp Val Arg Gln Ser Pro Gly Lys Gly Leu Glu Trp Leu
            35                  40                  45

Gly Met Ile Trp Gly Gly Gly Ser Ile Glu Tyr Asn Pro Ala Leu Lys
        50                  55                  60

Ser Arg Leu Ser Ile Ser Lys Asp Asn Ser Lys Ser Gln Ile Phe Leu
65                  70                  75                  80

Lys Met Asn Ser Leu Gln Thr Asp Asp Ser Ala Met Tyr Tyr Cys Val
                85                  90                  95

Ser Ser Tyr Trp Gly Gln Gly Thr Leu Val Thr Val Ser
            100                 105
```

METHODS OF AFFINITY MATURING ANTIBODIES

CROSS-REFERENCE TO RELATED APPLICATIONS

This applications claims the benefit of U.S. Provisional Application Ser. No. 61/251445, filed 14 Oct. 2009, the entire contents of which is incorporated herein by reference in its entirety.

FIELD OF THE INVENTION

The invention relates to methods of affinity maturing antibodies.

BACKGROUND OF THE INVENTION

Generation of antibodies for therapeutic uses typically involves a lead discovery phase followed by an optimization process (Almagro and Strohl, Antibody Engineering: Humanization, Affinity Maturation and Selection Methods. 307-327. In: Therapeutic Monoclonal Antibodies: From Bench to Clinic. Ed. Zhiqiang An. John Wiley & Sons, Inc. 2009). The platforms currently available for lead discovery include hybridoma technology (Kohler et al., Nature, 256: 495-7, 1975), in vitro display-based technologies (Hoogenboom, Nat Biotechnol, 23:1105-16, 2005), and transgenic mice expressing human immunoglobulins (Lonberg et al., Nature 368:856-9, 1994). In a typical antibody lead development campaign, optimization of initial discovery hits is typically required to improve affinity, solubility and stability.

A number of strategies to increase affinity of antibodies have been reported, including random (Groves et al., J Immunol Methods, 313:129-39, 2006) and site-directed mutagenesis (SDM) methods (Barbas et al., Proc Natl Acad Sci USA, 91:3809-13, 1994), combined with for example in vitro display-based technologies such as phage or ribosome display to generate libraries of variants for subsequent screens (Almagro and Strohl, Antibody Engineering: Humanization, Affinity Maturation and Selection Methods. 307-327. In: Therapeutic Monoclonal Antibodies: From Bench to Clinic. Ed. Zhiqiang An. John Wiley & Sons, Inc. 2009). However, only a limited number of residues can be diversified as the size of the libraries increases exponentially for every diversified residue. For example, a library built on the common NNK diversification scheme, which introduces 32 codons in every position, grows by $32^n$ for every n number of residues. Phage libraries are normally limited to a size of $10^9$-$10^{10}$ members, indicating that only 6-7 residues can be diversified if full sequence coverage is to be achieved in the library.

Strategies for diversification to attain maximal sequence coverage include generation of antibody libraries by targeting solvent accessible antibody residues (US2005/0266000), or targeting residues based on sequence comparisons (WO2006/014498). More focused strategies include diversification of residues at HCDR3 (Schier et al., J Mol Biol 263:551-67, 2006) since it is well known that this region of the antigen-binding site is often critical to define the specificity and affinity of antibodies. The diversity of the libraries has been designed in some cases to mirror the composition and frequency of amino acids in natural antibodies (Cobaugh et al., J Mol Biol, 378:622-33, 2008; Knappik et al., J Mol Biol, 296:57-86, 2000; Lee et al., J Mol Biol, 340:1073-93, 2004; Hoet et al., Nature Biotechnol, 23:344-8, 2005). Also, a combinations of a few amino acids (Fellouse et al., Proc Natl Acad Sci USA, 101: 12467-72, 2004; Sidhu and Fellouse, Nature Chemical Biology, 2:682-8, 2006), or a binary code restricted to tyrosine and serine (Fellouse et al., J Mol Biol, 348:1153-62, 2005) have been used.

Developing therapeutic antibodies with higher affinity can have a direct impact on efficacy as well as on dosage and hence, potential immunogenicity and production costs. Thus, there is a need for improved methods for affinity maturing antibodies.

SUMMARY OF THE INVENTION

One aspect of the invention is a method of affinity maturing an antibody, comprising the steps of:
a. obtaining an amino acid sequence of the antibody light chain variable region (VL) or the antibody heavy chain variable region (VH);
b. identifying rSDRU residues in the amino acid sequence of the antibody VL or VH;
c. selecting a subset of the rSDRU residues to be diversified;
d. selecting a set of amino acids used for diversifying the subset of the rSDRU residues;
e. preparing a library of antibody VL or VH variants by diversifying the subset of the rSDRU residues selected in step c. with the set of amino acids selected in step d.;
f. expressing the library of antibody VH or VL variants in a host or translating the library of antibody VH or VL variants in vitro; and
g. selecting from the library of antibody VH or VL variants one or more affinity matured antibody having an improved affinity to an antigen.

BRIEF DESCRIPTION OF THE FIGURES

FIG. 1. Correspondence between Kabat and Chothia numbering for the antibody V kappa chain. Positions of CDRs, HVLs, and rSDRU residues are indicated in black in corresponding columns. Only V kappa residues around CDRs are shown.

FIG. 2. Correspondence between Kabat and Chothia numbering for the antibody VH chain. Positions of CDRs, HVLs, and rSDRU residues are indicated in black in corresponding columns. Only VH residues around CDRs are shown.

FIG. 3. Crystal structures of antibody-antigen complexes used to determine rSDRU.

FIG. 4. Polypeptide sequences of the V kappa chains of antibodies used to determine rSDRU for A) anti-protein, B) anti-peptide, and C) anti-hapten antibodies. V kappa residues in contact with the antigen in the crystal structures of antibody/antigen complexes are highlighted in gray. Alignment in L3 follows IMGT's conventions (Lefranc et al., Dev Comp Immunol, 27: 55-77, 2003) instead of Chothia and Kabat. SDRR sequences are shown. The amino acid sequences of antibody V kappa chains are shown in A) SEQ ID NOs: 1-67 B) SEQ ID NOs: 68-96 and C) SEQ ID NOs: 97-143 listed in the order of from the top to the bottom in the Figure.

FIG. 5. Polypeptide sequences of the VH chains of antibodies used to determine rSDRU for A) anti-protein, B) anti-peptide, and C) anti-hapten antibodies. VH residues in contact with the antigen in the crystal structures of antibody/antigen complexes are highlighted in gray. Numbering and alignment in H1 and H2 loops was manually curated to conform to Chothia's conventions (Chothia and Lesk, Mol Biol, 196:901-17, 1987). SDRR sequences are shown. The amino acid sequences of antibody VH chains are shown in A) SEQ ID NOs: 144-210 B) SEQ ID NOs: 211-239 and C) SEQ ID NOs: 240-286 listed in the order of from the top to the bottom in the Figure.

FIG. 7. V kappa SDRM for A) anti-protein, B) anti-peptide, and C) anti-hapten antibody.

FIG. 8. VH SDRM for A) anti-protein, B) anti-peptide; and C) anti-hapten antibody.

DETAILED DESCRIPTION OF THE INVENTION

Figure 6A:
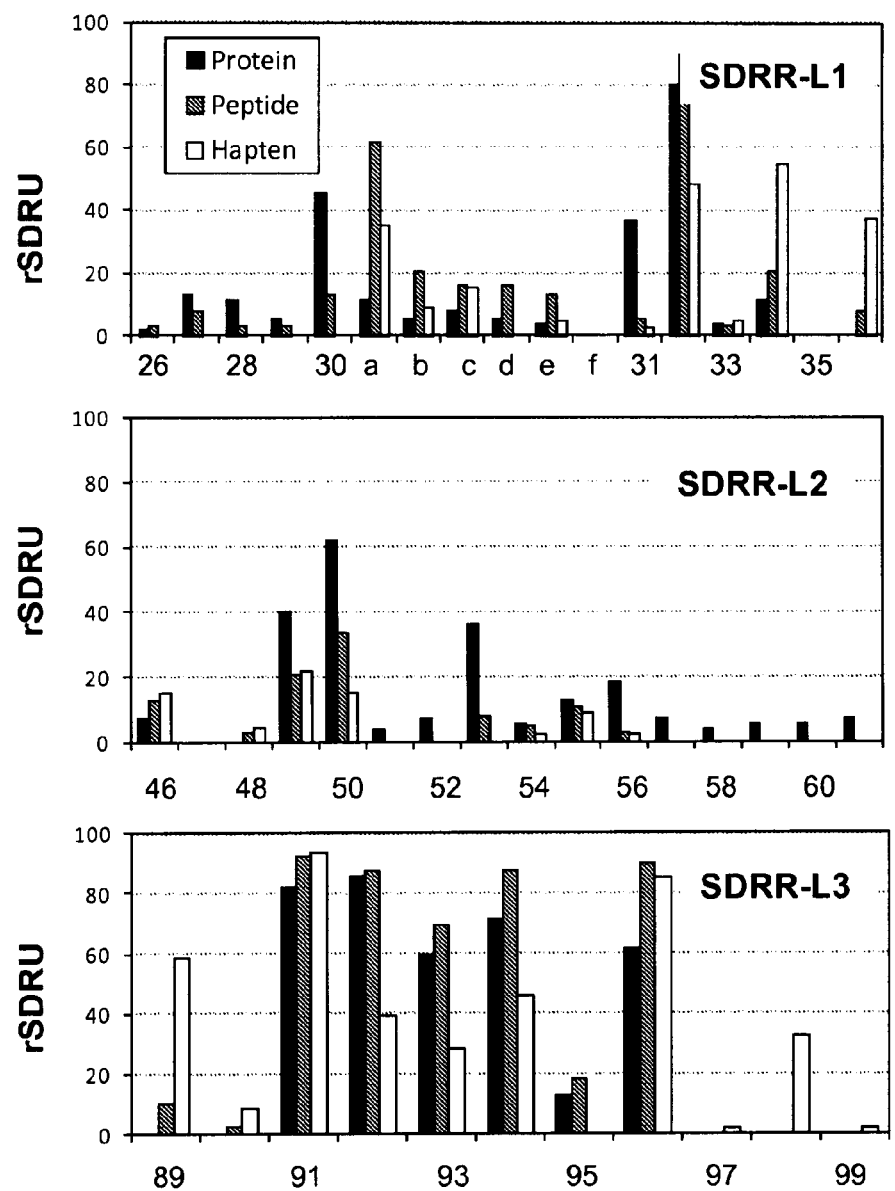
FIG. 6. Frequency (rSDRU) of antibody contacts with the indicated antigen for A) V kappa and B) VH.

All publications, including but not limited to patents and patent applications, cited in this specification are incorporated by reference as though fully set forth herein.

As used herein and in the claims, the singular forms "a," "an" and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "antibody" includes whole antibodies and any fragments thereof. Antibody fragments comprise at least a portion of an immunoglobulin molecule, such as a complementarity determining region (CDR), a variable region (V), a constant (C) region, or a framework region (FR) from either antibody heavy or light chain. Immunoglobulins can be assigned to five major classes, namely IgA, IgD, IgE, IgG and IgM, depending on the heavy chain C domain amino acid sequence. IgA and IgG are further sub-classified as the isotypes $IgA_1$, $IgA_2$, $IgG_1$, $IgG_2$, $IgG_3$ and $IgG_4$.

An antibody may be a Fab, F(ab'), F(ab')$_2$, scFv, dsFv, or diabody. An antibody may be a monoclonal antibody (mAb), chimeric, humanized, or human antibody, dimeric, tetrameric or multimeric. Structures of the above mentioned antibody fragments, and techniques for the preparation and use of the antibodies and fragments thereof are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature, 256:495-7, 1975; Queen et al., Proc Natl Acad Sci USA, 86:10029-33, 1989; U.S. Pat. No. 4,816,567).

An antibody "light chain variable region" (VL) and an antibody "heavy chain variable region" (VH) as used herein refer to well known portions of the light chain and heavy chain of antibody molecules that include amino acid sequences of antigen-binding sites (for example CDR1, CDR2, CDR3) and frameworks (FRs, i.e., FR1, FR2, FR3, FR4). The light chain variable region (VL) can be kappa or lambda and is encoded by antibody IGVK or IGVL and IGJK or IGJL genes, and the heavy chain variable region (VH) is encoded by antibody IGVH, IGDH, and IGJH genes.

Genomic organization of the human heavy and light chain gene loci, antibody gene structures and gene rearrangements are well known.

"Affinity" as used herein refers to the measure of the strength of binding between an antibody and an antigen. The affinity of an antibody can be represented, for example, by measuring affinity using a single point ELISA, or by the dissociation constant (Kd). Typically, the antibody dissociates from the antigen-antibody complex with a constant ($K_D$) of $10^{-7}$ M or less, $10^{-8}$ M or less, $10^{-9}$ M or less or $10^{-10}$ M or less.

"Improved affinity" as used herein refers to at least a two-fold higher ELISA signal in a single point ELISA assay or at least a two-fold reduction in Kd of an affinity-matured antibody compared to its parent antibody.

An "affinity-matured antibody" as used herein is an antibody or a fragment thereof with one or more amino acid substitutions in a variable region, which results in improved affinity of the antibody for an antigen, compared to a parent antibody which does not possess those substitutions. An exemplary affinity-matured antibody has substitutions in at least one rSDRU residue.

"Contact" or "contacts" or "in contact" as used herein refers to antibody VL or VH residue which have a heavy atom at a distance between about 2.5 Å and 4.5 Å with any heavy atom of an antigen in complex with the antibody in the x, y and z coordinates of the x-ray antibody/antigen complex crystallographic structure.

"Relative Specificity Determining Residue Usage", "rSDRU", as used herein refers to the frequency of contacts in an antibody heavy chain or light chain in a collection of crystal structures of antibodies in complex with similar types of antigens, for example protein, peptide or hapten antigens. rSDRU is defined as:

$$rSDRU(i) = \left(\left(\sum_{i=1}^{n} Ni\right)/n\right) * 100$$

where Ni defines a count for residue contacts with an antigen at Chothia residue i in the antibody chain. Ni=1 when the antibody residue contacts the antigen, and 0 if it does not. "n" is the number of analyzed crystal structures of antibody/antigen complexes. For example, rSDRU(50)=36 means that 36% of the antibodies analyzed contact their antigen at heavy or light chain Chothia residue 50 (e.g., the rSDRU value at residue 50 is 36). Low rSDRU refers to rSDRU values between 5-15, medium rSDRU to rSDRU values between 15-40, and high rSDRU to rSDRU values over 40. A residue is a "rSDRU residue" as used herein, when the calculated rSDRU value at that residue is ≥5 (e.g., rSDRU≥5).

"Specificity Determining Residue Matrix", "SDRM", as used herein refers to the frequencies of each amino acid j at any given rSDRU residue i, and is defined as:

$$SDRM(i, j) = \left(\sum_{k=1}^{n} M_{ij}\right) / \left(\sum_{k=1}^{n} \sum_{j=20}^{20} M_{ij}\right) \times 100$$

Mij defines a count for a particular amino acid residue at a rSDRU residue i in the antibody. Mij=1 if the particular amino acid residue (for example Ala) is at the rSDRU residue i, otherwise Mij=0. "n" is the number of antibody/antigen crystal structure complexes analyzed. For example, SDRM(50, Ala)=42 means that Ala contributes to 42% of the contacts at residue 50.

The term "Specificity Determining Residues Region" or "SDRR" as used herein refers to five distinct regions of amino acid contacts in both V kappa and VH. There are three regions in V kappa, SDRR-L1, SDRR-L2, and SDRR-L3, and two regions in VH, SDRR-H1 and SDRR-H2. The SDRR partially overlap with CDRs and HVLs, and their location is shown in Table 2.

The term "polypeptide" or "protein" means a molecule that comprises at least two amino acid residues linked by a peptide bond to form a polypeptide. Small polypeptides of less than 50 amino acids may be referred to as "peptides".

The term "hapten" as used herein means a small organic compound bound to the antigen-binding site of an antibody.

The term "antigen" as used herein is a molecule that is bound by an antibody. Antigens can be classified to different types, such as proteins, peptides and haptens. "Antibodies that bind similar types of antigens" are a group of antibodies that bind antigens classified to one type, e.g., protein, peptide or hapten.

"Fusion Protein" as used herein means a molecule having at least two peptides or proteins or a combination thereof linked into one continuous polypeptide. The at least two peptides or proteins linked in a fusion protein are typically derived from two independent sources, and therefore a fusion polypeptide often comprises two linked proteins not normally found linked in nature. The linking sequences are well known, and include, for example, an amide bond or a glycine-rich linker. Exemplary fusion proteins are VL and VH fusions with bacteriophage coat proteins, for example pIII, pVII, or pIX (Gao et al., Proc Natl Acad Sci USA, 96:6025-30, 1999). Fusion proteins are made using well known methods, for example recombinant expression after routine cloning.

"Desired biological activity" of an antibody includes, for example, enhanced or modified binding, enhanced or modified affinity, on-rate, off-rate, specificity, half-life, reduced immunogeneicity, efficient expression and production from a variety of hosts, antibody stability, and good solution properties, or any other suitable characteristic.

The term "substituting" or "variegating" or "mutating" or "diversifying" can be used interchangeably and as used herein refers to altering one or more amino acids or nucleotides in a polypeptide or polynucleotide sequence to generate a variant of that sequence.

"Variant" as used herein refers to a polypeptide or polynucleotide that differs from a reference polypeptide or polynucleotide and may or may not have altered properties. A variant and reference polypeptide may differ in amino acid sequence by one or more modifications for example, substitutions, insertions or deletions.

"Library" as used herein refers to a collection of two or more variants.

Various numbering systems are in use to identify antibody VH and VL residues. Correspondence between the most two used numbering systems, Kabat (Kabat et al., Sequences of Immunological Interest, 5$^{th}$ Ed. Public Health Service, NIH, Bethesda, Md., 1991) and Chothia (Chothia and Lesk, Mol Biol, 196:901-17, 1987) as well as CDRs (Kabat et al., Sequences of Proteins of Immunological Interest, 5th Ed. Public Health Service, National Institutes of Health, Bethesda, Md., 1991), hypervariable loops (HVs, HRLs) (Chothia and Lesk, Mol Biol, 196:901-17, 1987), and rSDRU residues are shown in FIGS. 1 and 2 for antibody VL and VH, respectively. In this application, all antibody light and heavy chain numbering is according to Chothia unless specified otherwise.

"Chothia residues" are the antibody light and heavy chain residues numbered according to Al-Lazikani (Al-Lazikani et al., J Mol Biol, 273:927-48, 1997).

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

The present invention provides methods of affinity maturing antibodies utilizing focused approaches to generate libraries of antibody VL and VH variants. The invention is based, at least part, on a finding that libraries yielding antibodies with the highest level of improved affinity can be generated by restricting library diversity to a limited number of VH and VL residues (e.g., a subset of rSDRU residues) and generating the variants utilizing defined sets of amino acids frequently found in contact with antigen in crystal structures of antibody/antigen complexes. Library designs are dependent on the desired library size and the type of antigen the library will be screened against.

Selecting Positions for Diversification

Determining the location and frequency of residues in contact separately for antibodies binding different types of antigens (e.g., proteins, peptides or haptens) (e.g., rSDRU) utilizing existing crystal structures of antibody/antigen complexes, provides a measure for the likelihood that a particular Chothia residue in any antibody contacts an antigen. This knowledge can be used to design focused libraries of variants with the goal of diversifying only a limited number of antibody light or heavy chain residues that bind the target antigen. The focused libraries can be designed and constructed even in the absence of crystal structure information for the particular antibody-antigen complex. The resulting libraries can be used for affinity maturation of existing antibodies. The libraries can also be used for screening campaigns for de novo antibody discovery. Designing diversity at restricted residues will increase the functionality of the library by avoiding unnecessary diversification of residues not involving in the recognition of the antigen, e.g., neutral mutations and/or amino acid residues that are deleterious to the antibody. A higher functionality of the library should increase the hit rate (number of positive clones producing antigen "binders"), diversity of the selected clones and likelihood of obtaining higher affinity, more soluble and more stable antibodies.

In the methods of the invention, the libraries are diversified at a subset of rSDRU residues as defined herein.

Figure 4A:
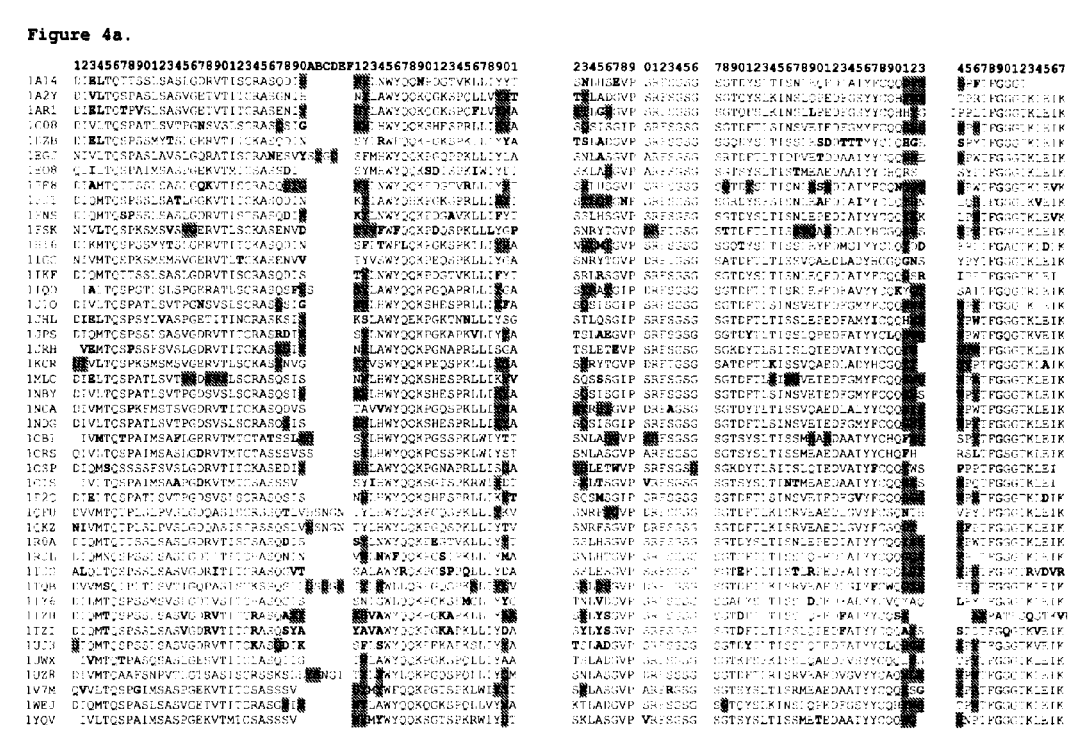
Figure 6B:
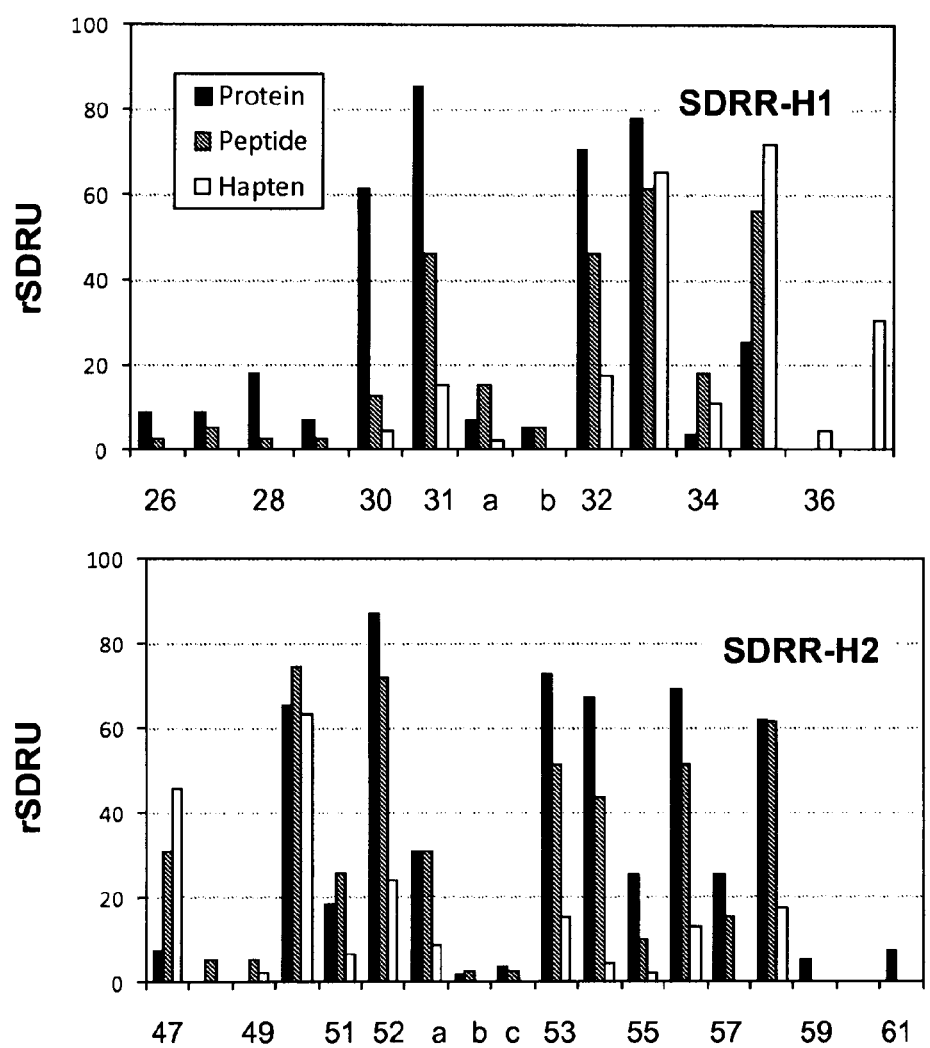

Antibody VL and VH residues in contact with antigen are identifed by analyzing crystal structures of antibody-antigen complexes available in public databases, for example the Protein Bata Bank (PDB; www_pdb_org). The Immunogenetic Database (IMGT; www_imgt_cines_fr) compiles crystal structure information and provides the VL and VH polypeptide sequences of antibodies having a crystal structure in complex to its antigen (FIG. 3). The VL and VH sequences are aligned with other antibody sequences that bind similar types of antigen. The antibody residues in contact with their respective antigens are indicated in the alignments (FIGS. 4 and 5), and rSDRUs indicating the frequency of contacts of a particular VH or VL residue with a similar type of antigen are determined within the downloaded dataset (FIGS. 6 and 7).

As the datasets evolve by incorporation of new solved antibody structures in complex with diverse antigens, it is possible that the location and/or frequency of the contacts within an expanded dataset, and thus the defined rSDRUs, may change. Large fluctuation is, however, not expected, as 3-fold expansion of the analyzed data set used in the methods of the invention resulted in only slight differences in the frequency of residues in contact (Almagro, J Mol Recognit, 172:132-43, 2004).

Antibody structures in complex with their antigens utilized in the invention to determine rSDRU are shown in FIG. 3. The VL and VH residues in contact with the antigen in the crystal structures of antibody/antigen complexes are highlighted in gray in FIGS. 4 and 5, respectively. FIG. 6 shows the frequencies of contacts for each residue for V kappa and VH for anti-protein, anti-peptide or anti-hapten antibodies.

rSDRU was calculated according to the rSDRU formula shown above separately for each residue for antibodies binding similar types of antigens. rSDRU residues were identified as residues wherein the rSDRU value was equal or over 5, e.g., residues that are in contact with antigen in more than 5% of analyzed crystal structures of antibody-antigen complexes. Table 1 shows the rSDRU residues in VL and VH domains for anti-protein, anti-peptide, and anti-hapten antibodies. The rSDRU values were assigned as low rSDRU (L); e.g., rSDRU values between 5-15, medium rSDRU (M); e.g., rSDRU values between 15-40, and high rSDRU (H); e.g., rSDRU values over 40. The Specificity Determining Residue Regions (SDRR) for anti-protein, anti-peptide and anti-hapten antibodies are shown in Table 2.

TABLE 1

| SDRR-L1 | 27 | 28 | 30 | 30A | 30B | 30C | 30D | 30E | 31 | 32 | 34 | 36 |
|---|---|---|---|---|---|---|---|---|---|---|---|---|
| Proteins | L | L | M | L | L | L | L | L | M | H | L | |
| Peptides | | M | | H | M | M | L | M | | H | M | L |
| Haptens | | | | M | L | L | | L | | M | M | L |

| SDRR-L2 | | | 49 | | 50 | | 53 | | 55 | | 56 | |
|---|---|---|---|---|---|---|---|---|---|---|---|---|
| Proteins | | | M | | H | | M | | L | | L | |
| Peptides | | | L | | M | | | | | | | |
| Haptens | | | L | | L | | | | | | | |

| SDRR-L3 | | 89 | 90 | 91 | 92 | 93 | 94 | 95 | 96 |
|---|---|---|---|---|---|---|---|---|---|
| Proteins | | | | H | H | H | H | L | M |
| Peptides | | L | | H | H | H | H | L | L |
| Haptens | | L | L | H | M | L | L | | M |

| SDRR-H1 | | 27 | 28 | 30 | 31 | 32 | 33 | 35 |
|---|---|---|---|---|---|---|---|---|
| Proteins | | L | L | H | H | H | H | M |
| Peptides | | | | L | M | M | M | H |
| Haptens | | | | L | L | L | M | H |

| SDRR-H2 | 47 | 50 | 51 | 52 | 52A | 53 | 54 | 55 | 56 | 57 | 58 |
|---|---|---|---|---|---|---|---|---|---|---|---|
| Proteins | | H | L | H | M | H | H | M | H | M | H |
| Peptides | L | H | L | H | M | H | H | M | H | L | H |
| Haptens | M | M | | M | | L | | | | | L |

Depending on the degree of desired diversity and sequence coverage of the libraries, different subsets of rSDRU residues can be selected for diversification. For example, subsets of rSDRU residues in VL or VH having rSDRU>5, rSDRU>15, rSDRU>30, rSDRU>40, rSDRU>50, rSDRU>60, or having rSDRU values between 5-15, 15-30, 15-40, 15-50, 15-60, 40-50, or 40-60 can be chosen for diversification. "Subset of rSDRU residues" as used herein refers to a group of residues having a defined rSDRU value range. For example, a subset of rSDRU residues can consist of residues 30, 31, 49, 53, and 96 (e.g., VL residues having rSDRu values between 15-40). Subsets of rSDRU residues chosen to be diversified differ depending on the type of antigen the antibody binds. In an exemplary diversification scheme of VL, residues 32, 50, 91, 92, 93, 94, and 96 are diversified, e.g., a subset set of rSDRU residues having rSDRU>30 in anti-protein antibodies. In an exemplary diversification scheme of VH, residues 31, 32, 33, 35, 50, 52, 53, 54, 55, 56, and 58 are diversified, e.g., a subset of rSDRU residues having rSDRU>60 in anti-peptide antibodies.

TABLE 2

| | SDRR-L1 | SDRR-L2 | SDRR-L3 | SDRR-H1 | SDRR-H2 |
|---|---|---|---|---|---|
| Anti-Protein | 27-34 | 49-56 | 91-96 | 26-35 | 50-58 |
| Anti-Peptide | 30-36 | 49-50 | 89-96 | 30-35 | 47-58 |
| Anti Hapten | 30-36 | 49-50 | 89-96 | 30-35 | 47-58 |

In the methods of the invention, additional considerations may be included when determining diversification schemes to generate libraries of antibody variants to improve the functionality of the library. The library design can be refined by mapping the rSDRU residues into the x-ray structure of the Fv. In the absence of the experimental x-ray structure, a 3D model of the Fv can be used. A website for automated antibody modeling based on the canonical structure model called PIGS (Automatic Prediction of ImmunoGlobulin Structures) can be found at http://arianna_bio_uniromal_it/pigs/. An antibody modeling procedure based on sequence homology with respect to antibodies of known structure has been developed by Accelrys Inc. as part of their Life Sciences modeling and simulation software in Discovery Studio (http://accelrys_com/products/discovery-studio/). PIGS and Discovery Studio generate models with a reasonable precision at VL and most of VH.

In the structure or model, the rSDRU residues can be evaluated for their exposure to the solvent as well as positioning to establish contacts with antigens. For example, insertion of residues at the hypervariable loop (HVL) L1 can change the relative orientation of residues 30 and 31, as well as interfere with residues at HVL L2. Insertions at HVL H2 or different canonical structures at this loop can expose or bury residues at the tip of the HVL H2 (residues 50-54). Long or short HVL H3 loops can also play a role in exposing or hindering residues at HVLs L3, L1 and H2. Thus, the structure or the model can be used to maximize the number of rSDRU residues with a higher probability of making contacts with the antigen for a given Fv. i.e., solvent exposure, direction in which the side chains are pointing to and size and nature of the side-chains (polar, small, aromatic) used to diversify the rSDRU residues. For example, if the side chains of the residues in a given rSDRU residue are not solvent exposed, or do not point to antigen, that rSDRU residue may not be targeted for diversification.

In an exemplary design, the positions targeted for diversification include rSDRU residues 32, 50, 91, 92, 93, 94, and 96, (e.g., rSDRU residues with rSDRU>30) in an antibody having a V kappa B3 chain, or a variant of the B3 chain, such as the anti-OSM antibody VL chains of example 3. A 3D model of B3 indicates that out of six residues in the HVL L1 insertion at B3, residues 30a, 30c, 30d, and 30f point towards the antigen binding site, and thus can be targeted for diversification, even though these residues have rSDRU values between 5-15, due to the lack of a sufficient number of crystal structures having that insertion in the database (see FIG. 4).

Polypeptides that can be used as templates for diversification include polypeptides encoding antibody light or heavy chains, or fragments thereof, for example VL and VH. The polypeptides may be naturally occurring or synthetic. Exemplary templates include antibody variable domain sequences of anti-OSM antibodies of the invention described in Example 3.

Generation of Variants

Determining the distribution of amino acids at each rSDRU residue identifies sets of amino acids favored by antibodies to contact different types of antigens at antigen-antibody complexes of known structure. These sets of amino acids can be utilized to diversify libraries in a focused manner to maximize the coverage of the library. In the methods of the invention, diversifying restricted subsets of rSDRU residues with sets of amino acids where diversity was skewed towards natural diversity identified at antibody contacts in existing antibody-antigen structures, yielded collections of antibodies improved properties over libraries with random diversity at identical subsets of rSDRU residues. The generated focused libraries can be used for affinity maturation of existing antibodies. The libraries can also be used for screening campaigns for de novo antibody discovery.

In the methods of the invention, the libraries are diversified at subsets of rSDRU residues using sets of amino acids as defined herein.

Amino acid frequencies at each rSDRU residue were determined by analyzing crystal structures of available antibody-antigen complexes. Frequencies were determined according to the SDRM formula described above for each rSDRU residue separately for V kappa and VH for anti-protein, anti-peptide and anti-hapten antibodies (FIGS. 7 and 8). For example, amino acids Q and E were found present in 71% and 28% of analyzed crystal structures of antibodies in complex with protein antigens at V kappa residue 27 (FIG. 7A). Amino acids I, K, S an T were found present in 8%, 11%, 26%, and 52% of analyzed crystal structures of antibodies in complex with antigen and VH residue 30.

"A set of amino acids" as used herein refers to the group of amino acids present at each defined rSDRU position in crystal structures of antibody-antigen complexes in the analyzed dataset. Representative sets of amino acids are shown in FIGS. 7 and 8. For example, a "set of amino acids" can consist of amino acids I, K, S, and T, e.g., a group of amino acids identified at VH rSDRU residue 30 in anti-protein antibodies (FIG. 8a). A different "set of amino acids" can consist of amino acids G, F, and Y, e.g., a group of amino acids identified at VH rSDRU residue 32 in anti-peptide antibodies (FIG. 8b).

Each selected rSDRU residue can be diversified using the set of amino acids that is present at the selected rSDRU residue in V kappa and VH sequences in antibodies binding similar types of antigens.

A frequency cutoff can be implemented to limit the number of amino acids used to diversify a particular rSDRU residue, and may be necessary in instances for example where the resulting library size would become larger than desired. For example, amino acids identified at more than 5%, 10%, 15%, 20%, 25%, 30%, 35%, 40%, 45%, 50%, 55%, 60%, 65%, 70%, 75%, 80%, 85%, 90%, 95%, or 99% frequency at a particular rSDRU residue can be used for diversification of that rSDRU residue. Thus, a "set of amino acids" can consist of amino acids K, S, and T, e.g., a group of amino acids identified at VH rSDRU residue 30 in anti-protein antibodies (FIG. 8a), or amino acid Y, e.g., a group of amino acids identified at VH rSDRU residue 32 in anti-peptide antibodies when frequency cutoff is set at 10% (FIG. 8b). In an exemplary diversification scheme, the anti-protein antibody V kappa residue 30 can be diversified using amino acids NGHKSY, NGHKSY, or GSY, depending on desired frequency stringency at that particular rSDRU residue (no cutoff, 5%, and 10%, respectively). Similarly, an anti-protein antibody VH residue 50 can be diversified using amino acids RNEGLMSTWYV, EGLTWY, or EWY, depending on the desired frequency stringency (no cutoff, 5%, and 10%, respectively) (FIGS. 7 and 8).

Frequency of the amino acids in contact with antigen can be determined not only independently for each rSDRU residue as described above, but also collectively for all rSDRU residues located in both VL and VH chains. The "universal set of amino acids" as used herein refers to a group of amino acids most frequently present at all rSDRU residues in both heavy and light chain antibodies. The "universal set of amino acids" can consist of amino acids R, N, D, G, H, S, W, and Y, (RNDGHSWY) or of amino acids R, N, D, G, H, S, and Y, (RNDGHSY) or of amino acids R, N, D, G, H, W, and Y, (RNDGHSY) or of amino acids R, D, H, S, W, Y, and G (RDGHSWY). Together these amino acids provide a broad range of molecular recognition properties. The universal set of amino acids may be used for diversification of some of all rSDRU residues if maximal diversity is to be generated at those positions, for instance, to focus diversify at rSDRU residues at SDRR-L1, SDRR-L2, SDRR-L3, SDRR-H1, and SDRR-H2. The universal set of amino acids can also be used to simplify the design and synthesis of the library since the same mix of codons can be employed in all the positions to be diversified. The universal set of amino acids can be used to diversify residues having minimal data on contacts, thus resulting in artificially low rSDRU values for that residue. Such exemplary residues are residues at HVL L1 insertions (residues 30a-30f), H2 insertions (residues 52a-d) and L3 insertions (residues 95a-c) or in synthetic insertion at a given HVL that forms the antigen-binding site.

Antibodies, as any other proteins, are prone to a variety of physical and/or chemical instabilities, resulting in adverse effects on the downstream processing of antibody-based drugs. For instance, physical and chemical instability may lead to aggregation, degradation, low product yield, loss of potency, increased potential for immunogenicity, molecular heterogeneity, and loss of activity. Thus, care is taken during design of libraries of antibody variants to minimize the presence of possible instability-inducing residues and recognition sequences.

For example, surface exposed Met and Trp may be oxidized in storage conditions, possibly leading to loss in antibody potency. Thus, Met and Trp may be omitted from the universal set of amino acids used to diversify rSDRU residues that are exposed to solvent. If the rSDRU residue is not exposed to solvent, Trp may be included but Ser may be omitted. Further, if several rSDRUs converge into the same region of the antigen-binding site, Trp may be omitted from the universal set of amino acids to prevent interference due to the large size of Trp.

Presence of Asn in a universal set of amino acids may generate well known N-glycosylation recognition sites (NXS/T) in a library depending on the neighbouring sequence. Asn may be removed from the universal set of amino acids if the rSDRU residue diversified is followed by residues that would generate the N-glycosylation site. Asn may be deamidated in proteins when followed by Gly in sequence, possible generating heterogeneicity (Robinson Proc Natl Acad Sci USA, 99:5283-8, 2002) and thus Asn may be removed from the universal set of amino acids when used to diversify rSDRU residue followed by Gly, or replaced by Gln.

Similarly, Trp and Asn may be removed from any or all sets of amino acids used to diversify one or more rSDRU residue. Alternatively, Trp and Asn may be retained at a low level, e.g., at 1%, 2%, 3%, 4%, 5%, 6%, 7%, 8%, 9%, 10%, 15%, or 20% in the sets of amino acids used to diversify any antibody library.

In an exemplary diversification scheme, V kappa rSDRU residues 30a, 30c, 30d, 30f, 32, 50, 91, 92, 93, 94, and 96 are diversified with RNDGHSY, RNDGHWY, RNDGHSY, RNDGHWY, RNDY, YWNK, SYGH, SYGN, STER, WYSH, and YRWL, respectively, in anti-protein antibodies.

One embodiment of the invention is a method of affinity-maturating an antibody, comprising the steps of:
a. obtaining an amino acid sequence of the antibody light chain variable region (VL) or the antibody heavy chain variable region (VH);
b. identifying rSDRU residues in the amino acid sequence of the antibody VL or VH;
c. selecting a subset of the rSDRU residues to be diversified;
d. selecting a set of amino acids or a universal set of amino acids used for diversifying the subset of the rSDRU residues;
e. preparing a library of antibody VL or VH variants by diversifying the subset of the rSDRU residues selected in step c. with the set of amino acids selected in step d.;
f. expressing the library of antibody VH or VL variants in a host or translating the library of antibody VH or VL variants in vitro; and
g. selecting from the library of antibody VH or VL variants one or more affinity matured antibody having an improved affinity to an antigen.

Amino acid sequences of VH or VL can be obtained using routine sequencing methods.

The rSDRU residues can be identified as described above. The number of rSDRU residues chosen for diversification depends on the desired complexity of the resulting library. A subset of rSDRU residues having rSDRU values between 5 and 15, e.g., low usage rSDRU esidues may be chosen for diversification. In other instances, a subset of rSDRU residues having rSDRU>40, e.g., high usage rSDRU residues may be chosen for diversification. For affinity-maturation of antibodies, rSDRU residues residing in either V kappa or VH may be diversified. The sets of amino acids chosen to diversify selected subsets of rSDRU residues are described above. The set of amino acids and the universal set of amino acids selected depends on the required antibody affinity, type of antigen, size of the library to be generated, desired content of hydrophobic/hydrophilic residues, and on the desire to reduce frequency of amino acid residues that may provide unbeneficial antibody characteristics, e.g., Trp, Met and Asn.

Generation of antibody variants and construction of the libraries is typically achieved at the nucleic acid level. The libraries of antibody variants with biased amino acid distribution at positions to be varied can be synthesized for example using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The libraries can also be synthesized using chemical gene synthesis according to methods described in U.S. Pat. No. 6,521,427 and U.S. Pat. No. 6,670,127, utilizing degenerate oligonucleotides matching the designed diversity. Variants in the library having random substitutions can be generated using NNK codons, which encode all 20 naturally occurring amino acids. CGT/CGC/CGA/CGG/AGA/AGG (Arg), AAT/AAC (Asn), GAT/GAC (Asp), CAT/CAC (His), TCT/TCC/TCA/TCG/AGT/AGC (Ser), TGG (Trp), TAT/TAC (Tyr), GGT/GGC/GGA/GGG (Gly) codons can be used to generate the profile of the universal set of amino acids.

Standard cloning techniques can be used to clone the libraries into a vector for expression and/or display. The library may be expressed in various formats including IgG, Fab, Fab', F(ab')2, scFv, or Fv using a known system. The libraries may also be expressed as fusion proteins and can be displayed on the surface of any suitable phage. Methods for displaying fusion polypeptides comprising antibody fragments on the surface of a bacteriophage are well known (U.S. Pat. No. 6,969,108; U.S. Pat. No. 6,172,197; U.S. Pat. No. 5,223,409; U.S. Pat. No. 6,582,915; U.S. Pat. No. 6,472,147). Libraries for de novo antibody isolation and affinity-maturation can be displayed on pIX (WO2009/085462, Tornetta et al., J Immunol Methods, 360:39-46, 2010). The libraries can also be translated in vitro, for example using ribosome display (Hanes and Pluckthun, Proc Natl Acad Sci USA, 94:4937, 1997), mRNA display (Roberst and Szostak, Proc Natl Acad Sci USA, 94:12297, 1997), or other cell-free systems (U.S. Pat. No. 5,643,768).

The resulting library can be screened for antibodies or antibody fragments of desired biological activity, for example reduced, enhanced or modify binding, cross-reactivity, affinity, on-rate, off-rate, or specificity, or any other suitable characteristic. A single point ELISA can be used to rank the binding activity of matured antibodies in comparison to the parent antibody, followed by more accurate estimation of the affinity and kinetic constants of the top ranked candidates using Biacore or KinExA analyses.

EXAMPLE 1

Determining rSDRUs rSDRUs were identified by analyzing antigen-antibody complexes available at IMGT (http://imgt cines fr), in a manner similar to previously described for a smaller set of complex structures (Almargo, J Mol Recognit. 17:132-43, 2004.). A total of 933 structures were compiled in the database in Mar. 23, 2008. Out of these, 478 entries contained antibodies in complex with proteins, peptides or haptens. The 478 structures were further filtered using the following criteria: (1) structures solved at 3.0 Å resolution or below, (2) V kappa antibodies, (3) human or mouse antibodies, and (4) unique antibodies as judged by the antibody name and sequence comparisons. After this filtering step, the resulting 142 structures included 67 antibodies in complex with proteins, 28 in complex with peptides, and 47 in complex with haptens. The dataset consisted of 91% mouse and 9% human antibodies which are summarized in FIG. 3.

Figure 4A:
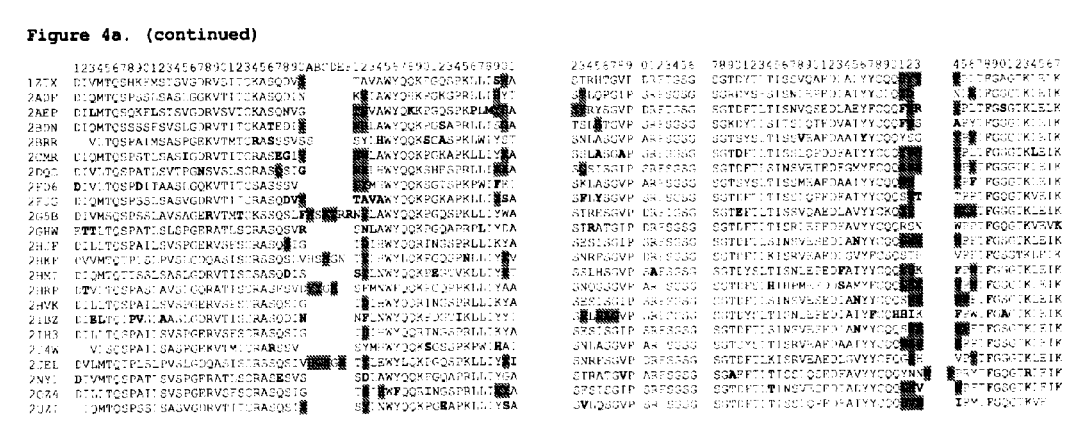
Figure 4C:
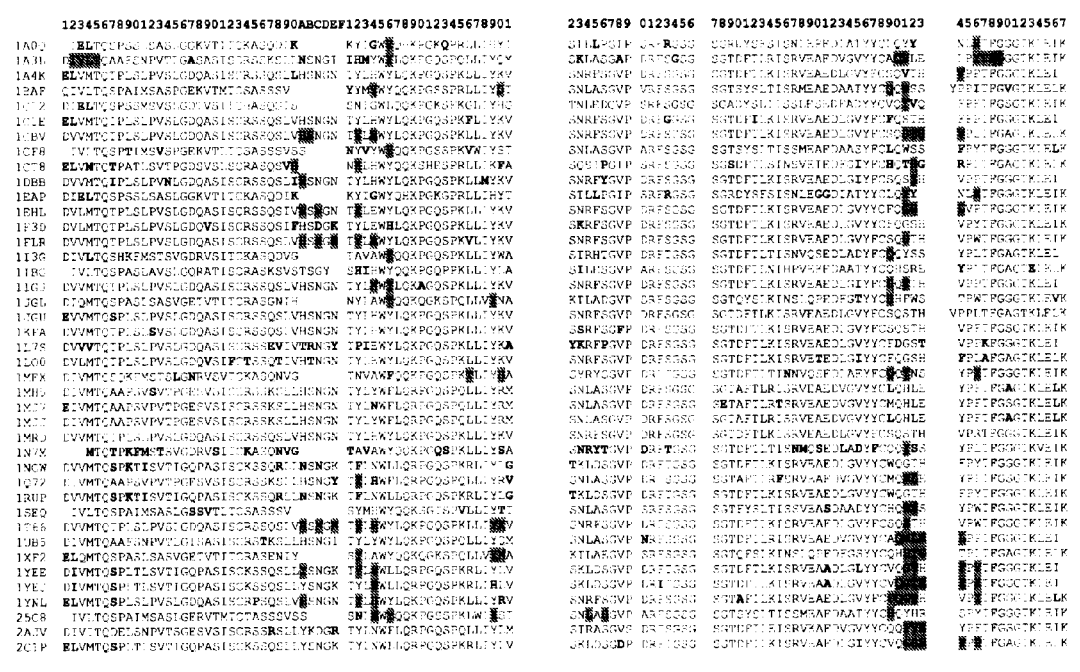
Figure 5A:
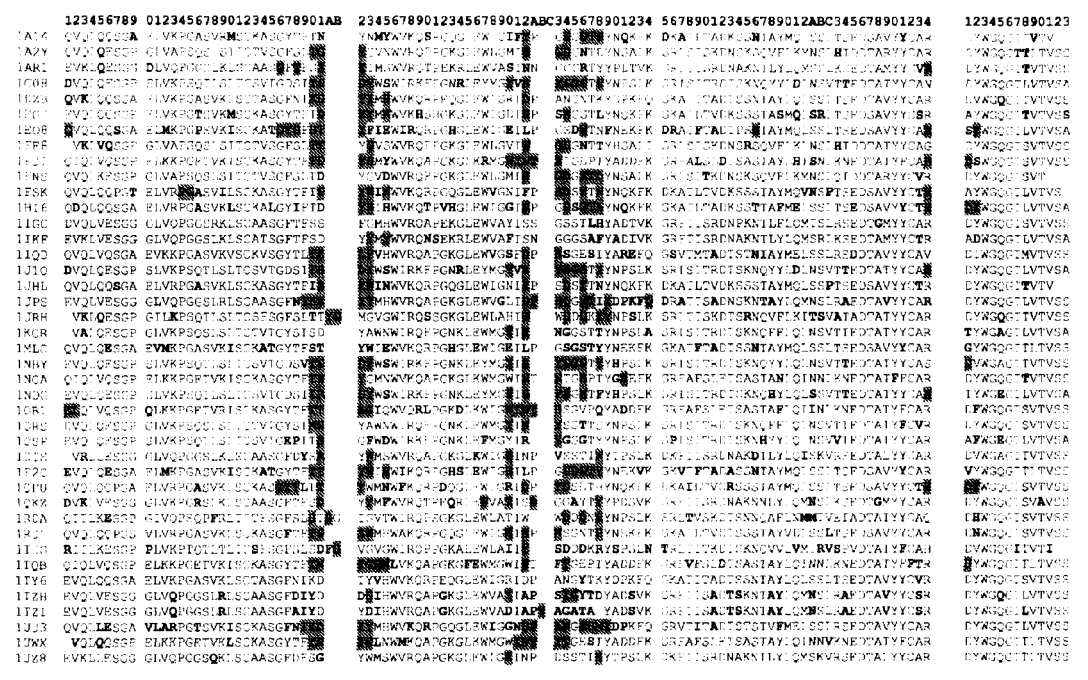
Figure 5B:
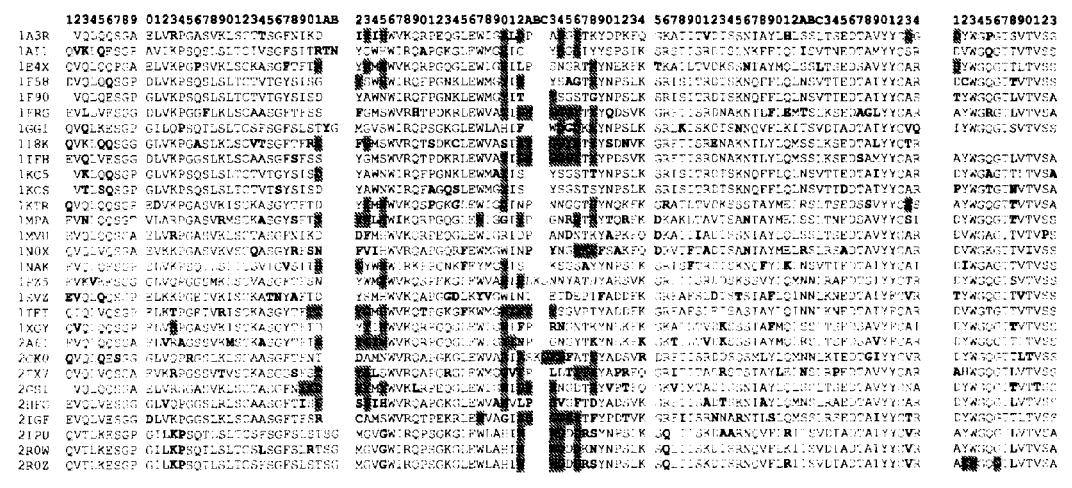

FIGS. 4 and 5 show V kappa and VH sequences of antibodies used in the study, respectively. The antibody residues identified to be in contact with the respective antigen were compiled from IMGT and are highlighted in gray. From the dataset, high, medium and low usage rSDRUs were identified. FIG. 6 shows rSDRUs within the respective SDRRs, and the data is summarized in Table 1. Five distinct SDRRs in both V kappa and VH were identified. These regions partially overlap with the CDRs and HVLs and were defined SDRR-L1, -L2, -L3, -H1 and -H2, accordingly. Table 2 shows the SDRR regions. Contacts for residues residing at CDR-H3 were not calculated due to the high variability in CDR length, conformation and amino acid content in this region. Since SDRRs identify regions of the variable chains that make contacts with antigens depending upon the type of antigen recognized, it can be used as guide in humanization protocols to reduce the number of non-human residues being transferred into a human context.

Overall, VH has more rSDRUs than V kappa for all antibody types, which could reflect the preponderant role of VH over VL in the antigen binding mechanism. In anti-protein and anti-peptide antibodies, the number and location of rSDRUs are similar but differ significantly from anti-hapten antibodies, where the magnitudes of rSDRUs in all sites are below 40, with the exception of positions 92 in V kappa and 34 in VH. In antibodies recognizing proteins and peptides, several positions reach rSDRU values above 60. Residues 32, 34 (SDRR-L1), 49, 50 (SDRR-L2) and 91-94, and 96 (SDRR-L3) make contact with all the three types of antigens. Variations are observed in the frequencies with which the three antigens contact each of these sites.

EXAMPLE 2

Calculating Specificity Determining Residue Matrices "SDRM"

Figure 9:
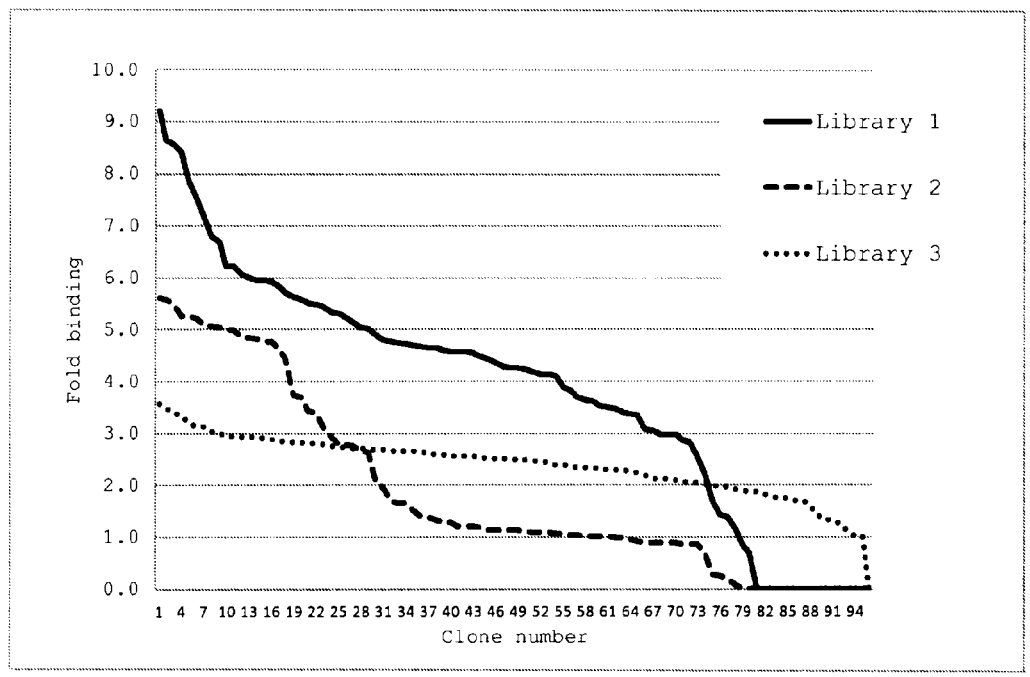
FIG. 9. Distribution of fold binding of anti-OSM affinity matured antibodies.

Amino acid distributions at each V kappa or VH rSDRUs were defined and are presented in the form of SDRMs (Specificity Determining Residue Matrices). SDRM represents the contribution of each of the 20 amino acids at each rSDRU residue (FIGS. 8 and 9). Overall, anti-protein antibodies exhibited the highest diversity in amino acid residues in the SDRMs. Anti-hapten antibodies utilized a more restricted set of amino acids to recognize the antigens.

V Kappa SDRM

Differences in the distribution of amino acid types were noted among SDRR regions and across the types of antigens in V kappa (FIG. 7). Across all antigen types, Arg, Asn, Asp, His, Ser, Thr and Tyr occur most frequently in contact sites. Cys, Pro, Gln, Glu, and hydrophobic amino acids such as Ala, Ile, Leu, Met, Phe, and Val occur less frequently. Thus, hydrophilic amino acids predominate over hydrophobic residues. Comparing different SDRR regions, Asn and Asp occur more frequently in SDRR-L1 than in SDRR-L3. In SDRR-L1, Arg is rare and Trp is absent. SDRR-L2 has less diversity than SDRR-L1 and SDRR-L3; for example, SDRR-L2 has far less Ser. Similarly, differences in SDRR distributions were observed within the same antigen class. For example, in anti-protein antibodies, Trp occurs more frequently in SDRR-L3 than in SDRR-L1 or SDRR-L2.

Similarities and differences were observed for the same region among the antibodies binding different classes of antigens. In anti-protein antibodies, the predominant residues in contact sites are: Asn, Asp, His, Lys, Ser, and Thr in SDRR-L1; Arg, Glu, Ser and Thr in SDRR-L2; and Arg, Ser, Thr, Trp, and Tyr in SDRR-L3. In anti-peptide antibodies the corresponding residues are: Arg, Asn, Asp, His, Ser, and Tyr in SDRR-L1; Tyr in SDRR-L2; and Ser, Tyr and Val in SDRR-L3. In anti-hapten antibodies the residues are: Asn, His and Ser in SDRR-L1; Ser in SDRR-L2; and Gln, Gly, His, Ser and Tyr in SDRR-L3. Layered onto these distributions are differences in relative abundance among the antigen classes. Thus, anti-protein antibodies have a greater frequency of Asp and a higher number of contact residues in SDRR-L1 and a greater frequency of Arg and Trp in SDRR-L3. In contrast, anti-hapten antibodies have more Gln, Gly, and His at antigen contact sites.

This analysis of amino acids in contact with antigen provides a guideline for residue substitution at V kappa rSDRU positions (FIG. 7). For instance, residue 34 can be diversified using amino acids NHYF in anti-protein antibodies, NEHSTY in anti-peptide antibodies, and ARNDGHSY in anti-hapten antibodies when a cutoff frequency is not defined. Likewise, light chain residue 93 can be diversified using RNEHIKMSTV in anti-protein antibodies, ARNQEHFS in anti-peptide antibodies, and EGHT in anti-hapten antibodies. If a cutoff of at least 10% occurrence is applied, the diversity at position 93 is reduced to EST, EHS, and EGH in anti-protein, anti-peptide and anti-hapten antibodies, respectively.

VH SDRM

Similar to V kappa, differences in the type of amino acids involved in the interaction with different types of antigen in VH are shown in FIG. 8. Across all antigen classes, the predominant residues in contact in the SDRR-H1 and SDRR-H2 are: Arg, Asn, and Asp in SDRR-H1; Glu, Gly, and His in SDRR-H2, and Ser, Thr, Trp and Tyr at the base of H3. As in the case of V kappa, Ser, Thr, and Tyr frequently occur in contact sites; and Cys, Pro, Gln, Glu, and hydrophobic amino acids such as Ala, Ile, Leu, Met, Phe, and Val are less abundant. In comparison to Vκ, VH has more contacts involving negatively charged amino acids, particularly in SDRR-H2. Correspondingly, Lys occurs less frequently overall and Arg occurs at low abundance in SDRR-H1.

In anti-protein antibodies, the predominant residues in contact sites are: Asn, Asp, Gly, Ser, Thr, and Tyr in SDRR-H1; and Arg, Asn, Asp, Gly, Ser, THr, and Tyr in SDRR-H2. In anti-peptide antibodies, the corresponding residues are: Asn, Gly, Ile, Ser, Thr, and Tyr in SDRR-H1; and Arg, An, Gly, Ser, Thr, Trp, and Tyr in SDRR-H2. In anti-hapten antibodies, the residues are: Asn, Gly, Ser, Thr and Tyr in SDRR-H1; and Arg, Asn, Ser, Thr, Trp, and Tyr in SDRR-H2. A guideline for residue substitution at rSDRU residues is shown in FIG. 8. For example, at VH residue 50, amino acids RNEGLMSTWYV, EGLTWY or EWY are indicated for anti-protein antibodies at cutoff frequencies of 0, 5 and 10%, respectively. The corresponding amino acids are RDEGHFTWY, REGHTWY or RGWY for anti-peptide antibodies, and RNDELMSTWYV, RESWY, or RSWY for anti-hapten antibodies.

Universal Set of Amino Acids

The universal set of amino acids was selected based on the frequency of amino acids in all rSDRU residues for both heavy and light chains and on the properties of the amino acid chains. The universal set of amino acids consists of residues Arg, Asn, Asp, Gly, His, Ser, Trp, and Tyr. In this set, Trp , Asp, and Ser may be removed in some instances as described above, resulting in alternative universal sets of amino acids consisting of amino acids Arg, Asn, Asp, Gly, His, Ser, and Tyr, or of amino acids Arg, Asn, Asp, Gly, His, Trp, and Tyr, or of amino acids Arg, Asp, His, Ser, Trp, Tyr, and Gly. A broad range of molecular recognition properties can be achieved with these limited sets of amino acids. Arg is a proxy for positively charged amino acids and its guanidinium group can participate in hydrogen bonds, both as a donor and as an acceptor. Asp provides the negative charge but is not as flexible as Glu and thus is less entropic; additionally, it can form salt bridges and act as an acceptor of hydrogen bonds. Asn can act as a hydrogen bond acceptor. His provides stacking interactions and also can contribute a positive charge in its protonation state. Trp and Tyr provide aromatic interactions, hydrogen bonding and stacking interactions. Ser provides hydrogen bonds and is also the smallest side-chain residue. Ser, and particularly Gly, provide the stereo-chemical flexibility and enables proper orientation of neighboring amino acids for interaction with antigen. The attrition in the number of possible sites and reduction in the number of substitutions at each site by the universal set of amino acids enables exploration of a large binding surface in combinatorial libraries. The universal set of amino acids can be used to diversify libraries for affinity maturing antibodies as well as libraries for de novo discovery.

EXAMPLE 3

Affinity-Maturation of Anti-Oncostatin M Antibodies

Oncostatin M (OSM) (GenBank Accession No. NP_065391) is a multifunctional member of the IL-6 family of cytokines secreted by monocytes, macrophages, neutrophils and activated T-lymphocytes (Tanaka & Miyajima, Rev Physiol Biochem Pharmacol, 149:39-53, 2003), and functions in oncogenic processes and inflammatory and hypertrophic pathways leading to deleterious conditions such as pulmonary fibrosis.

De novo Fab-pIX libraries (Shi et al., J Mol Biol, 397:385-96, 2010; WO2009/085462; U.S. Ser. No. 12/546850) were panned using biotinylated human OSM (R&D Systems, amino acids 26-221 of NP_065391) captured on paramagnetic Streptavidin beads (Invitrogen, Carlsbad, Calif.) following a published protocol for phage selection (Marks and Bradbury, Antibody Engineering, Vol. 248: 161-176, Humana Press, 2004). The libraries were generated by diversifying human germline IGVH genes IGHV1-69*01, IGHV3-23*01, and IGHV5-51*01, and human germline IGVK genes O12 (IGKV1-39*01), L6 (IGKV3-11*01), A27 (IGKV3-20*01), and B3 (IGKV4-1*01). The three resulting VH libraries were combined with the four VL libraries to generate 12 unique VH:VL combinations for screening. The confirmed OSM binding Fabs were converted to full-length human IgG1 mAbs and characterized using various assays including affinity measurements by surface Plasmon resonance (Biacore), and their ability to block Stat3 signaling. From the analyses, four mAbs, OSMM5, OSMM6, OSMM9 and OSMM10, were selected for affinity maturation. Table 3 shows the characteristics of the mAbs chosen for affinity maturation.

TABLE 3

Characterization of anti-OSM mAbs.

| mAb | $K_{D(nM)}$ | | VH | VL |
|---|---|---|---|---|
| | Human OSM | Cyno OSM | | |
| M5 | 11.85 | 12.05 | H135 | L111 |
| M6 | 1.03 | 1.48 | H14 | L12 |
| M9 | 1.22 | 0.73 | H17 | B3 |
| M10 | 1.05 | 18.9 | H2 | L2 |

Affinity Maturation

For affinity maturation, the VH chains of the mAbs OSMM5, OSMM6, OSMM9 and OSMM10 (H135, H14, H17 and H2) were combined with three distinct VL libraries displayed on pIX and panned using both huOSM (R&D Systems) and mature cynoOSM. The VL chains of mAbs M5, M6, M9 and M10 (L111, L12, B3, L2) all originated from the B3 de novo pIX library, hence B3 was selected as a template to generate libraries for affinity maturation.

One of the libraries used for maturation ("Library 3") was the same library used for de novo discovery following the procedure described by Shi et al., J Mol Biol, 397:385-396, 2010 and WO2009/085462; U.S. Ser. No. 12/546850. Diversity in this library was designed by identifying positions in the light chain most frequently observed in contact with protein and peptide antigens and using amino acids that were found at corresponding positions within the B3 germline gene family and in rearranged antibodies derived from B3. Two additional libraries, Library 1 ("focused SDRU library") and Library 2 ("NNK SDRU library"), were generated to compare the impact of choosing distinct rSDRU residues and diversification strategies on the efficiency of affinity maturation. Libraries 1 and 2 targeted the same rSDRU residues but differed in the amino acids used for diversification (Table 4).

rSDRU residues targeted for diversification in Library 1 and 2 were chosen as follows. First, positions in V kappa were identified that have a high frequency of contact with protein antigens (rSDRU>40) and that are common to all V kappa chains, excluding residues within the insertion and deletions in the V kappa chain (e.g., residues 30a-f and 95a-c). Second, a three dimensional structural model of B3 recombined with Jkappa1 was assembled and residues within the insertions 30a-f pointing in the direction of the antigen-binding site (30a, 30c, 30d, and 30f) were included in the positions to be diversified. The combined set of rSDRU residues targeted for diversification in B3 were Chothia residues 30a, 30c, 30d, 30f, 32, 50, 91, 92, 93, 94, and 96.

For Library 1, diversity at each position was the set that most frequently occur in contact with protein ligands (e.g., most frequent residues in the SDRM). For positions 30a-30f, there was not sufficient crystal structure information available to determine the contribution of the residues involved with antigen contact In these positions, the universal set of amino acids described above was used. Tryptophan (W) was included at only a few positions (e.g., 30c and 30f) to avoid potential oxidation and steric clash which could lead to aggregation.

Libraries 1 and 2 were synthesized using chemical gene synthesis according to methods described in U.S. Pat. No. 6,521,427 and U.S. Pat. No. 6,670,127. Dinucleotides were employed to tailor the diversity of Library 1 whereas degenerate oligonucleotides (NNK) were used for the synthesis of Library 2. Library 3 was constructed as described by Shi et al., J Mol Biol, 397:385-96, 2010 and WO2009/085462; U.S. Ser. No. 12/546850.

Table 4 summarizes the diversity in Libraries 1, 2 and 3. During library QC, some amino acids were identified that were not part of the original design and thus were introduced as a consequence of the synthesis method. For library 1, these amino acids were: S (position 30c), T (position 30d), EK (position 30f), IW (position 32), TV (position 50), I (position 92), D (position 93), and F (position 96).

tide which associates with the VH-CH1. Three rounds of panning were carried out with 1 nM biotinylated human OSM (R&D Systems), 0.1 nM of biotinylated mature cynoOSM, and 0.01 nM biotinylated human OSM (R&D Systems) in each round, respectively.

After panning, Fabs from each library were compared with the parent Fab for OSM binding in an ELISA assay using 2 nM and 0.2 nM of human OSM. 81.3%, 63.5%, and 97.9% of the Fabs identified from Library 1, 2 and 3, respectively, showed improved binding when compared to the parental Fab. The distribution of fold improvement relative to parental binding is shown in FIG. 9. Although, the hit rate of library 3 was better than the hit rates of libraries 1 and 2, the affinity of the antibodies generated from Libraries 1 and 2 were higher than for those from Library 3. Moreover, Library 1 yielded Fabs with the highest affinities with up to a 9-fold improvement in binding over compared parent antibodies. Thus, the combination of selecting positions based on rSDRU and diversification based on defined sets of amino acids yielded antibodies with the highest level of improved affinity.

To further characterize the outcome of the selections, selected V kappa regions obtained from the screening of Library 1 were paired with parental VH chains of OSMM6 and OSMM9, and cloned as complete IgG1/kappa constructs for exmpression in mammalian cells. Affinities of the purified antibodies for huOSM and cynoOSM were determined by BIAcore and their neutralizing potencies were measured by inhibition of STAT3 phosphorylation in cell culture (Table 5). The sequences of the selected clones at the diversified positions are shown in Table 6.

TABLE 4

| Loop | Position* | Library 1 "focused SDRM" | Library 2 "NNK SDRM" | Library 3 "pIX B3 de novo" |
|---|---|---|---|---|
| L1 | 30a | RNDGHSY | X | YSHFA |
| | 30c | RNDGHWY | X | — |
| | 30d | RNDGHSY | X | — |
| | 30f | RNDGHWY | X | KTNE |
| | 32 | RNDY | X | YFHNWDAS |
| L2 | 50 | YWNK | X | WSRDYA |
| L3 | 91 | SYGH | X | YSHA |
| | 92 | SYGN | X | YNDSHIFKG |
| | 93 | STER | X | SNTDGHR |
| | 94 | YSHT | X | TYLVFAS |
| | 96 | YRWL | X | WYFLIR |

*Chothia residue

The libraries were cloned and displayed following standard protocols (Shi et al., J Mol Biol, 397:385-96, 2010; WO2009/085462; U.S. Ser. No. 12/546850). The Fabs were displayed on pIX via expression from a dicistronic vector wherein the VH-CH1 domain is fused to the coat protein sequence and the VL-Ckappa is expressed as a free polypeptide

TABLE 5

| | | | KD (nM) | | EC50 (ng/ml) |
|---|---|---|---|---|---|
| mAb | VH | VL | huOSM | cynoOSM | huOSM |
| OSMM6 | OSMH14 | OSML12 | 1.26 | 1.66 | 650.3 |
| OSMM42 | OSMH14 | OSML173 | 0.484 | 0.516 | 191.3 |
| OSMM45 | OSMH14 | OSML176 | 0.144 | 0.159 | 50.0 |
| OSMM53 | OSMH14 | OSML184 | 0.214 | 0.147 | 236.6 |
| OSMM54 | OSMH14 | OSML185 | 0.053 | 0.057 | 78.5 |
| OSMM55 | OSMH14 | OSML186 | 0.054 | 0.058 | 181.6 |
| OSMM9 | OSMH17 | B3 | 1.42 | 0.898 | 1218.0 |
| OSMM62 | OSMH17 | OSML171 | 0.184 | 0.217 | 233.5 |
| OSMM63 | OSMH17 | OSML172 | 0.116 | 0.097 | 88.2 |
| OSMM64 | OSMH17 | OSML173 | 0.095 | 0.023 | 97.1 |
| OSMM65 | OSMH17 | OSML174 | 0.064 | 0.053 | 29.5 |
| OSMM66 | OSMH17 | OSML175 | 0.071 | 0.124 | 152.7 |
| OSMM67 | OSMH17 | OSML176 | 0.053 | 0.034 | 37.7 |
| OSMM68 | OSMH17 | OSML177 | 0.064 | 0.049 | 126.9 |
| OSMM69 | OSMH17 | OSML178 | 0.045 | 0.062 | 141.7 |
| OSMM83 | OSMH17 | OSML192 | 0.042 | 0.03 | 71.2 |

TABLE 6

| | | | Diversified position in VL | | | | | | | | | | |
|---|---|---|---|---|---|---|---|---|---|---|---|---|---|
| mAb | VH | VL | 30a | 30c | 30d | 30f | 32 | 50 | 91 | 92 | 93 | 94 | 96 |
| OSMM6 | OSMH14 | B3 OSML12 | Y | S | N | K | Y | W | Y | Y | S | T | L |
| OSMM42 | OSMH14 | OSML173 | S | R | G | N | Y | K | Y | Y | S | T | L |
| OSMM45 | OSMH14 | OSML176 | G | W | G | H | Y | K | Y | Y | S | T | L |
| OSMM53 | OSMH14 | OSML184 | G | G | Y | R | Y | W | Y | Y | T | T | L |
| OSMM55 | OSMH14 | OSML186 | S | G | S | R | Y | W | Y | Y | S | T | L |
| OSMM9 | OSMH17 | B3 | | | | | | | | | | | |
| OSMM62 | OSMH17 | OSML171 | S | G | N | G | Y | K | Y | Y | S | T | L |
| OSMM63 | OSMH17 | OSML172 | S | G | S | H | Y | K | Y | Y | S | T | L |
| OSMM64 | OSMH17 | OSML173 | S | R | G | N | Y | K | Y | Y | S | T | L |

TABLE 6-continued

| | | | Diversified position in VL | | | | | | | | | | |
|---|---|---|---|---|---|---|---|---|---|---|---|---|---|
| mAb | VH | VL | 30a | 30c | 30d | 30f | 32 | 50 | 91 | 92 | 93 | 94 | 96 |
| OSMM65 | OSMH17 | OSML174 | G | W | G | D | Y | K | Y | Y | S | T | L |
| OSMM66 | OSMH17 | OSML175 | Y | G | G | G | Y | K | Y | S | T | T | L |
| OSMM67 | OSMH17 | OSML176 | G | W | G | H | Y | K | Y | Y | S | T | L |
| OSMM68 | OSMH17 | OSML177 | S | N | G | H | Y | K | Y | Y | S | T | L |
| OSMM69 | OSMH17 | OSML178 | S | D | G | H | Y | K | Y | Y | S | T | L |
| OSMM83 | OSMH17 | OSML192 | G | W | H | D | Y | K | Y | Y | S | T | L |

All of the selected clones showed a higher affinity and neutralizing potency than their parental Abs. Affinities measured by BIAcore ranged from 30 pM to 1.7 nM. The range of affinity improvement as measured in BIAcore resembles the distribution of affinities observed in the ELISA assay used to rank the variants. Affinities for cynoOSM correlate well with huOSM. Neutralization potency did not strictly correlate with measured affinity but showed the same overall trend. This may reflect experimental fluctuation. Thus, antibodies selected from Library 1 were improved both in affinity and in vitro neutralizing potency.

Assays and Reagents

OSM Expression and Purification

Precursor and mature forms of human and Cynomolgus monkey (*Macaca fascicularis*) OSM (huOSM and cynoOSM) were expressed in HEK293 and purified using standard methodologies. Mature huOSM and cynoOSM comprise aa 1-184 of their respective precursor forms. A $His_6$ tag and an AviTag were added into the protein during the cloning process. The functional activities of the proteins were tested in the A375-S2 cell proliferation and pSTAT3 signaling assays.

ELISA Assays

After panning, glycerol stocks were made and polyclonal DNA was extracted. The gene encoding the pIX coat protein was excised from the DNA pool, which allows a polyhistidine (His) tag to be added in frame to the C terminal end of the Fab CH1 domain. After transformation into bacteria, individual clones were picked and Fabs were produced and recovered from the bacterial supernatant. Fabs were captured on black MaxiSorp plates (Nunc, Cat. No. 437111) with a sheep anti-human Fd (CH1) antibody (1 µg/ml) (The Binding Site, Cat. No. PC075). After washing and blocking, 50 µl undiluted bacterial supernatant containing the Fab was added onto plates. The plates were incubated for 1 hour at room temperature with gentle shaking. After washes, serially diluted biotinylated huOSM or CynoOSM was added into the wells, and incubated for 1 hour at room temperature, after which the signal was detected using SA-HRP (Invitrogen, Cat. No. 43-4323) and chemiluminescence.

EC50 Measurements

A375-S2 cells were seeded into 96-well tissue culture plates at 25,000 cells/well in 200 µl in complete growth media and incubated for 24 hours. Cells were treated with a solution containing 5 ng/ml huOSM pre-incubated for 3 hours at room temperature with 1:5 serially diluted experimental mAb starting at 10 µg/ml. Phosphorylated STAT3 (pSTSAT3) was measured using the Phospho-STAT3 Whole-Cell Lysate Kit (MSD; Cat. No. K150DID-1, Lot No. K0010570) following the manufacturer's protocol.

EC50 dose-response curves were obtained and plotted as normalized percent pSTAT3 signal.

Affinity Measurement by Surface Plasmon Resonance (Biacore)

The binding affinities were measured using Surface Plasmon Resonance (SPR) with a Biacore 3000 optical biosensor (Biacore) using human or Cyno OSM constructs as described. A biosensor surface was prepared by coupling anti-IgG Fc antibody mixture of anti-Mouse (Jackson, Cat. No. 315-005-046) and anti-Human (Jackson, Cat. No.109-005-098) to the carboxymethylated dextran surface of a CM-5 chip (Biacore, Cat. No. BR-1000-14) using the manufacturer's instructions for amine-coupling chemistry. Approximately 19,000 RU (response units) of anti-OSM antibody were immobilized in each of four flow cells. The kinetic experiments were performed at 25° C. in running buffer (DPBS+0.005% P20+3 mM EDTA). Serial dilutions Human and Cyno OSM ECD from 100 nM to 0.412 nM were prepared in running buffer. About 200 RU of mAb were captured on flow cells 2 to 4 of the sensor chip. Flow cell 1 was used as reference surface. Capture of mAb was followed by a three-minute injection (association phase) of antigen at 50 µl/min, followed by 10 minutes of buffer flow (dissociation phase). The chip surface was regenerated by two pulses of 18-second injections of 100 mM H3PO4 (Sigma, Cat. No. 7961) at 50 µl/min.

We claim:

1. A method of affinity maturing an antibody, comprising the steps of:
   a. obtaining an amino acid sequence of the antibody light chain variable region (VL) or the antibody heavy chain variable region (VH);
   b. identifying rSDRU residues in the amino acid sequence of the antibody VL or VH;
   c. selecting a subset of the rSDRU residues to be diversified;
   d. selecting a set of amino acids or a universal set of amino acids used for diversifying the subset of the rSDRU residues;

e. preparing a library of antibody VL or VH variants by diversifying the subset of the rSDRU residues selected in step c. with the set of amino acids selected in step d.;
f. expressing the library of antibody VH or VL variants in a host or translating the library of antibody VH or VL variants in vitro; and
g. selecting from the library of antibody VH or VL variants one or more affinity matured antibody having an improved affinity to an antigen, wherein the rSDRU residues to be diversified comprise the antibody VL Chotia residues 30a, 30c, 30d, 30f, 32, 50, 91, 92, 93, 94, and 96.

2. The method of claim 1, wherein the subset of the rSDRU residues comprises residues having rSDRU>5, rSDRU>15, rSDRU>30, rSDRU>40, or rSDRU>60.

3. The method of claim 1, wherein the subset of the rSDRU residues comprises residues having rSDRU>40.

4. The method of claim 1, wherein Trp, Asn or Ser is removed from the set of amino acids or from the universal set of amino acids.

5. The method of claim 1, wherein the universal set of amino acids is RNDGHSWY, RNDGHSY, RNDGHWY, or RDGHSWY.

6. The method of claim 1, wherein the set of amino acids in step d) comprise
   a. RNDGHSY at VL Chothia residue 30;
   b. RNDGHWY at VL Chothia residue 30a;
   c. RNDGHSY at VL Chothia residue 30c;
   d. RNDGHWY at VL Chothia residue 30f;
   e. RNDY at VL Chothia residue 32;
   f. YWNK at VL Chothia residue 50;
   g. SYGH at VL Chothia residue 91;
   h. SYGN at VL Chothia residue 92;
   i. STER at VL Chothia residue 93;
   j. YSHT at VL Chothia residue 94; and
   k. YRWL at VL Chothia residue 96.

* * * * *